United States Patent
Cardelli et al.

(10) Patent No.: US 10,603,335 B2
(45) Date of Patent: Mar. 31, 2020

(54) CANCER TREATMENT COMBINATION COMPOSITIONS, METHODS AND USES

(71) Applicant: Board of Supervisors of Louisiana State University and Agricultural and Mechanical College, Baton Rouge, LA (US)

(72) Inventors: James Cardelli, Shreveport, LA (US); Ana-Maria Dragoi, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/430,123

(22) Filed: Feb. 10, 2017

(65) Prior Publication Data

US 2017/0258929 A1  Sep. 14, 2017

Related U.S. Application Data

(60) Provisional application No. 62/294,497, filed on Feb. 12, 2016.

(51) Int. Cl.

| | | |
|---|---|---|
| *A61K 47/64* | (2017.01) | |
| *A61K 36/9066* | (2006.01) | |
| *A61K 38/09* | (2006.01) | |
| *A61K 45/06* | (2006.01) | |
| *A61K 31/7068* | (2006.01) | |
| *A61K 47/65* | (2017.01) | |
| *A61K 31/513* | (2006.01) | |
| *A61K 38/13* | (2006.01) | |
| *A61K 31/12* | (2006.01) | |

(52) U.S. Cl.
CPC .......... *A61K 31/7068* (2013.01); *A61K 31/12* (2013.01); *A61K 31/513* (2013.01); *A61K 36/9066* (2013.01); *A61K 38/09* (2013.01); *A61K 38/13* (2013.01); *A61K 45/06* (2013.01); *A61K 47/64* (2017.08); *A61K 47/65* (2017.08)

(58) Field of Classification Search
CPC .... A61K 45/06; A61K 36/9066; A61K 38/09; A61K 47/64
See application file for complete search history.

(56) References Cited

FOREIGN PATENT DOCUMENTS

WO  2005/048942 A2  6/2015

OTHER PUBLICATIONS

Aggarwal, S., et al., (DLys(6)]—luteinizing hormone releasing hormone-curcumin conjugate inhibits pancreatic cancer cell growth in vitro and in vivo, Int. J. Cancer, 2011, 129(7):1611-1623.
Limonta, P., et al., GnRH receptors in cancer: from cell biology to novel targeted therapeutic strategies, Endocr. Rev., 2012, 33(5):784-811(abstract).
Wu, J.C., et al., Chemopreventative effects of tetrahydrocurcumin on human diseases, Food Funct., 2014, 5(1):12-1 (abstract).
Suzawa, T., et al., Enhanced tumor cell selectivity of adriamycin-monoclonal antibody conjugate via a poly(ethylene glycol)—based cleavable linker, J. Control Release, 2002, 79(1-3):229-42 (abstract).

*Primary Examiner* — James H Alstrum-Acevedo
*Assistant Examiner* — Kaipeen E Yang
(74) *Attorney, Agent, or Firm* — Pillsbury Winthrop Shaw Pittman LLP

(57) ABSTRACT

The invention provides combinations and formulations including a luteinizing hormone-releasing hormone (LHRH) or a LHRH analog; and curcumin or a curcumin analog. LHRH or LHRH analog can be fused or conjugated to a curcumin or curcumin analog. Invention combinations and formulations can also include an anti-cell proliferative drug. Invention combinations and formulations can be used for inhibiting proliferation of a cell; treating a hyperproliferative disorder; and treating a neoplasia, tumor, cancer or malignancy.

33 Claims, 41 Drawing Sheets

Specification includes a Sequence Listing.

HPNE : normal pancreatic cell line
PANC-1: pancreatic cancer cell line
MiaPaCa-2: pancreatic cancer cell line
ASPc-1: pancreatic cancer cell line
BxPc-3: pancreatic cancer cell line Examine LHRH-R expression with PDX TMA
(50 PDXs) and gene expression database Re-implant 20 LHRH-R high PDX tumors in mice Analysis of LHRH-curcumin alone or in combination
with other agents with LTSA a=0; b=1; c=2; d=3

CANCER TREATMENT COMBINATION COMPOSITIONS, METHODS AND USES

RELATED APPLICATIONS

This application claims priority to U.S. Provisional Patent Application No. 62/294,497, filed on Feb. 12, 2016, which application is incorporated herein by reference in its entirety, including all text, tables, sequence listings and drawings.

SEQUENCE LISTING

The instant application contains a Sequence Listing which has been submitted electronically in ASCII format and is hereby incorporated by reference in its entirety. Said ASCII copy, created on Apr. 25, 2017, is named "K-94-0450018_ST25.txt" and is 1,463 bytes in size.

INTRODUCTION

Pancreatic carcinomas are devastating malignancies and the development of effective treatments that have reduced side effects proved to be challenging. Pancreatic cancer is one of the deadliest human malignancies with a 5-year survival rate of less than 14% for stage I and less than 1% for stage IV. Due to the fact that most cases are diagnosed at advanced stages the treatment options for pancreatic cancer are very limited and mostly palliative. Although the molecular and genetic bases of the pancreatic cancer have been extensively studied the treatment options are still limited. Despite significant discoveries in the genetic and molecular events behind pancreatic cancer development the prognosis remained largely unchanged for the past several decades. This is partly due to no specific detectable biomarkers to help identify patients with increased risk of pancreatic cancer and the fact that pancreatic cancer is highly heterogenic, making targeted therapies more difficult.

Currently gemcitabine (2',2'-difluoro 2'deoxycytidine) is the drug of first choice and offers short term improvement in the quality of life, with a little impact on long term survival. Gemcitabine and 5-fluorouracil (5FU)-based combination therapies are attempted to increase survival but these therapies are often accompanied by increased toxicity. While gemcitabine and 5FU-combinatorial therapies are attempted with slight improvement in overall survival, they are also accompanied by significant toxicities. Thus, only patients with good performance status can benefit from these therapies.

Gonadotropin-releasing hormone (GnRH, also called luteinizing hormone releasing hormone or LHRH) and the LHRH receptor (LHRHR) play important roles in reproduction and several malignant tumors, such as cancers of the endometrium, ovary, breast, prostate and melanomas. Until recently, the role of LHRH and its cognate receptor LHRHR in pancreatic cancer has received little attention.

Epidemiologic and animal studies have shown that natural compounds can help prevent and treat cancer. Some of these compounds have shown significant anti-tumor activity, both in vitro and in preclinical testing. Curcumin is a dirylheptanoid present in turmeric (Curcumin longa) and has been reported to have potent anti-proliferative and pro-apoptotic effects on cancer cells in vitro. While curcumin is pharmacologically safe, it has low solubility in water and therefore has poor bioavailability and cannot be administered intravenously.

SUMMARY

The studies disclosed herein show that a soluble form of Curcumin conjugated to luteinizing hormone releasing hormone (LHRH), aka LHRH-Curcumin, has a remarkable impact on pancreatic cell lines growth alone and in combination with gemcitabine. Using a three dimensional (3D) high throughput assay platform a soluble form of curcumin conjugated to LHRH (LHRH-curcumin) and anti-cell proliferative drug gemcitabine (2', 2'-difluoro 2'deoxycytidine) is more effective against pancreatic cancer cells expressing LHRH receptor (LHRHR) then curcumin or LHRH-curcumin alone. LHRH-Curcumin is an excellent candidate for combination therapies together with gemcitabine. The present invention establishes that LHRH-receptor targeted curcumin and an anti-cell proliferative drug such as gemcitabine is a viable therapy against LHRHR expressing cancers, such as pancreatic cancer, and that the combination provides effective therapy at reduced drug cytotoxicity.

In accordance with the invention, there are provided combinations and formulations of LHRH-Curcumin, LHRH-Curcumin analog, LHRH analog-Curcumin and/or LHRH analog-Curcumin analog conjugates or fusions, and one or more anti-cell proliferative drugs. In one embodiment, a combinations and formulations includes LHRH or a LHRH analog; and curcumin or a curcumin analog, where the LHRH or LHRH analog is fused or conjugated to the curcumin or curcumin analog; and an anti-cell proliferative drug.

LHRH analogs in conjugates or fusions include, but are not limited to: [D-Ala6]-LHRH; [DLys6]-LHRH; [D-Trp6]-LHRH; [Trp6]-LHRH; [D-Phe6]-LHRH; [D-Leu6]-LHRH; [D-Ser(t-Bu)6]-LHRH; [D-His(Bzl)6]-LHRH; [D-Nal(2)6]-LHRH; [Gln8]-LHRH; [His(3-Methyl)2]-LHRH; [des-Gly10, D-Ala6]-LHRH ethylamide; [-Me-Leu7]-LHRH; [des-Gly10, D-His2, D-Trp6, Pro9]-LHRH ethylamide; [des-Gly10, D-His(Bzl)6]-LHRH ethylamide; [des-Gly10, D-Phe6]-LHRH ethylamide; [aza-Gly10]-LHRH; [D-Ala6, N-Me-Leu7]-LHRH; [D-His(benzyl)6]-LHRH fragment 3-9 ethylamide; [D-His(Bzl)6]-LHRH fragment 1-7; [D-His(Bzl)6]-LHRH fragment 2-9; [D-His(Bzl)6]-LHRH fragment 4-9; [DHis(Bzl)6]-LHRH fragment 5-9; [D-pGlu1, DPhe2,D-Trp3,6]-LHRH; [D-Ser4]-LHRH; [D-Trp6]-LHRH-Leu-Arg-Pro-Gly-NH2; [des-Gly10, D-Ala6]-LHRH ethylamide; [des-Gly10,12 D-His(Bzl)6]-LHRH ethylamide; [des-Gly10, D-His2, D-Trp6, Pro9]-LHRH ethylamide; [des-Gly10, D-Phe6]-LHRH ethylamide; [des-Gly10, D-Ser4, D-His(Bzl)6, Pro9]-LHRH ethylamide; [des-Gly10, D-Ser4, D-Trp6, Pro9]-LHRH ethylamide; [des-Gly10, D-Trp6, D-Leu7, Pro9]-LHRH ethylamide; [des-Gly10, D-Trp6]-LHRH ethylamide; [des-Gly10, D-Tyr5, D-Trp6, Pro9]-LHRH ethylamide; [des-pGlu1]-LHRH; [His(3-Methyl)2]-LHRH; [Hyp9]-LHRH; Formyl [D-Trp6]-LHRH Fragment 2-10; LHRH Fragment 1-2; LHRH Fragment 1-4; LHRH fragment 4-10; LHRH fragment 7-10 ihydrochloride; [D-Trp6]-LHRH fragment 1-6; nafarelin (Synarel™); deslorelin; a EHWSYGLRPG (SEQ ID NO:1) sequence; leuprolide; leuprolide acetate (Lupron™); Goserelin (Zoladex™); Histrelin (Supprelin™); Triptorelin (Trelstar™); Buserelin (Suprefact™); Cetrorelix (Cetrotide™); Ganirelix (Antagon™); Antide (Ala-Phe-Ala-Ser-Lys-Lys-Leu-Lys-Pro-Ala) (SEQ ID NO:2); Abarelix (Plenaxis™); Teverelix (Antarelix™); Degarelix (Firmagon™); Nal-Glu (D2-Nal-p-Chloro-D-Phe-BETA-(3-Pyridyl)-D-Ala-Ser-Arg-D-Glu-Leu-Arg-Pro-D-Ala); or Elagolix (NBI-56418).

LHRH and LHRH analogs include salt forms, such as a sodium or an acetate salt. LHRH and LHRH analogs also include D-amino acids, which amino acids can be present at any residue.

The Curcumin structure in conjugates or fusions include, but are not limited to the following structures:

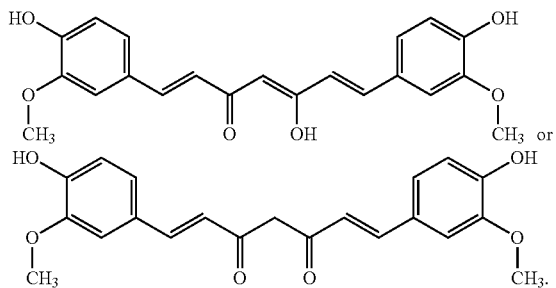

Curcumin analogs in conjugates or fusions include, but are not limited to: tetrahydrocurcumin; 6-hydroxydibenzoylmethane; caffeic acid; 3,4-methylenedioxy cinnamic acid; 3,4-dimethoxy cinnamic acid; cinnamic acid; zingerone; 4-(3,4-methylenedioxyphenyl)-2-butanone; 4-(phydroxyphenyl)-3-buten-2-one; 4'-hydroxyvalerophenone; 4-13 hydroxybenzylacetone; 4-hydroxybenzophenone; 1,5-bis(4-dimethylaminophenyl)-1,4-pentadien-3-one; 4-hydroxyphenethyl alcohol; 4-hydroxyphenyl pyruvic acid; 3,4-dihydroxyhydrocinnamic acid; 2-hydroxycinnamic acid; 3-hydroxycinnamic acid; 4-hydroxycinnamic acid or eugenol.

Curcumin analog structures in conjugates or fusions also include, but are not limited to the following structures:

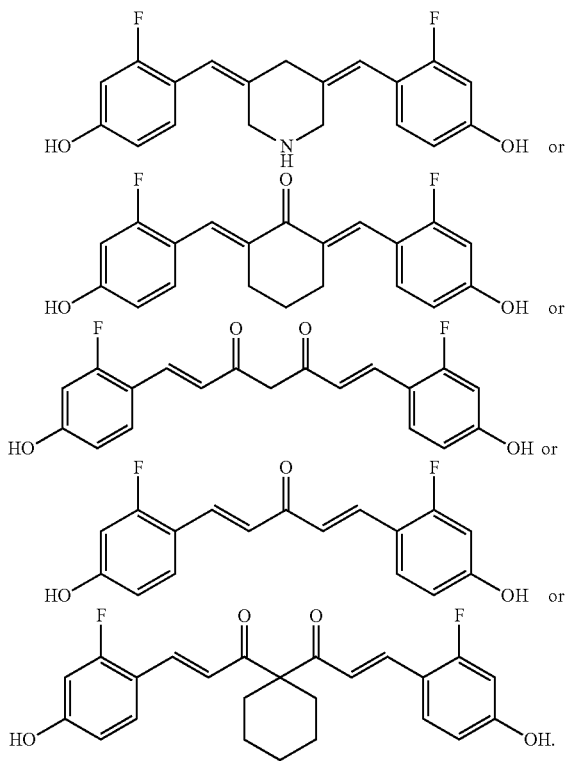

In the conjugates or fusions of the invention, LHRH or LHRH analog can be fused or conjugated to the curcumin or a curcumin analog by a bond. Non-limiting examples of bonds include covalent, ionic or hydrophobic bonds.

In the conjugates or fusions of the invention, LHRH or LHRH analog can be fused or conjugated to the curcumin or a curcumin analog by a linear carbon chain, a peptide or a non-peptide linker. Linear carbon chains be from 1-25 carbons, represented by $C_{1-25}$. Representative peptide linkers can have a length from about 1 to 25 amino acid residues. Amino acids comprising the bond or the linker include one or more A, S or G amino acid residues.

Compositions and formulations of the invention include pharmaceutical compositions and formulations. In certain embodiments, a pharmaceutical composition or formulation includes the combination of a conjugate or fusion and one or more anti-cell proliferative drugs.

In particular aspects, an anti-cell proliferative drug comprises an anti-cancer or anti-tumor drug. In more particular aspects, an anti-cell proliferative drug comprises an alkylating agent, anti-metabolite, plant extract, plant alkaloid, nitrosourea, hormone, nucleoside analog or a nucleotide analog. Particular non-limiting examples of anti-cell proliferative drugs include: gemcitabine, 5-fluorouracil, cyclophosphamide, azathioprine, cyclosporin A, prednisolone, melphalan, chlorambucil, mechlorethamine, busulphan, methotrexate, 6-mercaptopurine, thioguanine, cytosine arabinoside, AZT, 5-azacytidine (5-AZC), bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol (paclitaxel), vinblastine, vincristine, doxorubicin, dibromomannitol, irinotecan, topotecan, etoposide, teniposide, or pemetrexed.

In accordance with the invention, there are provided methods and uses for reducing or inhibiting proliferation of a cell. In one embodiment, a method or use includes contacting a cell that expresses a receptor that binds to a LHRH or a LHRH analog with a LHRH or a LHRH analog fused or conjugated to curcumin or a curcumin analog; and contacting the cell with an anti-cell proliferative drug. Such methods and uses include, without limitation, contact of cells in vivo, in a subject such as a mammal, e.g., a human, with the combination or formulation of a conjugate or fusion and one or more anti-cell proliferative drugs.

In accordance with the invention, there are also provided methods and uses for treating a hyperproliferative disorder. Such methods and uses include, without limitation, contact of hyperproliferative cells in vivo, in a subject such as a mammal, e.g., a human, with the combination or formulation of a conjugate or fusion and one or more anti-cell proliferative drugs. In one embodiment, a method or use includes contacting cells of the hyperproliferative disorder that express a receptor that binds to a LHRH or a LHRH analog with a hormone (LHRH) or a LHRH analog fused or conjugated to curcumin or a curcumin analog; and contacting said cells of the hyperproliferative disorder with an anti-cell proliferative drug. The cells may be contacted with the conjugate or fusion and one or more anti-cell proliferative drugs in a combination or via separate administrations, e.g., contact separated by time.

In accordance with the invention, there are further provided methods and uses for treating a neoplasia, tumor, cancer or malignancy that express a receptor that binds to LHRH or a LHRH analog. In one embodiment, a method or use includes administering to a subject such as a mammal, e.g., a human a LHRH or a LHRH analog fused or conjugated to curcumin or a curcumin analog; and administering to the subject an anti-cell proliferative drug. Such methods and uses include, without limitation, administration to a subject such as a mammal, e.g., a human, with the formulation of a conjugate or fusion and one or more anti-cell proliferative drugs in a combination or via separate administrations, e.g., administration separated by time.

In certain embodiments, the conjugate or fusion, e.g., LHRH or a LHRH analog fused or conjugated to curcumin or a curcumin analog, is administered prior to administration of the one or more anti-cell proliferative drugs. In certain embodiments, the conjugate or fusion, e.g., LHRH or a LHRH analog fused or conjugated to curcumin or a curcumin analog, is administered substantially contemporaneously with administration of the one or more anti-cell proliferative drugs In certain embodiments, the conjugate or fusion, e.g., LHRH or a LHRH analog fused or conjugated to curcumin or a curcumin analog, is administered following administration of the one or more anti-cell proliferative drugs.

Receptors that bind to LHRH or LHRH analog include a LHRH-receptor. In certain embodiments, receptors such as LHRH-receptors may be present on the cell surface.

Cells, hyperproliferative disorders and neoplasia, tumor, cancer and malignancy may be present systemically, regionally, locally or in a particular tissue or organ of a subject. In certain embodiments, cells, a hyperproliferative disorder, neoplasia, tumor, cancer or malignancy is present in lung, thyroid, head or neck, nasopharynx, throat, nose or sinuses, brain, spine, breast, adrenal gland, pituitary gland, thyroid, lymph, gastrointestinal, mouth, esophagus, stomach, duodenum, ileum, jejunum, small intestine, colon, rectum, genitourinary tract, uterus, ovary, cervix, endometrial, bladder, testicle, prostate, kidney, pancreas, liver, bone, bone marrow, lymph, blood, skin or muscle.

In certain embodiments, hyperproliferative disorders, neoplasia, tumor, cancer and malignancy may progressively worsening, or is in remission. In certain embodiments, cells, hyperproliferative disorder or neoplasia, tumor, cancer or malignancy is metastatic. In certain embodiments, cells, hyperproliferative disorder or neoplasia, tumor, cancer or malignancy comprise a solid cellular neoplasia, tumor, cancer or malignancy, or a lymphatic or hematopoietic cell neoplasia, tumor, cancer or malignancy, such as, e.g., a myeloma, lymphoma or leukemia.

In certain embodiments, cells, hyperproliferative disorder or neoplasia, tumor, cancer or malignancy comprises a carcinoma, sarcoma, lymphoma, leukemia, adenoma, adenocarcinoma, melanoma, glioma, glioblastoma, meningioma, neuroblastoma, retinoblastoma, astrocytoma, oligodendrocytoma, mesothelioma, reticuloendothelial neoplasia, tumor, cancer or malignancy.

In certain embodiments, sarcoma comprises a lymphosarcoma, liposarcoma, osteosarcoma, chondrosarcoma, leiomyosarcoma, rhabdomyosarcoma or fibrosarcoma.

In certain embodiments, an anti-cell proliferative drug includes: gemcitabine, 5-fluorouracil, cyclophosphamide, azathioprine, cyclosporin A, prednisolone, melphalan, chlorambucil, mechlorethamine, busulphan, methotrexate, 6-mercaptopurine, thioguanine, cytosine arabinoside, AZT, 5-azacytidine (5-AZC), bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol (paclitaxel), vinblastine, vincristine, doxorubicin, dibromomannitol, irinotecan, topotecan, etoposide, teniposide, or pemetrexed.

In certain embodiments, a method or use inhibits or reduces relapse or progression of the neoplasia, tumor, cancer or malignancy.

In certain embodiments, a method or use results in partial or complete destruction of the neoplastic, tumor, cancer or malignant cell mass, volume, size or numbers of cells, stimulating, inducing or increasing neoplastic, tumor, cancer or malignant cell necrosis, lysis or apoptosis, reducing neoplasia, tumor, cancer or malignancy volume size, cell mass, inhibiting or preventing progression or an increase in neoplasia, tumor, cancer or malignancy volume, mass, size or cell numbers, or prolonging lifespan.

In certain embodiments, a method or use reduces or decreases severity, duration or frequency of an adverse symptom or complication associated with or caused by the neoplasia, tumor, cancer or malignancy, or pain, discomfort, nausea, weakness or lethargy.

In certain embodiments, a method or use increases energy, appetite, improved mobility or psychological well being of a subject.

In certain embodiments, a cell, hyperproliferative disorder or neoplasia, tumor, cancer or malignancy is present in a mammal.

In certain embodiments, a subject or mammal is a human. In certain embodiments, a subject or mammal is a domestic or farm (livestock) animal. In certain embodiments, the domestic animal is a dog or a cat.

In certain embodiments, the LHRH or a LHRH analog fused or conjugated to curcumin or a curcumin analog and/or the anti-cell proliferative drug is administered to the subject or mammal locally, regionally, or systemically, or into the cell, hyperproliferative disorder or neoplasia, tumor, cancer, or metastasis.

In certain embodiments, a combination or formulation, method or use set forth herein, includes one or more additional anti-cell proliferative or immune-enhancing drugs, or administration of one or more additional anti-cell proliferative or immune-enhancing drugs.

In certain embodiments, an additional anti-cell proliferative drug comprises an anti-cancer or anti-tumor drug.

In certain embodiments, an additional anti-cell proliferative drug comprises an alkylating agent, anti-metabolite, plant extract, plant alkaloid, nitrosourea, hormone, nucleoside or a nucleotide analog.

In certain embodiments, an additional anti-cell proliferative drug comprises gemcitabine, 5-fluorouracil, cyclophosphamide, azathioprine, cyclosporin A, prednisolone, melphalan, chlorambucil, mechlorethamine, busulphan, methotrexate, 6-mercaptopurine, thioguanine, cytosine arabinoside, AZT, 5-azacytidine (5-AZC), bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol (paclitaxel), vinblastine, vincristine, doxorubicin, dibromomannitol, irinotecan, topotecan, etoposide, teniposide, or pemetrexed.

DESCRIPTION OF THE DRAWINGS

FIG. 18A, Tumor volumes at necropsy. Treatments were performed as presented. Data are presented as the mean±SD of tumor volume (n=8). Tumor volume at necropsy was significantly reduced in gemcitabine alone, LHRH curcumin alone or in the combination treatment group (**, p<0.025). Importantly, the combination treatment group showed the most effective reduction in tumor growth, significantly lower than gemcitabine or LHRH-curcumin alone (*, p<0.05). FIG. 18B, Tumor weight at necropsy. Data are presented as the mean±SD of tumor weight (n=8). The combination treatment group shows a significant reduction in tumor growth comparing to control group (**, p<0.025) and comparing to gemcitabine or LHRH-curcumin treatment alone (*, p<0.05).

FIG. 22A, Tumor volumes at necropsy. Treatments were performed as presented. Data are presented as the mean±SD of tumor volume (n=8). Tumor volume at necropsy was significantly reduced in gemcitabine alone, LHRH curcumin alone or in the combination treatment group (**, $p<0.025$). Importantly, the combination treatment group showed the most effective reduction in tumor growth, significantly lower than gemcitabine or LHRH-curcumin alone (*, $p<0.05$; , $p<0.025$). FIG. 22B, Tumor weight at necropsy. Data are presented as the mean±SD of tumor weight (n=8). The combination treatment group shows a significant reduction in tumor growth comparing to control group (, $p<0.025$) and comparing to gemcitabine or LHRH-curcumin treatment alone (*, $p<0.05$; **, $p<0.025$).

FIG. 28A Quantitative PCR analysis of mRNA levels of genes involved in the TGFβ pathway in cancer cells treated with TGFβ (100 ng/ml) and LHRH-curcumin (20 μM and 50 μM). Cells were treated for 24 h and 48 h respectively as displayed. GAPDH was used as a reference. Genes important for TGFβ signaling pathway were down-regulated by LHRH curcumin treatment, including SMAD3, transcription factors SNAI1 (Snail) and SNAI2 (Slug) and the TGFβ receptors (TGFBRI and TGFBRII); FIG. 28B Genes involved in cell cycle arrest (GADD45) and inhibition of apoptosis (XIAP) were also affected by LHRH-curcumin treatment.

DETAILED DESCRIPTION

Figure 1A:
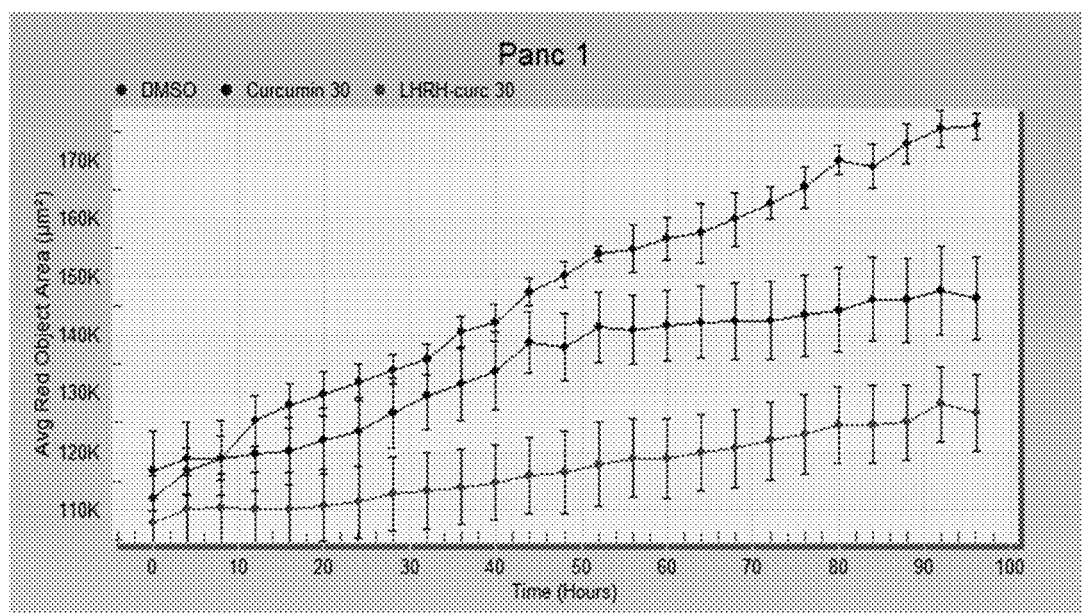
FIG. 1A-1B shows Automated measurement of spheroid growth using the Incucyte platform

The invention provides an efficient treatment against tumor growth. Conjugating luteinizing hormone releasing hormone (LHRH) to curcumin (LHRH-Curcumin) enhances water solubility (compared to native unconjugated curcumin), targets the curcumin to cells expressing luteinizing hormone releasing hormone receptor (LHRHR), facilitates intravenous administration, and maintains anti-cancer activity of curcumin while enhancing bioavailability at lower dosages. Curcumin does not appear to induce apoptosis in normal (noncancerous) cells. Thus, it is believed that LHRH-Curcumin targets and induces apoptosis in LHRHR expressing cancer cells, such as human pancreatic cancer cells and other cancer cells that express LHRH receptors. The LHRH decapeptide (and analogs thereof) can be used to target cell surface receptors so that anticancer drugs are delivered specifically to the cancer cells expressing the LHRH receptors which include, but are not limited to pancreas, prostate, breast, testicular, uterine, ovarian, and melanoma.

Such targeted therapy will be of great benefit for patients with early (e.g., primary), progressed (e.g., regional) or advanced (metastatic) stages of tumors expressing LHRHR such as pancreas, prostate, breast, testicular, uterine, and ovarian tumors. LHRH-Curcumin or LHRH-Curcumin analogs will bind to membrane receptors on cancer cells and be internalized by the cells, rendering the cancer cells more susceptible to apoptosis. Accordingly, the invention provides LHRH-Curcumin and LHRH-Curcumin analog conjugates compositions, including combinations with a second chemotherapeutic, and methods to prevent, treat, or reduce early (e.g., primary), progressed (e.g., regional) or advanced (metastatic) stages of tumors, or the progression, metastasis or recurrence of cancer.

As used herein, the terms "conjugate" or "fusion" and grammatical variations thereof, means a molecule or construct that contains portions or sections that are derived from, obtained or isolated from, or are based upon or modeled after two molecular entities that are distinct from each other and do not typically exist together in nature. That is, for example, one portion of the conjugate or fusion includes or consists of Curcumin or Curcumin analog and a second portion of the construct includes or consists of LHRH or LHRH analog that has binding affinity for LHRHR, each of the domains structurally distinct. A compound that is a "conjugate" of two molecular entities can have the two entities (or moieties) covalently bonded to one another, either directly or via a linker. Particular non-limiting examples of conjugates or fusions are: LHRH-Curcumin, LHRH-Curcumin analog, LHRH analog-Curcumin and LHRH analog-Curcumin analog.

A "receptor" such as a LHRH-receptor (denoted "LHRHR") is typically present on (e.g., a membrane receptor) or within a cell. A receptor may associate with the cell membrane surface or traverse the cell membrane. For example, a protein receptor can have a transmembrane domain that traverses the cell membrane, optionally with a portion that is cytoplasmic or extracellular, or both. Receptors therefore include full length intact native receptors containing an extracellular, transmembrane or cytoplasmic portion, as well as truncated forms or fragments thereof (e.g., an extracellular, transmembrane or cytoplasmic portion or subsequence of the receptor alone, or in combination).

LHRH-curcumin conjugate is water-soluble and saline-soluble, and may readily be administered by intravenous injection or other route. Water solubility of LHRH-curcumin conjugate is itself surprising, as previous attempts to make curcumin derivatives water-soluble have not been particularly successful. Solubility of the conjugate in saline (PBS) at room temperature is at least up to 1.2 mg per 50 µL (=24 g/L), although the upper limit of solubility has not been studied.

In addition to Curcumin and LHRH, analogs of each component may also be used in conjugates in accordance with the invention.

Analogs of curcumin are described in various publications. For example, analogs of curcumin are described in "Curcumin: From ancient medicine to current clinical trials," *Cellular and Molecular Life Sciences* 2008; 65: 1631-1652, and references 160, 161, 162, 169, and 171 therein. See also Aggarwal et al., "Curcumin (diferuloylmethane) down-regulates expression of cell proliferation and anti-apoptotic and metastatic gene products through suppression of I {kappa} B {alpha} kinase and AKT activation," *Mol Pharmacol* 2006; 69(1):195-206; U.S. Pat. No. 7,355,081; and published PCT application WO 2008/045534.

Other references that disclose Curcumin analogs include the following: Nakagawa-Goto, et al., "Antitumor agents. Syntheses and evaluation of dietary antioxidant-taxoid conjugates as novel cytotoxic agents," *Bioorganic & Medicinal Chemistry Letters* 2007; 17:5204-5209; Liu, J.; Jiang, F., "Design, synthesis, and primary evaluation on curcumin derivative as prodrugs of antitumor," Zhongguo Yaoshi (Wuhan, China) 2005; 8:543-545; Rieks, et al., "Preparation of novel curcumin/tetrahydrocurcumin derivatives for use in cosmetics, pharmaceuticals and for nutrition," WO 2004/03112; Rieks, et al., "Preparation of curcumin esters for use in cosmetics, pharmaceuticals, and food additives," German patent application DE10245988A1; Scaramuzzino, G., "Preparation of nitrate prodrugs able to release nitric oxide in a controlled and selective way and their use for prevention and treatment of inflammatory, ischemic and proliferative diseases," European patent 1336602; and Sethi, S. C.; Rao, B. C. S., "Coloration of vanaspati," Indian Journal of Technology 1964; 2:208.

It has been reported that a portion of the curcumin molecule structure is essential for at least some of curcumin's physiological effects (desaturase inhibition). Thus, LHRH conjugated to that half of the curcumin molecule may be an effective analog. See Kawashima et al., "Inhibition of rat liver microsomal desaturases by curcumin and related compounds," *Biosci Biotechnol Biochem* 1996; 60(1):108-10.

Analogs of LHRH, both agonists and antagonists, are known in the art, and either may be used in practicing the invention. See, e.g., "Cancer chemotherapy based on targeting of cytotoxic peptide conjugates to their receptors on tumors," European Journal of Endocrinology (1999) 141:1-14. Antagonists of LHRH include, for example, Antide, Buserelin, Leuprolide acetate salt, [D-Ala⁶]-LHRH, [D-Lys⁶]-LHRH, [D-Trp⁶]-LHRH, [Gln⁸]-LHRH, [His(3-Methyl)²]-LHRH, [des-Gly¹⁰, D-Ala⁶]-LHRH ethylamide, [des-Gly¹⁰, D-His², D-Trp⁶, Pro⁹]-LHRH ethylamide, [des-Gly¹⁰, D-His(Bzl)⁶]-LHRH ethylamide, and [des-Gly¹⁰, D-Phe⁶]-LHRH ethylamide.

Figure 8A:
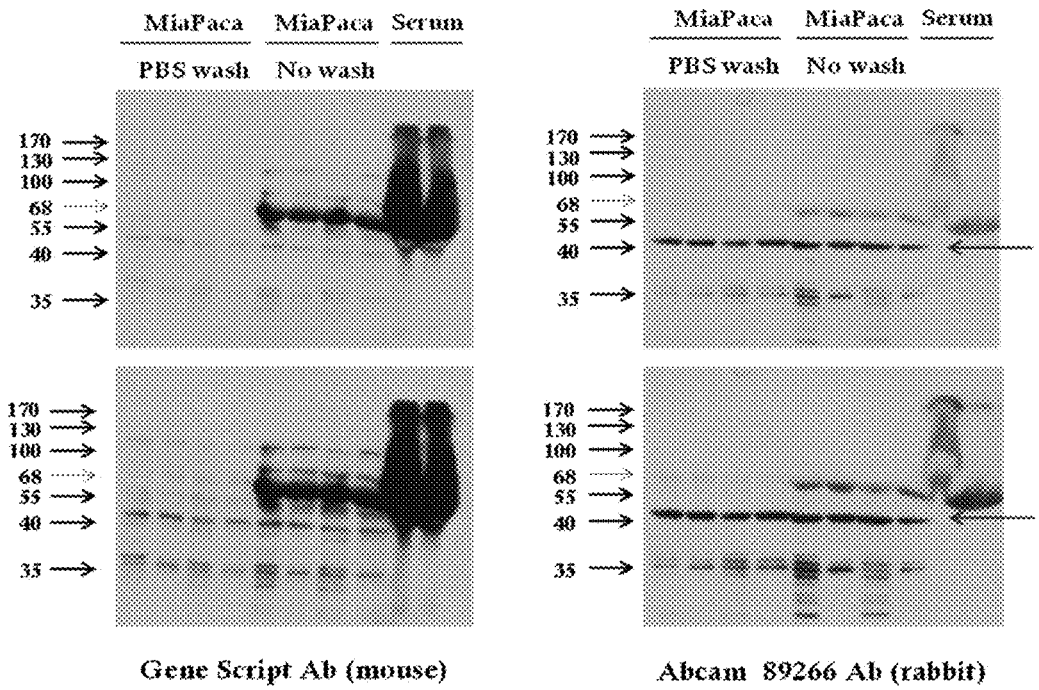
FIG. 8A shows Detection of a 45 kD protein has the LHRH receptor and very low presence of this receptor.

Representative of the many examples of LHRH analogs are described in the following literature: S. Sealfon et al., "Molecular mechanisms of ligand interaction with the gonadotropin-releasing hormone receptor," *Endocrine Reviews*, vol. 18, pp. 180-205 (1997) is a review paper that, among other things, discusses the apparent role of each of the individual amino acids in the GnRH decapeptide, and gives extensive guidance on the types of substitutions that may be made in analogs. See particularly pp. 184-191, and the schematic summary shown in FIG. 8 on page 190. A review paper, M. Karten et al., "Gonadotropin-releasing hormone analog design. Structure-function studies toward the development of agonists and antagonists: rationale and perspective," *Endocrine Reviews*, vol. 7, pp. 44-66 (1986), described or gave citations to over 2000 GnRH analogs (p. 44, par. 1). Another review is S. Sealfon et al., "The gonadotrophin-releasing hormone receptor: structural determinants and regulatory control," *Human Reproduction Update*, vol. 1, pp. 216-230 (1995) which provides a review of GnRH receptor structure and regulation of receptor expression. This review mentions that thousands of GnRH analogs have been synthesized and studied (p. 216).

Another review article is M. Filicori, "Gonadotropin-releasing hormone agonists: a guide to use and selection," *Drugs*, vol. 48, pp. 41-58 (1994) is a review discussing a number of GnRH agonists, and examples of the types of modifications that may be used to make agonists. Among the examples mentioned are replacement of the tenth amino acid (glycine) of the native GnRH sequence with an ethylamide residue; or substitution of the sixth amino acid residue (glycine) with other more lipophilic D-amino acids such as D-Phe, D-Leu, or D-Trp; or incorporation of more complex amino acids in position 6, such as D-Ser (t-Bu), D-His (Bzl), or D-Nal(2); or in position 10, such as aza-Gly; or the N-Me-Leu modification in position 7 (see pp. 42 and 43). These modifications were said to result in more hydrophobic compounds that were more stable than the native GnRH molecule, and thus to have higher receptor affinity and in vitro potency. In addition, the more hydrophobic GnRH agonists were said to be more resistant to enzyme degradation, and to bind more strongly to plasma proteins and body tissues, thus decreasing renal excretion and increasing half-life. This review also discusses various routes of administration and delivery systems.

Still further, P. Conn et al., "Gonadotropin-releasing hormone and its analogues," *New Engl. J. Med.*, vol. 324, pp. 93-103 (1991) describes several GnRH analogs including, as shown in Table 1 on p. 95, the analogs decapeptyl, leuprolide, buserelin, nafarelin, deslorelin, and histrelin; and additional analogs on p. 99.

A. Nechushtan et al., "Adenocarcinoma cells are targeted by the new GnRH-PE₆₆ chimeric toxin through specific gonadotropin-releasing hormone binding sites," *J. Biol. Chem.*, vol. 298, pp. 11597-11603 (1997) discloses a GnRH analog in which tryptophan replaced glycine as the sixth amino acid. G. Emons et al., "Growth-inhibitory actions of analogues of luteinizing hormone releasing hormone on tumor cells," *Trends in Endocrinology and Metabolism*, vol. 8, pp. 355-362 (1997) discloses that in vitro proliferation of two human ovarian cancer cell lines, and of two human endometrial cancer cell lines, was inhibited by the LHRH agonist triptorelin; and that in vitro proliferation of ovarian and endometrial cancer cell lines was also inhibited by LHRH antagonist Cetrorelix. Antiproliferative effects of LHRH analogs against prostate cancer cell lines and chronic administration of LHRH agonists inhibited ovarian or testicular function in a reversible manner are reported.

M. Kovacs et al., "Recovery of pituitary function after treatment with a targeted cytotoxic analog of luteinizing hormone-releasing hormone," *Proc. Natl. Acad. Sci. USA*, vol. 94, pp. 1420-1425 (1997) discloses a doxorubicin derivative conjugated to the carrier agonist [D-Lys⁶] LHRH to reversibly (i.e., temporarily) inhibit gonadotrophic cells in the pituitary. It was also reported that this LHRH analog-toxin conjugate inhibited growth of prostate tumors in rats.

J. Janovick et al., "Gonadotropin releasing hormone agonist provokes homologous receptor microaggregation: an early event in seven-transmembrane receptor mediated signaling," *Endocrinology*, vol. 137, pp. 3602-3605 (1996) discloses using the agonist D-Lys⁶-GnRH- and the antagonist D-pGlu¹-D-Phe²-D-Trp³-D-Lys⁶-GnRH.

C. Albano et al., "Comparison of different doses of gonadotropin-releasing hormone antagonist Cetrorelix during controlled ovarian hyperstimulation," *Fertility and Sterility*, vol. 67, pp. 917-922 (1997) reports studies with GnRH antagonist Cetrorelix to determine the minimal effective dose to prevent premature LH surge in patients undergoing controlled ovarian hyperstimulation for assisted reproductive technologies.

L. Maclellan et al., "Superstimulation of ovarian follicular growth with FSH, oocyte recovery, and embryo production from Zebu (*Bos indicus*) calves: Effects of Treatment with a GnRH Agonist or Antagonist," *Theriogenology*, vol. 49, pp. 1317-29 (1998) reports studies with GnRH agonist (deslorelin) or GnRH antagonist (cetrorelix) administered to calves.

A. Qayum et al., "The effects of gonadotropin releasing hormone analogues in prostate cancer are mediated through specific tumor receptors," *Br. J. Cancer*, vol. 62, pp. 96-99 (1990) reports the use of GnRH analog buserelin on prostate cancers.

A. Cornea et al., "Redistribution of G$_{q/11}$α in the pituitary gonadotrope in response to a gonadotropin-releasing hormone agonist," *Endocrinology*, vol. 139, pp. 397-402 (1998) reports the effect of buserelin, a metabolically stable GnRH agonist.

In addition to the foregoing, (i) European Patent EP0277829; (ii) Genaro G, Lacerda Neto J C, Rosa e Silva A A, "LH response (in vivo and in vitro) to an LHRH agonist administered to domestic male cats," *Arch Physiol Biochem* 2003; 111(3):254-8; (iii) Horvath J E, Bajo A M, Schally A V, Kovacs M, Herbert F, Groot K, "Effects of long-term treatment with the luteinizing hormone-releasing hormone (LHRH) agonist Decapeptyl and the LHRH antagonist Cetrorelix on the levels of pituitary LHRH receptors and their mRNA expression in rats," *Proc Natl Acad Sci USA* 2002; 99(23):15048-53; (iv) Wu T J, Mani S K, Glucksman M J, Roberts J L, "Stimulation of luteinizing hormone-releasing hormone (LHRH) gene expression in GT1-7 cells by its metabolite, LHRH-(1-5)," *Endocrinology* 2005; 146 (1):280-6.

The following LHRH analogs are available commercially, for example, from Aldrich: Luteinizing hormone releasing hormone human acetate salt; Luteinizing hormone releasing hormone salmon; [D-Ala⁶, N-Me-Leu⁷]-LH-RH; [D-Ala⁶]-LH-RH acetate salt hydrate; [D-His(benzyl)⁶]-LH-RH Fragment 3-9 ethylamide trifluoroacetate salt; [D-His(Bzl)⁶]-

LH-RH Fragment 1-7; [D-His(Bzl)⁶]-LH-RH Fragment 2-9; [D-His(Bzl)⁶]-LH-RH Fragment 4-9 ethylamide trifluoroacetate salt; [D-His(Bzl)⁶]-LH-RH Fragment 5-9 Ethylamide trifluoroacetate salt; [D-Lys⁶]-LH-RH; [D-pGlu¹, D-Phe², D-Trp³ᐧ⁶]-LH-RH; [D-Ser⁴]-LH-RH; [D-Trp⁶]-LH-RH; [D-Trp⁶]-LH-RH-Leu-Arg-Pro-Gly-NH₂; [des-Gly¹⁰, D-Ala⁶]-LH-RH ethylamide acetate salt hydrate; [des-Gly¹⁰, D-His(Bzl)⁶]-LH-RH ethylamide; [des-Gly¹⁰, D-His², D-Trp⁶, Pro⁹]-LH-RH ethylamide trifluoroacetate salt; [des-Gly¹⁰, D-Phe⁶]-LH-RH ethylamide; [des-Gly¹⁰, D-Ser⁴, D-His(Bzl)⁶, Pro⁹]-LH-RH ethylamide acetate salt; [des-Gly¹⁰, D-Ser⁴, D-Trp⁶, Pro⁹]-LH-RH ethylamide trifluoroacetate salt; [des-Gly¹⁰, D-Trp⁶, D-Leu⁷, Pro⁹]-LH-RH ethylamide trifluoroacetate salt; [des-Gly¹⁰, D-Trp⁶]-LH-RH ethylamide; [des-Gly¹⁰, D-Tyr⁵, D-Trp⁶, Pro⁹]-LH-RH ethylamide trifluoroacetate salt; [des-pGlu¹]-LH-RH; [His (3-Methyl)²]-LH-RH; [Hyp⁹]-LH-RH; Formyl-[D-Trp⁶]-LH-RH Fragment 2-10; LH-RH Fragment 1-2; LH-RH Fragment 1-4; Luteinizing hormone releasing hormone Fragment 4-10; Luteinizing hormone releasing hormone Fragment 7-10 dihydrochloride; Buserelin; Leuprolide acetate salt; [D-Trp⁶]-LHRH Fragment, 1-6; and Antide (Ala-Phe-Ala-Ser-Lys-Lys-Leu-Lys-Pro-Ala) (SEQ ID NO:2).

The invention therefore includes modifications and variations, such as substitutions, additions or deletions. Thus, a conjugate or a fusion that includes a peptide sequence can incorporate any number of conservative or non-conservative amino acid substitutions, as long as such substitutions do not destroy activity (binding). Thus, for example, a modified LHRH can retain at least partial LHRH-receptor (LHRHR) binding activity.

A "conservative substitution" is a replacement of one amino acid by a biologically, chemically or structurally similar residue. Biologically similar means that the substitution is compatible with a biological activity, e.g., binding activity. Structurally similar means that the amino acids have side chains with similar length, such as alanine, glycine and serine, or having similar size, or the structure of a first, second or additional domain is maintained. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, etc. Routine assays can be used to determine whether a modification or variation has activity, e.g., binding activity.

The terms "amino acid sequence," "protein," "polypeptide" and "peptide" are used interchangeably herein to refer to two or more amino acids, or "residues," covalently linked by an amide bond or equivalent. Amino acid sequences can be linked by non-natural and non-amide chemical bonds including, for example, those formed with glutaraldehyde, N-hydroxysuccinimide esters, bifunctional maleimides, or N, N'-dicyclohexylcarbodiimide (DCC). Non-amide bonds include, for example, ketomethylene, aminomethylene, olefin, ether, thioether and the like (see, e.g., Spatola in *Chemistry and Biochemistry of Amino Acids, Peptides and Proteins*, Vol. 7, pp 267-357 (1983), "Peptide and Backbone Modifications," Marcel Decker, NY).

Conjugates and fusions include L-amino acid sequences, D-amino acid sequences and amino acid sequences with mixtures of L-amino acids and D-amino acids. Amino acid sequences of first and second domains can be a linear or a cyclic structure, conjugated to a distinct moiety (e.g., third, fourth, fifth, sixth, seventh, etc. domains), form intra or intermolecular disulfide bonds, and also form higher order multimers or oligomers with the same or different amino acid sequence, or other molecules.

Exemplary lengths of conjugates and fusions include from about 5 to 10, 10 to 15, 15 to 20, 20 to 25, 25 to 50, 50 to 100 or more amino acid residues. In particular embodiments, a conjugate or fusion has 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 amino acid residues.

The term "identity" and "homology" and grammatical variations thereof mean that two or more referenced entities are the same. Thus, where two amino acid sequences are identical, they have the same amino acid sequence. "Areas, regions or domains of identity" mean that a portion of two or more referenced entities are the same. Thus, where two amino acid sequences are identical or homologous over one or more sequence regions, they share identity in these regions.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Individual residues and conjugate/fusions can be formed by a covalent or a non-covalent bond. Non-limiting examples of covalent bonds are amide bonds, non-natural and non-amide chemical bonds, which include, for example, glutaraldehyde, N-hydroxysuccinimide esters, bifunctional maleimides, N, N'-dicyclohexylcarbodiimide (DCC) or N,N'-diisopropylcarbodiimide (DIC). Linking groups alternative to amide bonds include, for example, ketomethylene (e.g., —C(=O)—CH₂— for —C(=O)—NH—), aminomethylene (CH₂—NH), ethylene, olefin (CH=CH), ether (CH₂—O), thioether (CH₂—S), tetrazole (CN₄—), thiazole, retroamide, thioamide, or ester (see, e.g., Spatola (1983) in *Chemistry and Biochemistry of Amino Acids, Peptides and Proteins*, Vol. 7, pp 267-357, "Peptide and Backbone Modifications," Marcel Decker, NY).

The two or more molecular entities can be joined directly or separated by an intervening region, such as a hinge, spacer or linker positioned between the molecular entities. In one embodiment, two or more molecular entities are joined by an amino acid, peptide or a non-peptide hinge, spacer or linker. Peptide hinge, spacer or linker sequences can be any length, but typically range from about 1-5, 5-10, 10-15, 10-20, 20-25 or 25-30 amino acid residues. In particular embodiments, a peptide hinge, spacer or linker positioned between a first and second domain is from 1 to 25 L- or D-amino acid residues, or 1 to 6 L- or D-amino acid residues. Particular amino acid residues that are included in sequences positioned between two or more molecular entities include one or more of or C, A, S or G amino acid residues. Specific non-limiting examples of peptides positioned between the two or more molecular entities include a sequence within or set forth as: GSGGS (SEQ ID NO:3), ASAAS (SEQ ID NO:4), or CCCCCC (SEQ ID NO:5).

In another embodiment, two or more molecular entities are joined by a carbon chain, which can be denoted as $C_1$, $C_2$, $C_3$, $C_4$, $C_4$, $C_5$, $C_6$, etc., where the subscript denotes the number of carbons in the chain. Multi-carbon chains include carboxylic acids (e.g., dicarboxylic acids) such as glutaric acid, succinic acid and adipic acid.

Derivatives of amino acids and peptides can be positioned between the two or more molecular entities. A specific non-limiting example of an amino acid derivative is a lysine derivative, or a 6 carbon linker such as α-amino-caproic acid.

Conjugates and fusions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure. Conjugates and fusions include cyclic structures such as an end-to-end amide bond between the amino and carboxy-terminus of the molecule or intra- or inter-molecular disulfide bond(s). Conjugates and fusions may be modified in vitro or in vivo, e.g., post-translationally modified to include, for example, sugar or carbohydrate residues, phosphate groups, fatty acids, lipids, etc.

Amino acid sequences, proteins, polypeptides, peptides and peptidomimetics can be produced and isolated using methods known in the art. Peptides can be synthesized, whole or in part, using chemical methods known in the art (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid-phase techniques (see, e.g., Roberge *Science* 269:202 (1995); Merrifield, *Methods Enzymol.* 289:3(1997)) and automated synthesis may be achieved, e.g., using the ABI 431A Peptide Synthesizer (Perkin Elmer) in accordance with the manufacturer's instructions. Peptides and peptide mimetics can also be synthesized using combinatorial methodologies. Synthetic residues and polypeptides incorporating mimetics can be synthesized using a variety of procedures and methodologies known in the art (see, e.g., *Organic Syntheses* Collective Volumes, Gilman, et al. (Eds) John Wiley & Sons, Inc., NY). Modified peptides can be produced by chemical modification methods (see, for example, Belousov, *Nucleic Acids Res.* 25:3440 (1997); Frenkel, *Free Radic. Biol. Med.* 19:373 (1995); and Blommers, *Biochemistry* 33:7886 (1994).

Conjugates and fusions include isolated and purified forms. The term "isolated," when used as a modifier of an invention composition, means that the composition is made by the hand of man or is separated, substantially completely or at least in part, from the naturally occurring in vivo environment. Generally, an isolated composition is substantially free of one or more materials with which it normally associates with in nature, for example, one or more protein, nucleic acid, lipid, carbohydrate, cell membrane. The term "isolated" does not exclude alternative physical forms of the composition, such as multimers/oligomers, variants, modifications or derivatized forms, or forms expressed in host cells produced by the hand of man. The term "isolated" also does not exclude forms (e.g., pharmaceutical formulations and combinations of conjugates and fusions with each other or with other compositions) in which there are combinations therein, any one of which is produced by the hand of man.

An "isolated" composition can also be "purified" when free of some, a substantial number of, most or all of the materials with which it typically associates with in nature. Thus, an isolated conjugate or fusion that also is substantially pure does not include polypeptides or polynucleotides present among millions of other sequences, such as proteins of a protein library or nucleic acids in a genomic or cDNA library, for example. A "purified" composition can be combined with one or more other molecules.

In accordance with the invention, there are provided conjugate or fusion mixtures in combination compositions. In one embodiment, a mixture includes one or more conjugates or fusions and an anti-cell proliferative, anti-tumor, anti-cancer, or anti-neoplastic treatment or agent. Representative non-limiting combinations include gemcitabine, such as LHRH-Curcumin and gemcitabine. In another embodiment, a mixture includes a pharmaceutically acceptable carrier or excipient. Other non-limiting examples of combinations include one or more conjugates or fusions with one or more of an anti-cell proliferative, anti-tumor, anti-cancer, or anti-neoplastic treatment or agent, and in a pharmaceutically acceptable carrier or excipient.

Conjugates and fusions of the invention can be used to target cells for lysis, cell death or apoptosis. Such cells can be selectively targeted. For example a cell that expresses a receptor, can be targeted by a conjugate/fusion and thereby be preferentially killed compared to cells that do not detectably express, or express less of, the receptor.

In accordance with the invention, there are provided methods of reducing or inhibiting proliferation of a cell, and methods of reducing or inhibiting cell proliferation. In one embodiment, a method includes contacting a cell with a conjugate or fusion in an amount sufficient to reduce or inhibit proliferation of the cell. In another embodiment, a method includes contacting a cell with a conjugate or fusion in an amount sufficient to reduce or inhibit cell proliferation.

Also provided are methods of reducing or inhibiting proliferation of a hyperproliferative cell, and methods of reducing or inhibiting proliferation of hyperproliferating cells. In one embodiment, a method includes contacting a hyperproliferative cell or hyperproliferating cells with a conjugate or fusion in an amount sufficient to reduce or inhibit proliferation.

Further provided are methods of reducing or inhibiting proliferation of a non-metastatic or metastatic neoplastic, cancer, tumor and malignant cell. In one embodiment, a method includes contacting a neoplastic, cancer, tumor or malignant cell with a conjugate or fusion in an amount sufficient to reduce or inhibit proliferation of the cell.

Additionally provided are methods of selectively reducing or inhibiting proliferation of a cell (e.g., a hyperproliferating cell) that expresses a receptor, e.g., LHRHR. In one embodiment, a method includes contacting the cell with a conjugate or fusion in an amount sufficient to reduce or inhibit proliferation of the cell (e.g., hyperproliferating cell), wherein the conjugate or fusion binds to the receptor, e.g., LHRHR, expressed by the cell.

The term "contacting" means direct or indirect binding or interaction between two or more entities (e.g., between a conjugate or fusion and a cell). Contacting as used herein includes in solution, in solid phase, in vitro, ex vivo, in a cell and in vivo. Contacting in vivo can be referred to as administering, or administration.

Target cells include cells that express a receptor that binds to LHRH and/or LHRH analogs. Examples include luteinizing hormone releasing hormone receptor.

Conjugates and fusions and methods of the invention are also applicable to treating undesirable or aberrant cell proliferation and hyperproliferative disorders. Thus, in accordance with the invention, methods of treating undesirable or aberrant cell proliferation and hyperproliferative disorders are provided. In one embodiment, a method includes administering to a subject (in need of treatment) an amount of a conjugate or fusion sufficient to treat the undesirable or aberrant cell proliferation or the hyperproliferative disorder.

The term "hyperproliferative disorder" refers to any undesirable or aberrant cell survival (e.g., failure to undergo programmed cell death or apoptosis), growth or proliferation. Such disorders include benign hyperplasias, non-metastatic and metastatic neoplasias, cancers, tumors and malignancies. Undesirable or aberrant cell proliferation and hyperproliferative disorders can affect any cell, tissue, organ in a subject. Undesirable or aberrant cell proliferation and hyperproliferative disorders can be present in a subject, locally, regionally or systemically. A hyperproliferative disorder can arise from a multitude of tissues and organs, including but not limited to breast, lung (e.g., small cell or non-small cell), thyroid, head and neck, brain, nasopharynx, throat, nose or sinuses, lymphoid, adrenal gland, pituitary gland, thyroid, lymph, gastrointestinal (mouth, esophagus, stomach, duodenum, ileum, jejunum (small intestine), colon, rectum), genito-urinary tract (uterus, ovary, vagina cervix, endometrium, fallopian tube, bladder, testicle, penis, prostate), kidney, pancreas, liver, bone, bone marrow, lymph, blood, muscle, skin, and stem cells, which may or may not metastasize to other secondary sites, regions or locations.

Conjugates and fusions and methods of the invention are also applicable to metastatic or non-metastatic tumor, cancer, malignancy or neoplasia of any cell, organ or tissue origin. Such disorders can affect virtually any cell or tissue type, e.g., carcinoma, sarcoma, melanoma, neural, and reticuloendothelial or haematopoietic neoplastic disorders (e.g., myeloma, lymphoma or leukemia).

The terms "neoplasia" and "tumor" refer to a cell or population of cells whose growth, proliferation or survival is greater than growth, proliferation or survival of a normal counterpart cell, e.g. a cell proliferative or differentiative disorder. A tumor is a neoplasia that has formed a distinct mass or growth. A "cancer" or "malignancy" refers to a neoplasia or tumor that can invade adjacent spaces, tissues or organs. A "metastasis" refers to a neoplasia, tumor, cancer or malignancy that has disseminated or spread from its primary site to one or more secondary sites, locations or regions within the subject, in which the sites, locations or regions are distinct from the primary tumor or cancer.

Neoplastic, tumor, cancer and malignant cells (metastatic or non-metastatic) include dormant or residual neoplastic, tumor, cancer and malignant cells. Such cells typically consist of remnant tumor cells that are not dividing (G0-G1 arrest). These cells can persist in a primary site or as disseminated neoplastic, tumor, cancer or malignant cells as a minimal residual disease. These dormant neoplastic, tumor, cancer or malignant cells remain unsymptomatic, but can develop severe symptoms and death once these cells proliferate. Invention Conjugates and fusions and methods can be used to reduce or inhibit proliferation of dormant neoplastic, tumor, cancer or malignant cells, which can in turn inhibit or reduce tumor or cancer relapse, or tumor or cancer metastasis or progression.

In accordance with the invention, methods of treating a subject having a metastatic or non-metastatic tumor, cancer, malignancy or neoplasia are provided. In one embodiment, a method includes administering to a subject (in need of treatment) an amount of a conjugate or fusion sufficient to treat (e.g., reduce or inhibit proliferation) the metastatic or non-metastatic tumor, cancer, malignancy or neoplasia.

The metastatic or non-metastatic tumor, cancer, malignancy or neoplasia may be in any stage, e.g., early or advanced, such as a stage I, II, III, IV or V tumor. The metastatic or non-metastatic tumor, cancer, malignancy or neoplasia may have been subject to a prior treatment or be stabilized (non-progressing) or in remission.

In terms of metastasis, invention conjugates, fusions and methods can be used to reduce or inhibit metastasis of a primary tumor or cancer to other sites, or the formation or establishment of metastatic tumors or cancers at other sites distal from the primary tumor or cancer thereby inhibiting or reducing tumor or cancer relapse or tumor or cancer progression. Thus, conjugates, fusions methods of the invention include, among other things, 1) reducing or inhibiting growth, proliferation, mobility or invasiveness of tumor or cancer cells that potentially or do develop metastases (e.g., disseminated tumor cells, DTC); 2) reducing or inhibiting formation or establishment of metastases arising from a primary tumor or cancer to one or more other sites, locations or regions distinct from the primary tumor or cancer; 3) reducing or inhibiting growth or proliferation of a metastasis at one or more other sites, locations or regions distinct from the primary tumor or cancer after a metastasis has formed or has been established; and 4) reducing or inhibiting formation or establishment of additional metastasis after the metastasis has been formed or established.

Cells of a metastatic or non-metastatic tumor, cancer, malignancy or neoplasia may be aggregated in a "solid" cell mass or be dispersed or diffused. A "solid" tumor refers to cancer, neoplasia or metastasis that typically aggregates together and forms a mass. Specific non-limiting examples include visceral tumors such as melanomas, breast, pancreatic, uterine and ovarian cancers, testicular cancer, including seminomas, gastric or colon cancer, hepatomas, adrenal, renal and bladder carcinomas, lung, head and neck cancers and brain tumors/cancers.

Carcinomas, which refer to malignancies of epithelial or endocrine tissue, include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the uterus, cervix, lung, prostate, breast, head and neck, colon, pancreas, testes, adrenal, kidney, esophagus, stomach, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma and oligodendrocytoma.

A "liquid tumor," which refers to neoplasia that is dispersed or is diffuse in nature, as they do not typically form a solid mass. Particular examples include neoplasia of the reticuloendothelial or hematopoieticsystem, such as lymphomas, myelomas and leukemias. Non-limiting examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML). Lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic lymphoma (LGF), Hodgkin's disease and Reed-Sternberg disease.

Any composition, treatment, protocol, therapy or regimen having an anti-cell proliferative activity or effect can be combined with a conjugate/fusion or used in combination in a method of the invention. Conjugates, fusions and methods of the invention therefore include anti-cell proliferative, anti-tumor, anti-cancer, anti-neoplastic and anti-metastatic treatments, protocols and therapies, which include any other composition, treatment, protocol or therapeutic regimen that inhibits, decreases, retards, slows, reduces or prevents a hyperproliferative disorder, such as tumor, cancer, malignant or neoplastic growth, progression, metastasis, proliferation or survival, or worsening in vitro or in vivo. Particular non-limiting examples of an anti-cell proliferative (e.g., tumor) therapy include chemotherapy, immunotherapy, radiotherapy (ionizing or chemical), local thermal (hyperthermia) therapy, surgical resection and vaccination. A conjugate or fusion can be administered prior to, substantially contemporaneously with or following administration of the anti-cell proliferative, anti-neoplastic, anti-tumor, anti-cancer, anti-metastatic or immune-enhancing treatment or therapy. A conjugate or fusion can be administered as a combination compositions with the anti-cell proliferative, anti-neoplastic, anti-tumor, anti-cancer, anti-metastatic or immune-enhancing treatment or therapy, metastatic or non-metastatic tumor, cancer, malignancy or neoplasia.

Anti-cell proliferative, anti-neoplastic, anti-tumor, anti-cancer and anti-metastatic compositions, therapies, protocols or treatments include those that prevent, disrupt, interrupt, inhibit or delay cell cycle progression or cell proliferation; stimulate or enhance apoptosis or cell death, inhibit nucleic acid or protein synthesis or metabolism, inhibit cell division, or decrease, reduce or inhibit cell survival, or production or utilization of a necessary cell survival factor, growth factor or signaling pathway (extracellular or intracellular). Non-limiting examples of chemical agent classes having anti-cell proliferative, anti-neoplastic, anti-tumor, anti-cancer and anti-metastatic activities include alkylating agents, anti-metabolites, plant extracts, plant alkaloids, nitrosoureas, hormones, nucleoside and nucleotide analogues.

Conjugates, fusions and methods of the invention, such as treatment methods, can provide a detectable or measurable therapeutic benefit or improvement to a subject. A therapeutic benefit or improvement is any measurable or detectable, objective or subjective, transient, temporary, or longer-term benefit to the subject or improvement in the condition, disorder or disease, an adverse symptom, consequence or underlying cause, of any degree, in a tissue, organ, cell or cell population of the subject. Therapeutic benefits and improvements include, but are not limited to, reducing or decreasing occurrence, frequency, severity, progression, or duration of one or more symptoms or complications associated with a disorder, disease or condition, or an underlying cause or consequential effect of the disorder, disease or condition. Conjugates, fusions and methods of the invention therefore include providing a therapeutic benefit or improvement to a subject.

In a method of the invention in which a therapeutic benefit or improvement is a desired outcome, a conjugate/fusion can be administered in a sufficient or effective amount to a subject in need thereof. An "amount sufficient" or "amount effective" refers to an amount that is expected to provide, in single or multiple doses, typically in combination with one or more other compositions (therapeutic agents such as a chemotherapeutic or immune stimulating drug), treatments, protocols, or therapeutic regimens agents, a detectable response of any duration of time (long or short term), a desired outcome in or a benefit to a subject of any measurable or detectable degree or for any duration of time (e.g., for hours, days, months, years, or cured). The doses or "sufficient amount" or "effective amount" for treatment (e.g., to provide a therapeutic benefit or improvement) typically are expected to be effective to ameliorate a disorder, disease or condition, or one, multiple or all adverse symptoms, consequences or complications of the disorder, disease or condition, to a measurable extent, although reducing or inhibiting a progression or worsening of the disorder, disease or condition or a symptom, is considered a satisfactory outcome.

The term "ameliorate" means a detectable objective or subjective improvement in a subject's condition. A detectable improvement includes a subjective or objective reduction in the occurrence, frequency, severity, progression, or duration of a symptom caused by or associated with a disorder, disease or condition, an improvement in an underlying cause or a consequence of the disorder, disease or condition, or a reversal of the disorder, disease or condition.

Treatment can therefore result in inhibiting, reducing or preventing a disorder, disease or condition, or an associated symptom or consequence, or underlying cause; inhibiting, reducing or preventing a progression or worsening of a disorder, disease, condition, symptom or consequence, or underlying cause; or further deterioration or occurrence of one or more additional symptoms of the disorder, disease condition, or symptom. Thus, a successful treatment outcome leads to a "therapeutic effect," or "benefit" or inhibiting, reducing or preventing the occurrence, frequency, severity, progression, or duration of one or more symptoms or underlying causes or consequences of a condition, disorder, disease or symptom in the subject. Treatment methods affecting one or more underlying causes of the condition, disorder, disease or symptom are therefore considered to be beneficial. Stabilizing or inhibiting progression or worsening of a disorder or condition is also a successful treatment outcome.

A therapeutic benefit or improvement need not be complete ablation of any one, most or all symptoms, complications, consequences or underlying causes associated with the condition, disorder or disease. Thus, a satisfactory endpoint is achieved when there is an incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of one or more of the physiological, biochemical or cellular manifestations or characteristics of the disorder or disease, over a short or long duration of time (hours, days, weeks, months, etc.).

In particular embodiments, a method of treatment results in partial or complete destruction of a metastatic or non-metastatic tumor, cancer, malignant or neoplastic cell mass, volume, size or numbers of cells; results in stimulating, inducing or increasing metastatic or non-metastatic tumor, cancer, malignant or neoplastic cell necrosis, lysis or apoptosis; results in reducing metastatic or non-metastatic tumor, cancer, malignant or neoplastic volume, size, cell mass; results in inhibiting or preventing progression or an increase in metastatic or non-metastatic tumor, cancer, malignant or neoplastic volume, mass, size or cell numbers; results in inhibiting or decreasing the spread or dissemination of hyperproliferating cells (e.g., metastasis) to other (secondary) sites, regions, tissues or organs in a subject, or establishment of hyperproliferating cells (e.g., metastasis) at other (secondary) sites, regions, tissues or organs in a subject; or results in prolonging lifespan of the subject. In additional particular embodiments, a method of treatment results in reducing or decreasing severity, duration or frequency of an adverse symptom or complication associated with or caused by the metastatic or non-metastatic tumor, cancer, malignancy or neoplasia.

An amount sufficient or an amount effective can but need not be provided in a single administration and, can but need not be, administered in combination with another composition (e.g., chemotherapeutic or agent), treatment, protocol or therapeutic regimen. For example, the amount may be proportionally increased as indicated by the need of the subject, status of the disorder, disease or condition treated or the side effects of treatment. In addition, an amount sufficient or an amount effective need not be sufficient or effective if given in single or multiple doses without a second composition (e.g., chemotherapeutic agent), treatment, protocol or therapeutic regimen, since additional doses, amounts or duration above and beyond such doses, or additional compositions (e.g., chemotherapeutic agents), treatments, protocols or therapeutic regimens may be included in order to be considered effective or sufficient in a given subject. Amounts considered sufficient also include amounts that result in a reduction of the use of another treatment, therapeutic regimen or protocol.

An amount sufficient or an amount effective need not be effective in each and every subject treated, prophylactically or therapeutically, nor a majority of treated subjects in a given group or population. As is typical for treatment or therapeutic methods, some subjects will exhibit greater or less response to a given treatment, therapeutic regimen or protocol. An amount sufficient or an amount effective refers to sufficiency or effectiveness in a particular subject, not a group or the general population. Such amounts will depend in part upon the condition treated, such as the type or stage of undesirable or aberrant cell proliferation or hyperproliferative disorder (e.g., a metastatic or non-metastatic tumor, cancer, malignancy or neoplasia), the therapeutic effect desired, as well as the individual subject (e.g., the bioavailability within the subject, gender, age, etc.).

Particular non-limiting examples of therapeutic benefit or improvement for undesirable or aberrant cell proliferation, such as a hyperproliferative disorder (e.g., a metastatic or non-metastatic tumor, cancer, malignancy or neoplasia) include a reduction in cell size, mass or volume, inhibiting an increase in cell size, mass or volume, a slowing or inhibition of worsening or progression, stimulating cell necrosis, lysis or apoptosis, reducing or inhibiting neoplastic or tumor malignancy or metastasis, reducing mortality, and prolonging lifespan of a subject. Thus, inhibiting or delaying an increase in cell size, mass, volume or metastasis (stabilization) can increase lifespan (reduce mortality) even if only for a few days, weeks or months, even though complete ablation of the metastatic or non-metastatic tumor, cancer, malignancy or neoplasia has not occurred. Adverse symptoms and complications associated with a hyperproliferative disorder (e.g., a metastatic or non-metastatic tumor, cancer, malignancy or neoplasia) that can be reduced or decreased include, for example, pain, nausea, discomfort, lack of appetite, lethargy and weakness. A reduction in the occurrence, frequency, severity, progression, or duration of a symptom of undesirable or aberrant cell proliferation, such as a hyperproliferative disorder (e.g., a metastatic or non-metastatic tumor, cancer, malignancy or neoplasia), such as an improvement in subjective feeling (e.g., increased energy, appetite, reduced nausea, improved mobility or psychological well being, etc.), are therefore all examples of therapeutic benefit or improvement.

For example, a sufficient or effective amount of a conjugate or fusion is considered as having a therapeutic effect if administration results in less chemotherapeutic drug, radiation or immunotherapy being required for treatment of undesirable or aberrant cell proliferation, such as a hyperproliferative disorder (e.g., a metastatic or non-metastatic tumor, cancer, malignancy or neoplasia).

The term "subject" refers to animals, typically mammalian animals, such as humans, non human primates (apes, gibbons, chimpanzees, orangutans, macaques), domestic animals (dogs and cats), farm animals (horses, cows, goats, sheep, pigs) and experimental animal (mouse, rat, rabbit, guinea pig). Subjects include animal disease models, for example, animal models of undesirable or aberrant cell proliferation, such as a hyperproliferative disorder (e.g., a metastatic or non-metastatic tumor, cancer, malignancy or neoplasia) for analysis of conjugates and fusions in vivo.

Subjects appropriate for treatment include those having or at risk of having a metastatic or non-metastatic tumor, cancer, malignant or neoplastic cell, those undergoing as well as those who are undergoing or have undergone anti-cell proliferative (e.g., metastatic or non-metastatic tumor, cancer, malignancy or neoplasia) therapy, including subjects where the tumor is in remission. "At risk" subjects typically have risk factors associated with undesirable or aberrant cell proliferation, development of hyperplasia (e.g., a tumor).

Particular examples of at risk or candidate subjects include those with cells that express a receptor, ligand, antigen or antibody to which a conjugate or fusion can bind, particularly where cells targeted for necrosis, lysis, killing or destruction express greater numbers or amounts of receptor, ligand, antigen or antibody than non-target cells. Such cells can be selectively or preferentially targeted for necrosis, lysis or killing.

At risk subjects also include those that are candidates for and those that have undergone surgical resection, chemotherapy, immunotherapy, ionizing or chemical radiotherapy, local or regional thermal (hyperthermia) therapy, or vaccination. The invention is therefore applicable to treating a subject who is at risk of a metastatic or non-metastatic tumor, cancer, malignancy or neoplasia or a complication associated with a metastatic or non-metastatic tumor, cancer, malignancy or neoplasia, for example, due to metastatic or non-metastatic tumor, cancer, malignancy or neoplasia reappearance or regrowth following a period of stability or remission.

Risk factors include gender, lifestyle (diet, smoking), occupation (medical and clinical personnel, agricultural and livestock workers), environmental factors (carcinogen exposure), family history (autoimmune disorders, diabetes, etc.), genetic predisposition, etc. For example, subjects at risk for developing melanoma include excess sun exposure (ultraviolet radiation), fair skin, high numbers of naevi (dysplastic nevus), patient phenotype, family history, or a history of a previous melanoma. Subjects at risk for developing cancer can therefore be identified by lifestyle, occupation, environmental factors, family history, and genetic screens for tumor associated genes, gene deletions or gene mutations. Subjects at risk for developing breast cancer lack Brca1, for example. Subjects at risk for developing colon cancer have early age or high frequency polyp formation, or deleted or mutated tumor suppressor genes, such as adenomatous polyposis coli (APC), for example.

Subjects also include those precluded from other treatments. For example, certain subjects may not be good candidates for surgical resection, chemotherapy, immunotherapy, ionizing or chemical radiotherapy, local or regional thermal (hyperthermia) therapy, or vaccination. Thus, candidate subjects for treatment in accordance with the invention include those that are not a candidate for surgical resection, chemotherapy, immunotherapy, ionizing or chemical radiotherapy, local or regional thermal (hyperthermia) therapy, or vaccination.

Conjugates and fusions may be formulated in a unit dose or unit dosage form. In a particular embodiment, a fusion is in an amount effective to treat a subject having undesirable or aberrant cell proliferation or a hyperproliferative disorder, in combination with an anti-cell proliferative drug (e.g., gemcitabine). In an additional particular embodiment, a conjugate or fusion is in an amount effective to treat a subject having a metastatic or non-metastatic tumor, cancer, malignancy or neoplasia, in combination with an anti-cell proliferative drug (e.g., gemcitabine). Exemplary unit doses of conjugates and fusions (e.g., LHRH-Curcumin, LHRH-Curcumin analog, LHRH analog-Curcumin and LHRH analog-Curcumin analog) and/or anti-cell proliferative drugs (e.g., gemcitabine) range from about 25-250, 250-500, 500-1000, 1000-2500 or 2500-5000, 5000-25,000, 5000-50,000 ng; and from about 25-250, 250-500, 500-1000, 1000-2500 or 2500-5000, 5000-25,000, 5000-50,000 µg.

Compositions and methods of the invention may be contacted or provided in vitro, ex vivo or in vivo. Compositions can be administered to provide the intended effect as a single or multiple dosages, for example, in an effective or sufficient amount. Exemplary doses of conjugates/fusions and/or anti-cell proliferative drugs (e.g., gemcitabine) range from about 25-250, 250-500, 500-1000, 1000-2500 or 2500-5000, 5000-25,000, 5000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 5000-50,000 µg/kg, on the same day, consecutive days, or alternating days or intermittently. Single or multiple doses can be administered on the same day, consecutive days, alternating days or intermittently.

Compositions can be administered and methods may be practiced via systemic, regional or local administration, by any route. For example, a conjugate or fusion can be administered systemically, regionally or locally, intravenously, orally (e.g., ingestion or inhalation), intramuscularly, intraperitoneally, intradermally, subcutaneously, intracavity, intracranially, transdermally (topical), parenterally, e.g. transmucosally or rectally. Compositions and methods of the invention including pharmaceutical formulations can be administered via a (micro)encapsulated delivery system or packaged into an implant for administration.

The invention further provides a conjugate or fusion and methods wherein the conjugate or fusion is included in pharmaceutical compositions. A pharmaceutical composition refers to "pharmaceutically acceptable" and "physiologically acceptable" carriers, diluents or excipients. As used herein, the term "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration and with the other components of the formulation. Such formulations can be contained in a tablet (coated or uncoated), capsule (hard or soft), microbead, emulsion, powder, granule, crystal, suspension, syrup or elixir.

Pharmaceutical compositions can be formulated to be compatible with a particular route of administration. Compositions for parenteral, intradermal, or subcutaneous administration can include a sterile diluent, such as water, saline solution, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose).

Pharmaceutical compositions for injection include sterile (e.g., aqueous) solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyetheylene glycol), and suitable mixtures thereof. Fluidity can be maintained, for example, by the use of a coating such as lecithin, or by the use of surfactants. Antibacterial and antifungal agents include, for example, parabens, chlorobutanol, phenol, ascorbic acid and thimerosal. Including an agent that delays absorption, for example, aluminum monostearate and gelatin can prolonged absorption of injectable compositions.

A conjugate or fusion in accordance with the invention may be formulated into a pharmaceutically acceptable salt. Salts include, without limitation, acid addition salts formed with inorganic acids, for example hydrochloric or phosphoric acid, or organic acids such as acetic, oxalic or tartaric acid, for example. Salts also include those formed from inorganic bases such as, for example, sodium, potassium, ammonium, calcium or ferric hydroxides, and organic bases such as isopropylamine, trimethylamine, histidine, procaine, etc.

Additional pharmaceutical formulations and delivery systems are known in the art and are applicable in the methods of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky, et al., *Drug Delivery Systems*, R. L. Juliano, ed., Oxford, N.Y. (1980), pp. 253-315).

The invention provides kits including a conjugates and fusions of the invention, combination compositions and pharmaceutical formulations thereof, packaged into suitable packaging material. A kit optionally includes a label or packaging insert including a description of the components or instructions for use in vitro, in vivo, or ex vivo, of the components therein. Exemplary instructions include instructions for reducing or inhibiting proliferation of a cell, reducing or inhibiting proliferation of undesirable or aberrant cells, such as a hyperproliferating cell, reducing or inhibiting proliferation of a metastatic or non-metastatic tumor, cancer, malignant or neoplastic cell, treating a subject having a hyperproliferative disorder, treating a subject having a metastatic or non-metastatic tumor, cancer, malignancy or neoplasia.

A kit can contain a collection of such components, e.g., a conjugate or fusion and an anti-cell proliferative drug (e.g., gemcitabine), or two or more conjugates and fusions alone, or in combination with another therapeutically useful composition (e.g., an anti-cell proliferative drug).

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Exemplary instructions include, instructions for treating an undesirable or aberrant cell proliferation, hyperproliferating cells and disorders (e.g., metastatic or non-metastatic tumor, cancer, malignancy or neoplasia). Kits of the invention therefore can additionally include labels or instructions for practicing any of the methods of the invention described herein including treatment methods.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include other components. Each component of the kit can be enclosed within an individual container and all of the various containers can be within a single package. Invention kits can be designed for sterile, stable and/or cold storage. The cells in the kit can be maintained under appropriate storage conditions until used.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a conjugate" or "a fusion" or "an anti-cell proliferative drug" includes a plurality of such conjugates, fusions or anti-cell proliferative drugs, and so forth.

As used herein, all numerical values or numerical ranges include integers within such ranges and fractions of the values or the integers within ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

The following examples describe data showing that LHRH-curcumin conjugate is an attractive candidate for combination therapy. Three dimensional (3D) high throughput assay platform (IncuCyte ZOOM—Essen BioScience) showed that LHRH-curcumin is more effective at the same concentrations than curcumin in pancreatic cancer cell lines expressing LHRHR. LHRH-curcumin together with gemcitabine was shown to be substantially more effective at slowing growth of 3D pancreatic cancer cell spheroids than either compound administered alone.

LHRH-curcumin conjugate as a combination therapy is attractive because of lower toxicity and higher tumor growth inhibition. The data also show that LHRH-curcumin conjugate interacts with the LHRH receptor, although it appears that little of the receptor is at the cell surface. The data further show that LHRH-curcumin conjugate may be cleaved and that both moieties may act independently.

Example 1

This example includes data showing that LHRH-curcumin conjugate is more effective than curcumin alone against Panc-1 cells spheroids growth.

A protocol that enables the growth of identical size single cancer cell spheroids in Matrigel in 96 well plates has been developed. 3D culture approaches are often superior to 2D approaches in predicting efficacy of cancer drugs in human patients.

Figure 1B:
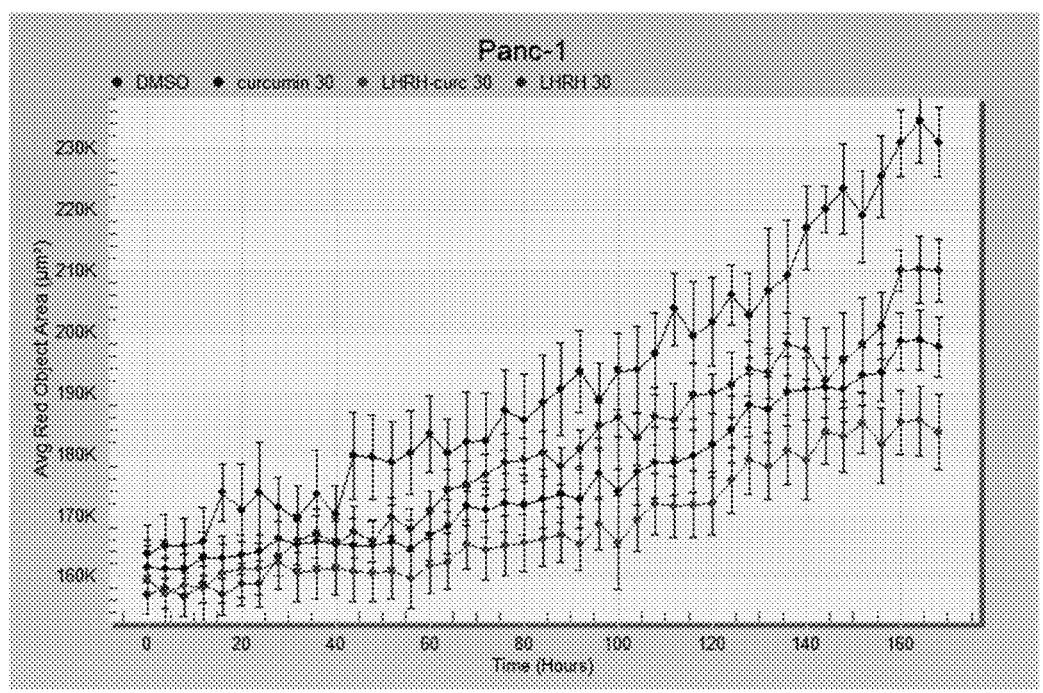

Panc-1 and Mia-Paca-2 cells were grown in 10% FBS DMEM. Cells were collected after trypsinization and resuspended in phenol-red free DMEM with 10% FBS. Cells were labeled with CellTracker Red (Life Technologies) for 5 minutes. After labeling cells were washed with PBS and transfer into 96-well Corning 7007 ULA round bottom plates at 1,000 cells/well in 100 µl phenol-red free media with 10% FBS and 5% Matrigel. After the spheroids were established (24 hours later) the following treatments were applied (8 spheroids per group): (1) LHRH-curcumin conjugate (10 µM, 20 µM and 30 µM); (2) curcumin (10 µM, 20 µM and 30 µM) and (3) DMSO control. Spheroids were grown at 37° C. and 5% CO2 in IncuCyte ZOOM (Essen Bioscience). Images were acquired every 4 h for a period of 120 h post-treatment and software analysis was design to identify the red object in the well. The data were expressed as fold increase in spheroids size at the end of the treatment using the "average red object area in the well" as determined by the IncuCyte software analysis. Reproducibility was confirmed in three independent experiments. Spheroids grew at a uniform rate (FIG. 1).

Figure 2A:
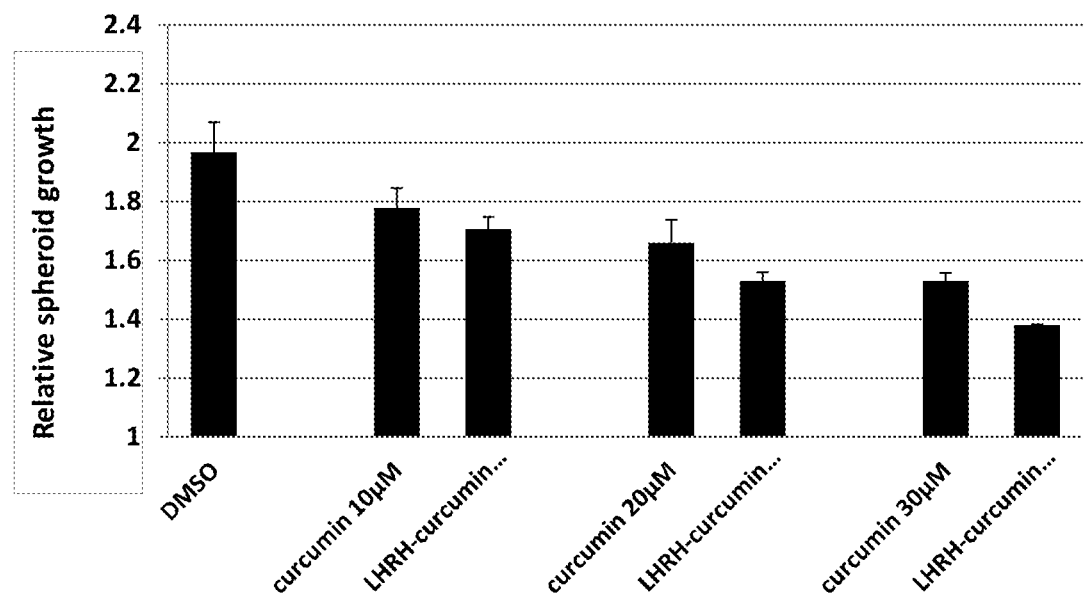
FIG. 2A shows Panc-1 spheroids growth following dose-dependent (10 µM, 20 µM and 30 µM) treatment with LHRH-curcumin, curcumin alone or DMSO control.
Figure 2B:
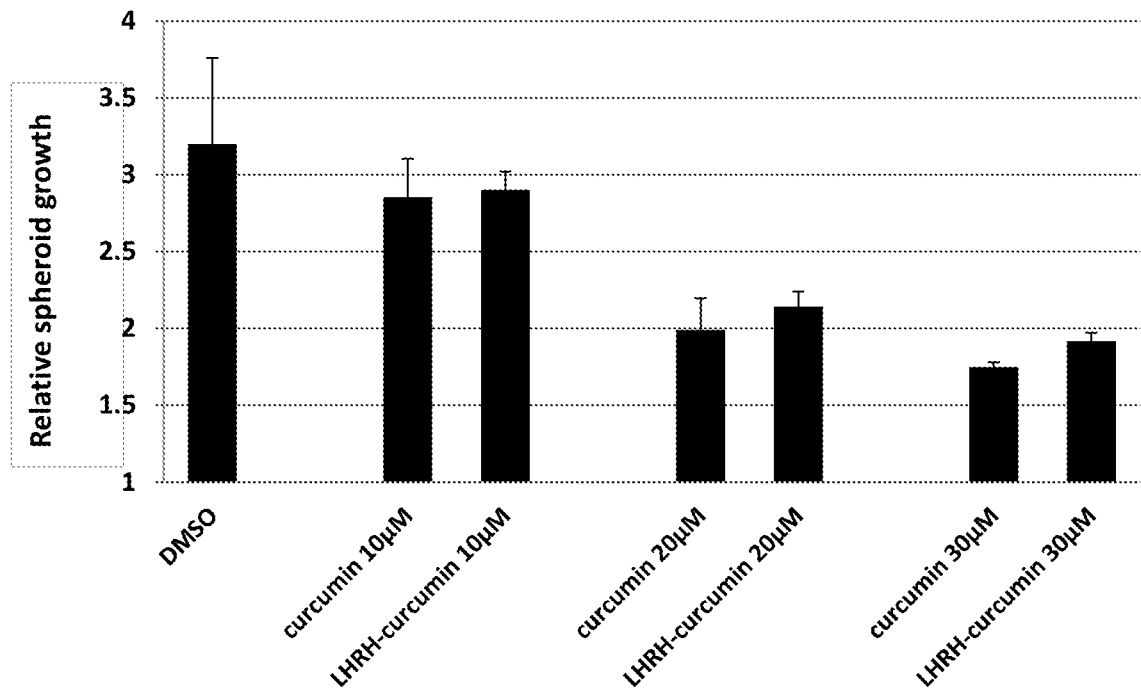
FIG. 2B shows Mia-PaCa-2 spheroids growth following dose-dependent (10 µM, 20 µM and 30 µM) treatment with LHRH-curcumin, curcumin alone or DMSO control.

Treatment with LHRH-curcumin conjugate significantly decreased the size of the spheroids formed by Panc-1 cells in a dose-dependent manner. Moreover, LHRH-curcumin conjugate is more effective than curcumin in Panc-1 pancreatic cancer cell lines growing in 3D culture. Results are shown in FIG. 2A. Interestingly, LHRH-curcumin conjugate is more efficient on Panc-1 cells than Mia-PaCa-2 cells, suggesting that LHRH-receptor (LHRHR) expression is a determinant factor in the efficacy of LHRH-curcumin conjugate treatment. Results are presented in FIG. 2B.

Example 2

This example includes data showing that LHRH treatment has an inhibitory effect on Panc-1 cells spheroids growth.

Figure 3:
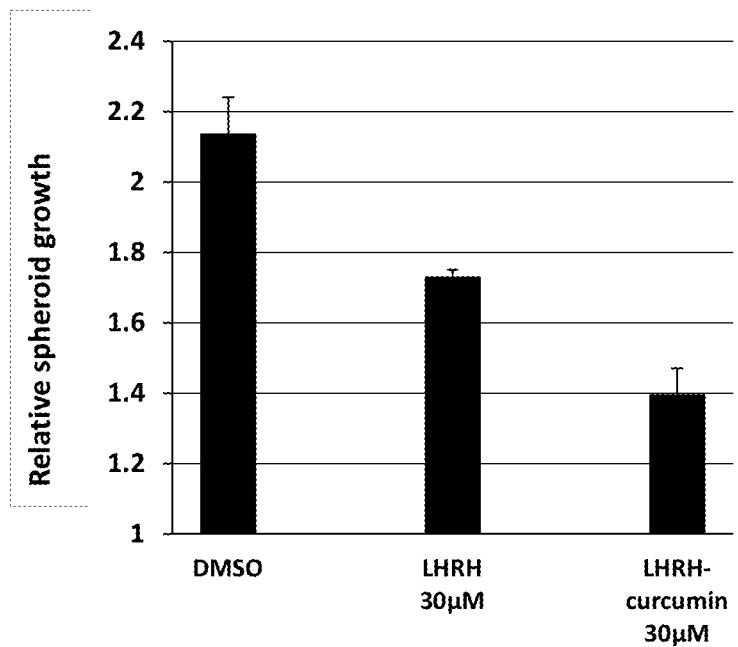
FIG. 3 shows Panc-1 spheroids growth following treatment with LHRH alone (30 µM) or LHRH-curcumin (30 µM). DMSO was used as control.

To verify that the effect of LHRH-curcumin conjugate was associated with binding to cell-surface LHRH receptor, Panc-1 spheroides were treated with free LHRH and spheroids growth measured. Free LHRH has an inhibitory effect on spheroids growth consistent with the presence of LHRHR at the cell surface. Moreover, the effect of LHRH-curcumin conjugate was superior to that of LHRH. Results are shown in FIG. 3. Reproducibility was confirmed in three independent experiments. These observations are consistent with a mechanism in which the LHRH-curcumin conjugate preferentially affects cells expressing LHRH receptor by binding to the receptor.

Example 3

This example includes data showing that the combination of LHRH-curcumin conjugate and gemcitabine is more effective on Panc-1 spheroids growth.

Panc-1 spheroids were formed in 96-well round bottom plates as described. After the spheroids were established the following treatments were applied (8 spheroids per group): (1) gemcitabine (5 µM); (2) LHRH-curcumin conjugate (30 µM); (3) gemcitabine plus LHRH-curcumin conjugate; (4) DMSO control.

Figure 4:
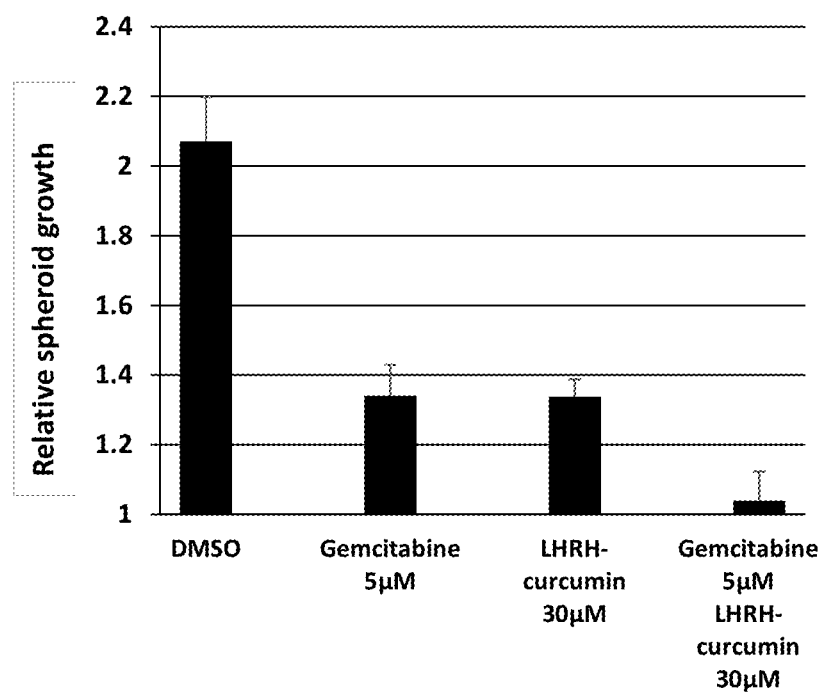
FIG. 4 shows Panc-1 spheroids growth following treatment with gemcitabine (5 µM), LHRH-curcumin (30 µM) or gemcitabine in combination with LHRH-curcumin. DMSO was used as a control.

Analysis shows that LHRH-curcumin conjugate plus gemcitabine treated spheroids were significantly smaller than spheroids treated with either LHRH-curcumin conjugate or gemcitabine administered alone. Results are presented in FIG. 4. Reproducibility was confirmed in three independent experiments.

These results indicate that the LHRH-curcumin conjugate strongly inhibits Panc-1 spheroids growth when in combination with gemcitabine, and could be used in combination therapy in other cancer cells expressing LHRH receptor.

Example 4

This example includes data showing that the combination of LHRH-curcumin conjugate and gemcitabine at low doses is more effective on Panc-1, Mia-Paca-2 and AsPC-1 spheroids growth.

Panc-1, Mia-Paca-2 and AsPC-1 spheroids were formed in 96-well round bottom plates as described. After the spheroids were established the following treatments were applied (8 spheroids per group): following dose-dependent (0.5 µM, 1.0 µM and 5.0 µM) treatment with gemcitabine alone and in combination with LHRH-curcumin (10 µM and 20 µM). Media alone was used as control. The spheroids were grown for 5 days before quantification. Both gemcitabine and LHRH-curcumin were diluted in water. The spheroids were treated as follows:
1. Mock
2. Gemcitabine 0.5 uM
3. Gemcitabine 1 uM
4. Gemcitabine 5 uM
5. LHRH-curcumin 10.0 uM
6. LHRH-curcumin 20.0 uM
7. Gemcitabine (0.5)+LHRH-c (10)
8. Gemcitabine (1)+LHRH-c (10)
9. Gemcitabine (5)+LHRH-c (10)
10. Gemcitabine (0.5)+LHRH-c (20)
11. Gemcitabine (1)+LHRH-c (20)
12. Gemcitabine (5)+LHRH-c (20)

Figure 5A:
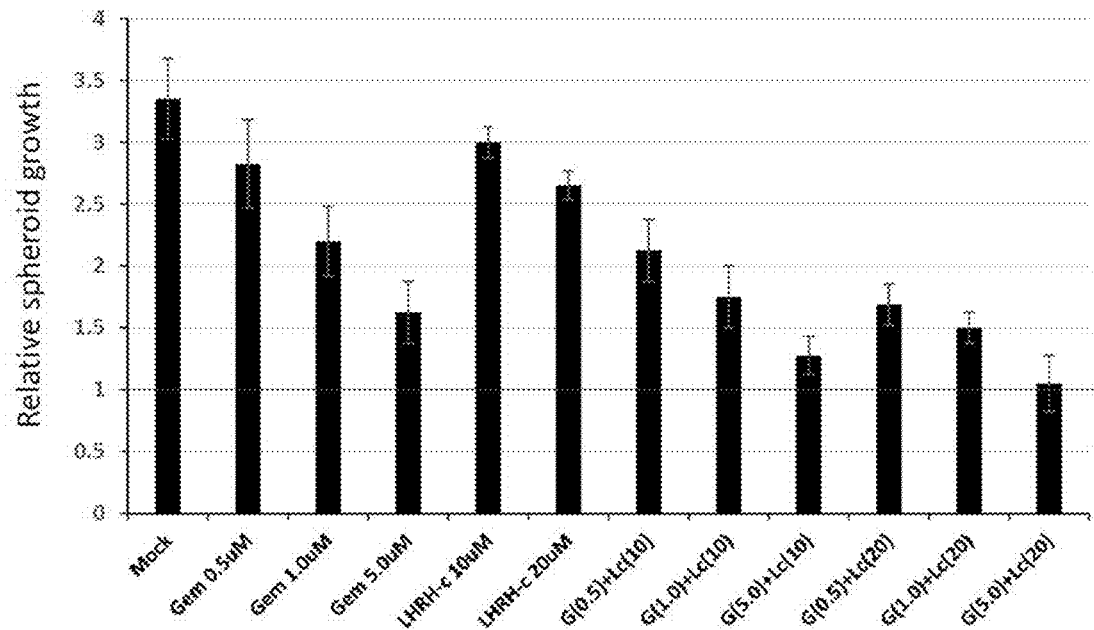
FIG. 5A shows quantification of MiaPaca-2 spheroids treated with gemcitabine and LHRH-curcumin (120 h).
Figure 5B:
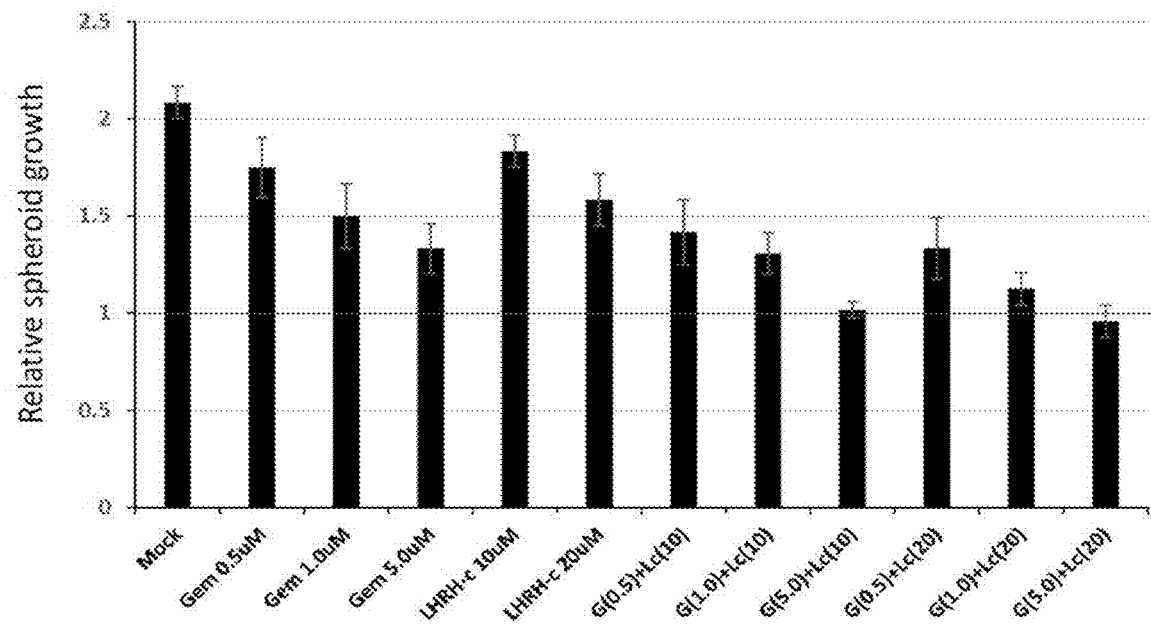
FIG. 5B shows quantification of Panc-1 spheroids treated with gemcitabine and LHRH-curcumin (120 h).
Figure 5C:
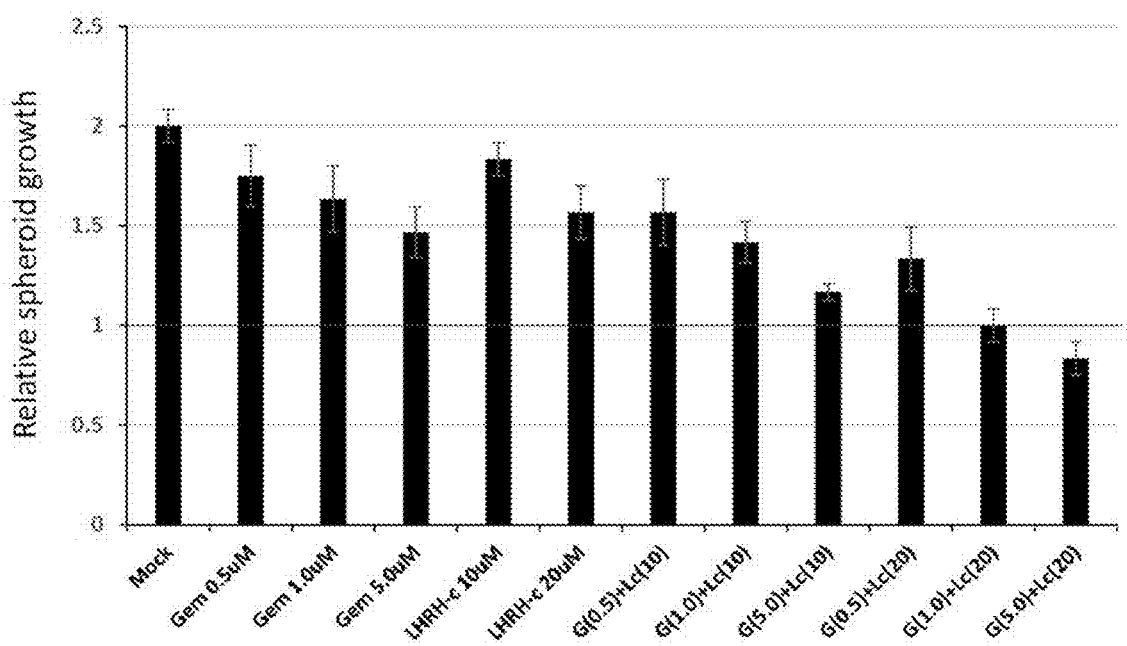
FIG. 5C shows quantification of AsPC-1 spheroids treated with gemcitabine and LHRH-curcumin (120 h).

IncucyteZOOM software analysis using the "average red object area in the well" module shows that treatment with gemcitabine and LHRH-curcumin decrease the size of the spheroids formed by MiaPaca-2, Panc-1 and AsPC-1 cells in a dose-dependent manner. The LHRH-curcumin conjugate plus gemcitabine treated spheroids were significantly smaller than spheroids treated with either LHRH-curcumin conjugate or gemcitabine administered alone. Results presented in FIG. 5A (Mia-Paca-2), FIG. 5B (Panc-1) and FIG. 5C (AsPC-1).

These results indicate that the LHRH-curcumin conjugate strongly inhibit Panc-1, Mia-Paca-2 and AsPC-1 spheroids growth when in combination with gemcitabine at low doses and was significantly more effective in reducing the spheroids size than either compound administered alone. Such a LHRH-curcumin conjugate/gemcitabine combination therapy could be used in other cancer cells expressing LHRH receptor to reduce side-effects of chemotherapy while providing a good tumor growth inhibition.

Example 5

This example includes data showing that the combination LHRH-curcumin conjugate and 5 FU is more effective on Panc-1 and Mia-Paca-2 spheroids growth.

Panc-1 and Mia-Paca2 spheroids were formed in 96-well round bottom plates as described. After the spheroids were established the following treatments were applied (8 spheroids per group): (1) 5 FU (2.5 µM); (2) LHRH-curcumin conjugate (10 µM); (3) 5 FU plus LHRH-curcumin conjugate; (4) DMSO control.

Figure 6A:
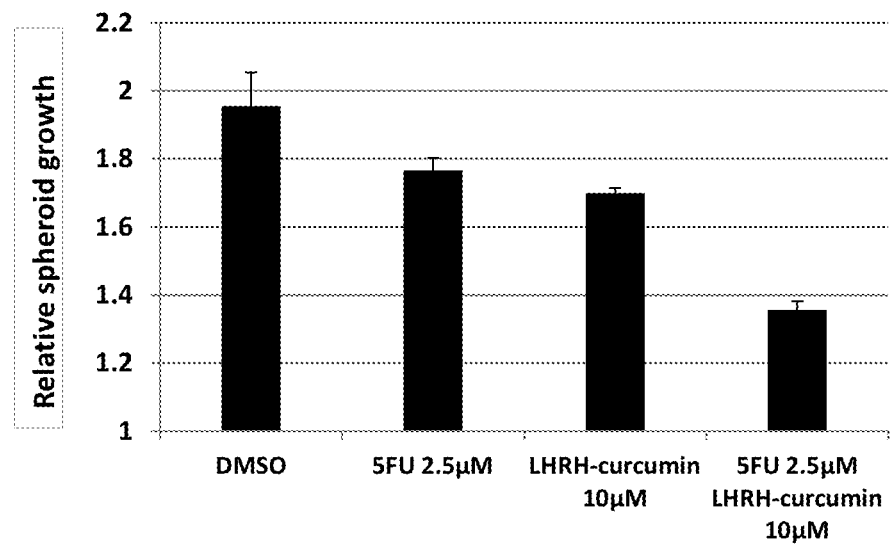
FIG. 6A shows Panc-1 spheroids growth following treatment with 5FU (2.5 µM), LHRH-curcumin (10 µM) or 5 FU in combination with LHRH-curcumin. DMSO was used as a control.
Figure 6B:
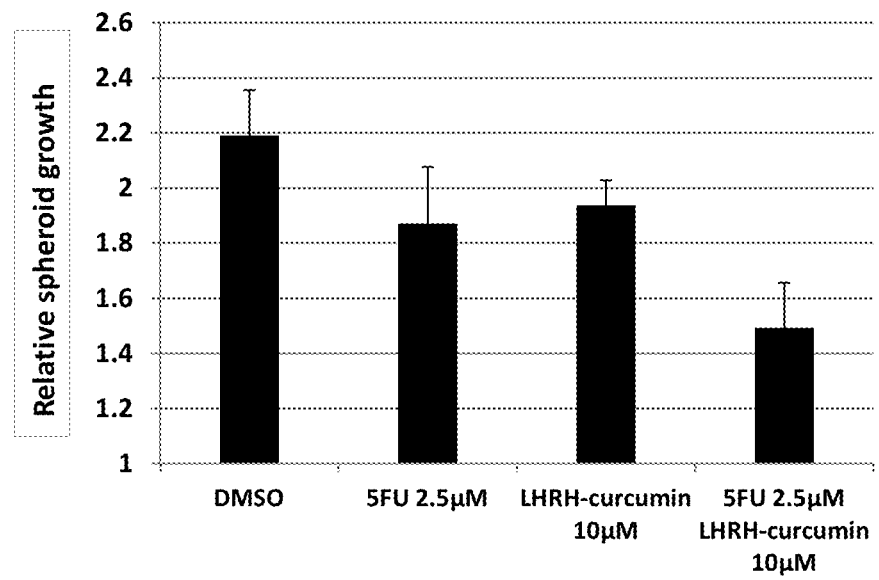
FIG. 6B shows Mia-Paca-2 spheroids growth following treatment with 5 FU (2.5 µM), LHRH-curcumin (10 µM) or 5 FU in combination with LHRH-curcumin. DMSO was used as a control.

Analysis shows that LHRH-curcumin conjugate plus 5 FU treated spheroids were significantly smaller than spheroids treated with either compound administered alone. Results are presented in FIG. 6A (Panc-1) and FIG. 6B (Mia-Paca-2).

These results suggest that the LHRH-curcumin conjugate strongly inhibit Panc-1 and Mia-Paca2 spheroids growth when in combination with 5 FU, and by implication, could be used in therapy in cancer cells expressing LHRH receptor.

Example 6

This example includes data showing that LHRH-receptor is required for the inhibitory effect of LHRH and LHRH-curcumin conjugate on Panc-1 cells spheroids growth.

Figure 7A:
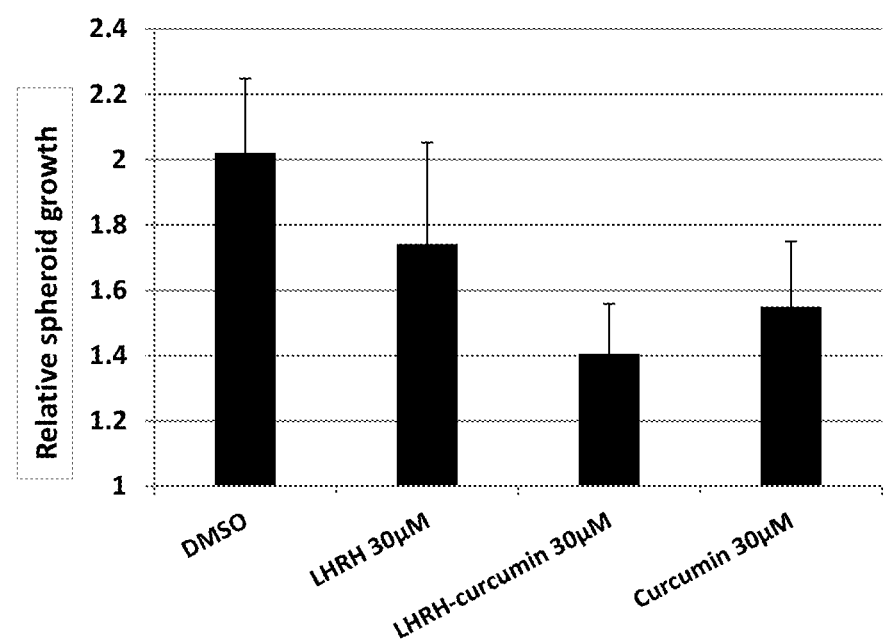
FIG. 7A shows Panc-1 spheroids (non-target control [NT]) growth following treatment with LHRH alone (30 µM), LHRH-curcumin (30 µM) or curcumin alone (30 µM). DMSO was used as control.
Figure 7B:
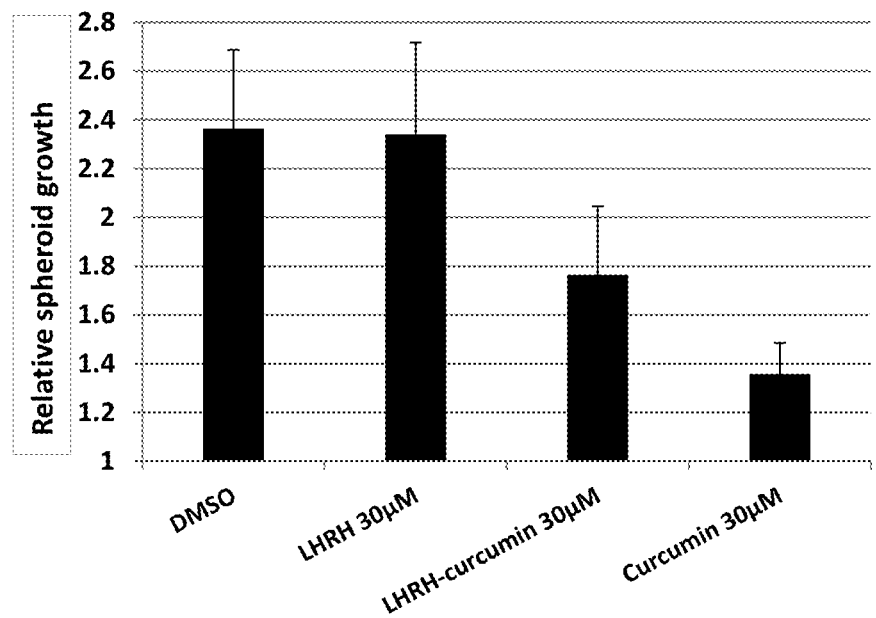
FIG. 7B shows Panc-1 spheroids (LHRHR knock-down [KD]) growth following treatment with LHRH alone (30 µM), LHRH-curcumin (30 µM) or curcumin alone (30 µM). DMSO was used as control.

To verify that the effect of LHRH and LHRH-curcumin conjugate was due to binding to cell-surface LHRH receptor, non-target control (NT)) Panc-1 spheroides and LHRHR knock-down (KD) Panc-1 spheroides were treated with LHRH, LHRH-curcumin conjugate and curcumin alone and measured the spheroids growth (FIG. 7). The data show that free LHRH has an inhibitory effect on NT Panc-1 spheroids growth consistent with the presence of LHRHR at the cell surface. Also, as previously shown, the effect of LHRH-curcumin conjugate was superior to that of LHRH or curcumin alone (FIG. 7A). However, the inhibitory effect of LHRH was abolished in LHRHR KD Panc-1 spheroides. Even more, although LHRH-curcumin conjugate still has an effect on spheroids growth formed by LHRHR KD cells, its effect was inferior to that of curcumin alone, suggesting that at least partially the effect of LHRH-curcumin conjugate is due to binding on the receptor at the cell surface (FIG. 7B).

These observations are consistent with a mechanism in which the LHRH-curcumin conjugate preferentially affects cancer cells by binding to LHRH receptor.

Example 7

This example includes data showing that LHRH receptor has a molecular weight of 45 kD and only a small percentage appears to be at the cell surface.

Figure 8B:
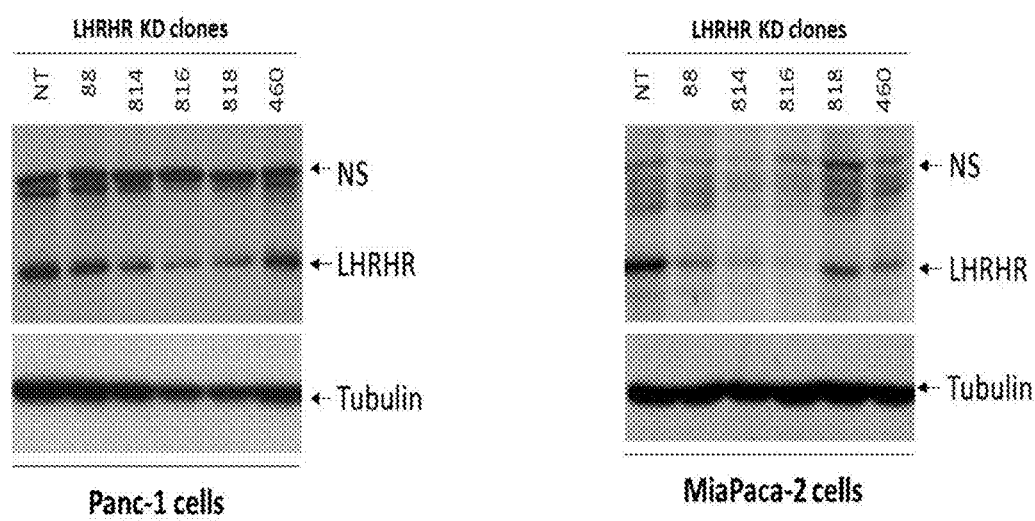
FIG. 8B shows Western blot analysis demonstrating knockdown in the expression of LHRH receptor in cancer cells.

The molecular weight of LHRHR has been predicted to anywhere from 35 kD to over 70 kD, a conclusion that to a large extent has been based on antibodies that are very non specific. FIG. 8B is a western blot of pancreatic tumor cell lysates demonstrating that the GenScript antibody recognizes a strong band 66 kD while the Abcam antibody recognizes a major band at about 45 kD. Washing serum away from the cells eliminates the 66 kD band, suggesting that the GenScript antibody is most likely recognizing serum albumin.

FIG. 8B demonstrates that in cells infected with a lentivirus encoding shRNA against LHRHR, that the 45 kD band is reduced using some of the viral clones, strongly suggesting that the 45 kD band recognized by the AbCam antibody is the authentic receptor. This is, to our knowledge, is the first validated experiment demonstrating the specificity of an LHRHR antibody and that the 45 kD protein represents this receptor.

There has been disagreement about the actual level of cell surface expression of the LHRHR. Some groups claim a majority of the receptor resides there while other groups state less than 5% is ever present at the cell surface, with the remainder associating with the endoplasmic reticulum. To determine cell surface LHRHR, biotin was attached to the cell surface, the biotinylated proteins recovered and compared, by western blot analysis, levels of LHRHR at the cell surface versus total LHRHR expression. Control was the oncogenic receptor c-Met which was primarily found at the cell surface.

Figure 8C:
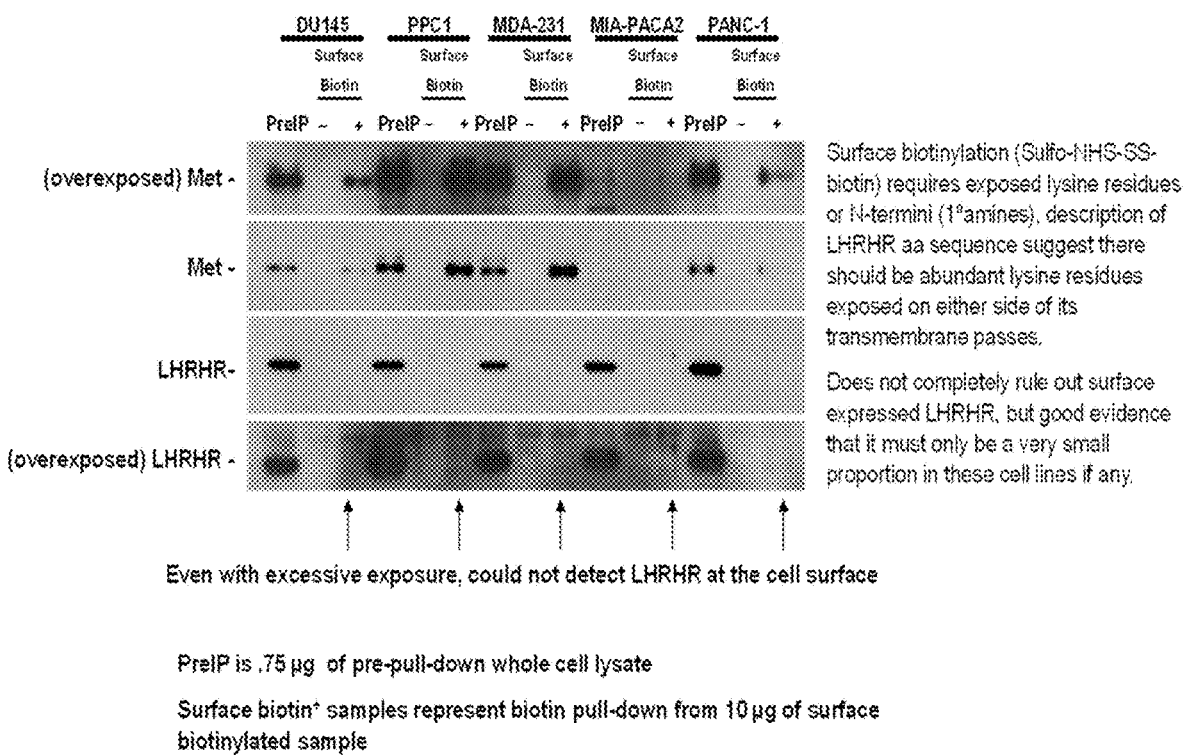
FIG. 8C shows extremely low expression of the LHRH receptor at the cell surface of cancer cells.

FIG. 8C demonstrates that in five tumor cell-lines no detectable surface expressed LHRHR was found. This is consistent with other observations using flow cytometric analysis and confocal microscopy that very little of the expressed LHRHR is expressed on the surface of the cell. This is important information since it suggests that pharmacological chaperones might be discovered that could increase surface expression of LHRHR and increase the efficacy of targeted agents.

Example 8

This example includes a brief description of various materials and methods used in Examples 9-14.

Cell Proliferation Analysis:

Pancreatic cells were collected after trypsinization and seeded in 96-well plates for 24 h before treatments. Treatments were performed as described in Figure legends. After paraformaldehyde fixation and DAPI staining cell number was quantified using the "Object Count" module of the ThermoFisher Cellomics VTI software. Graphs represent the average and standard deviation of eight wells under the same treatment conditions.

Western Blot Analysis:

Pancreatic cells were collected after trypsinization and seeded in 12-well plates for 24 h before treatments. Treatments were performed as described in the Figure legends. Following treatment, whole cell lysates were collected in Laemmli buffer and analyzed by Western blot. The following primary antibodies were used: XIAP, c-IAP2, cleaved PARP, Caspase-3 (all from Cell Signaling), actin (Santa Cruz) and LHRHR (Abcam).

Quantitative PCR Analysis:

mRNA levels of XIAP, c-IAP1 and c-IAP2 were determined by quantitative real-time PCR using the SYBR Green Real-Time PCR Master Mix form ThermoFisher. Thermal cycling was carried out using the CFX system from BioRad under the following conditions: 95° C. for 10 min and 40 cycles at 95° C. for 15 s and 55° C. for 60 s. mRNA expression for any given gene is represented as comparative to the DMSO-treated cells. GAPDH was used as the housekeeping gene of reference.

Example 9

This example includes data showing that combinations of gemcitabine with LHRH-curcumin are more efficient in inhibiting cell proliferation and/or inducing cell death.

Nuclei counting after DAPI staining and quantification of cell proliferation/growth using ThermoFisher Cellomics VTI imaging system and software post-treatment with gemcitabine and LHRH-curcumin alone and in combination. Cell number was determined after DAPI staining of nuclei. Cells were treated as described in FIG. 1.

Figure 9A:
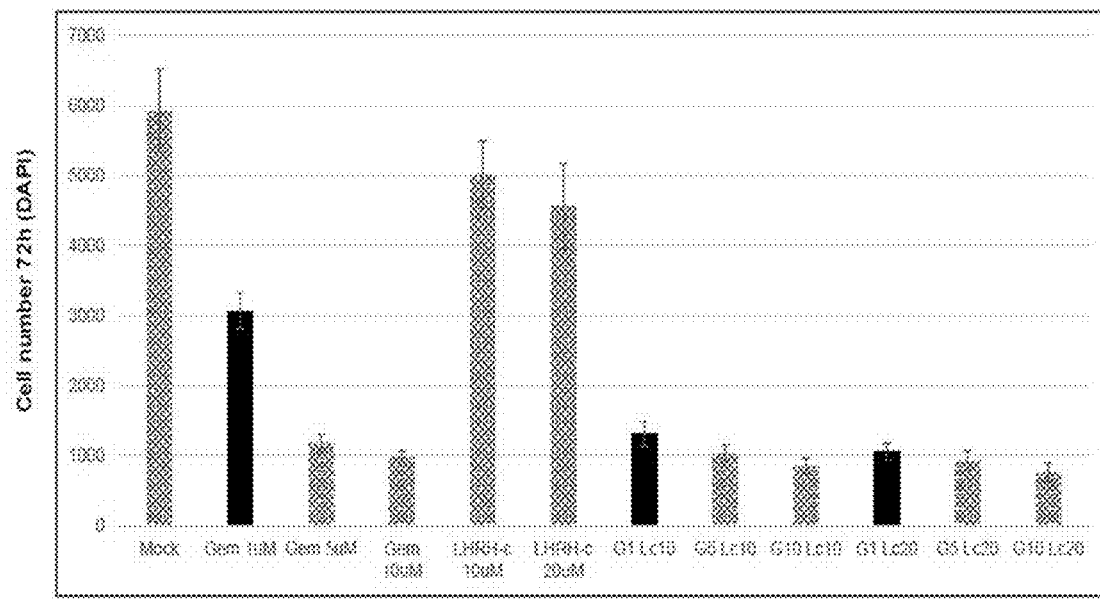
FIG. 9A shows Cellomics nuclei quantification of MiaPaca-2 cells treated with gemcitabine and LHRH-curcumin.
Figure 9B:
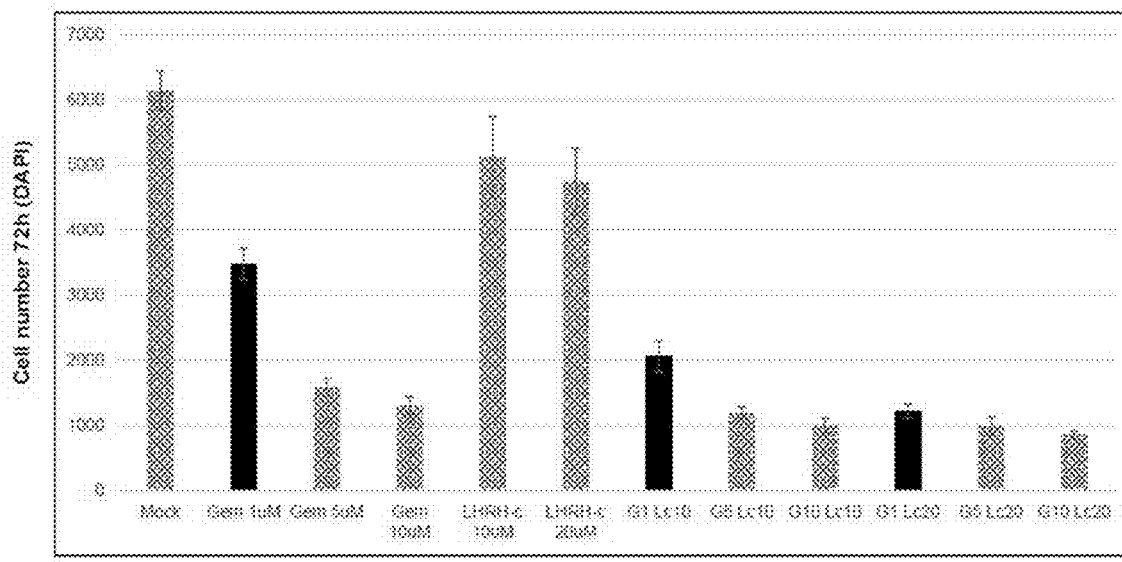
FIG. 9B shows Cellomics nuclei quantification of Panc-1 cells treated with gemcitabine and LHRH-curcumin.
Figure 9C:
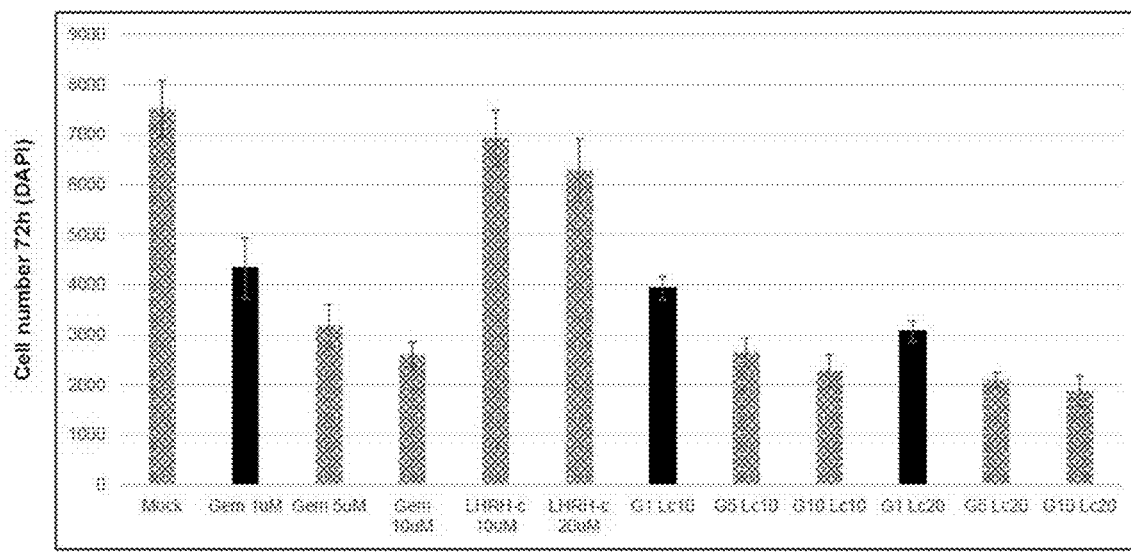
FIG. 9C shows Cellomics nuclei quantification of AsPC-1 cells treated with gemcitabine and LHRH-curcumin.
Figure 9D:
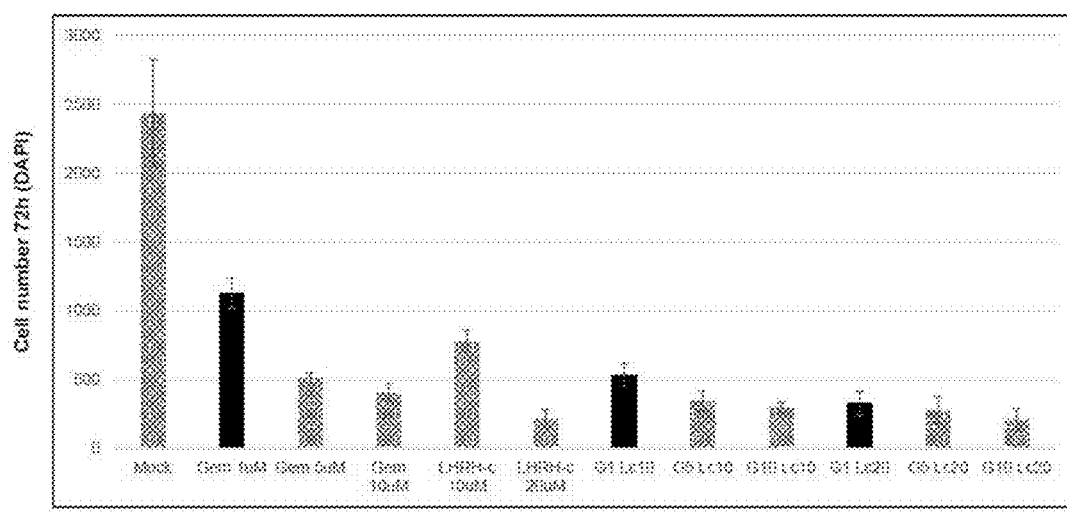
FIG. 9D shows Cellomics nuclei quantification of BxPC-3 cells treated with gemcitabine and LHRH-curcumin.

Eight replicates per treatment were used for quantification. Results presented in FIG. 9A (MiaPaca-2 cells), FIG. 9B (Panc-1 cells), FIG. 9C (AsPC-1 cells) and FIG. 9D (BxPC-3 cells). Quantification of nuclei support the results obtained with IncucyteZOOM and further confirm that cancer cells are sensitive to the treatment in a dose-dependent manner and that combinations of gemcitabine with LHRH-curcumin are more efficient in inhibiting cell proliferation and/or inducing cell death.

Example 10

This example includes analysis of apoptosis markers (cleaved PARP) and inhibitors of apoptosis (XIAP and cIAP2) 24 h post-treatment.

Figure 10A:
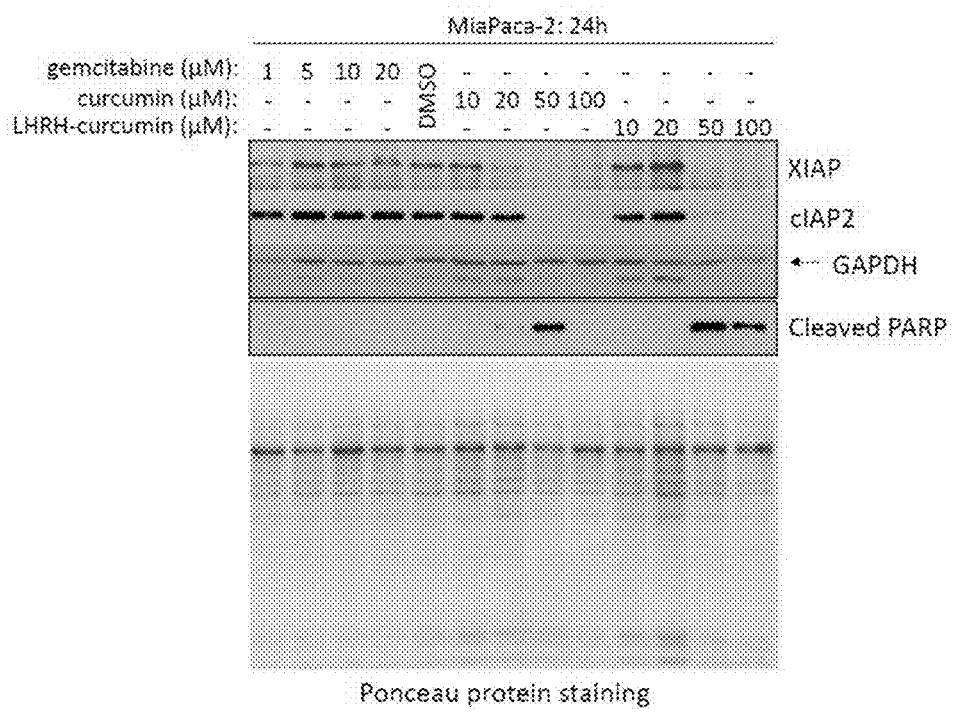
FIG. 10A shows apoptosis markers in MiaPaca-2 cells treated with gemcitabine and LHRH-curcumin (24 h).
Figure 10B:
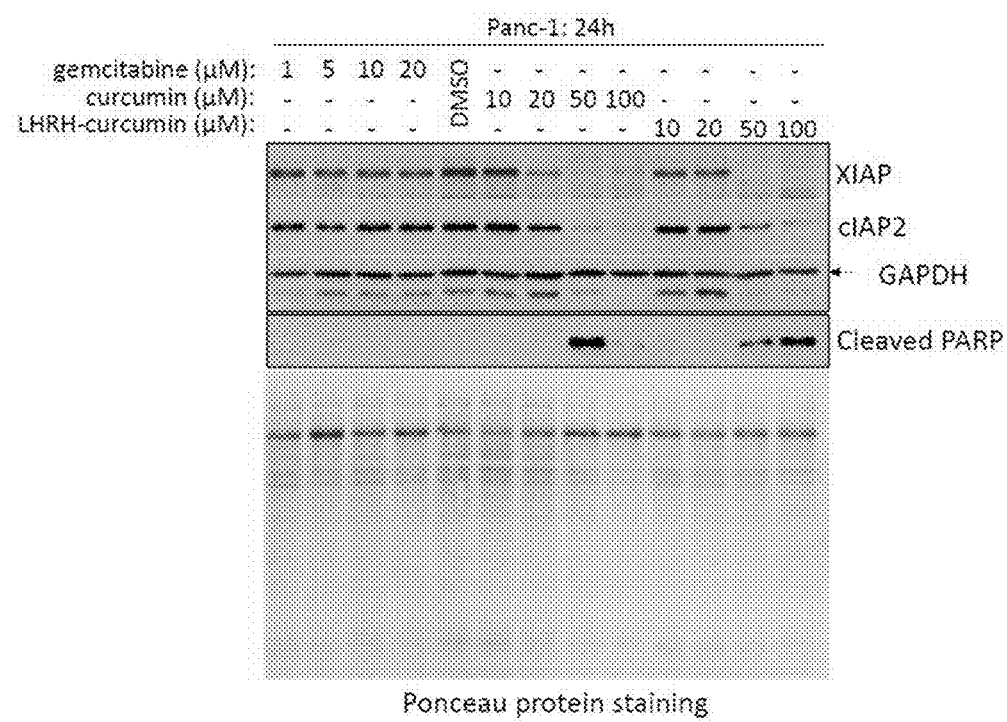
FIG. 10B shows apoptosis markers in Panc-1 cells treated with gemcitabine and LHRH-curcumin (24 h).
Figure 10C:
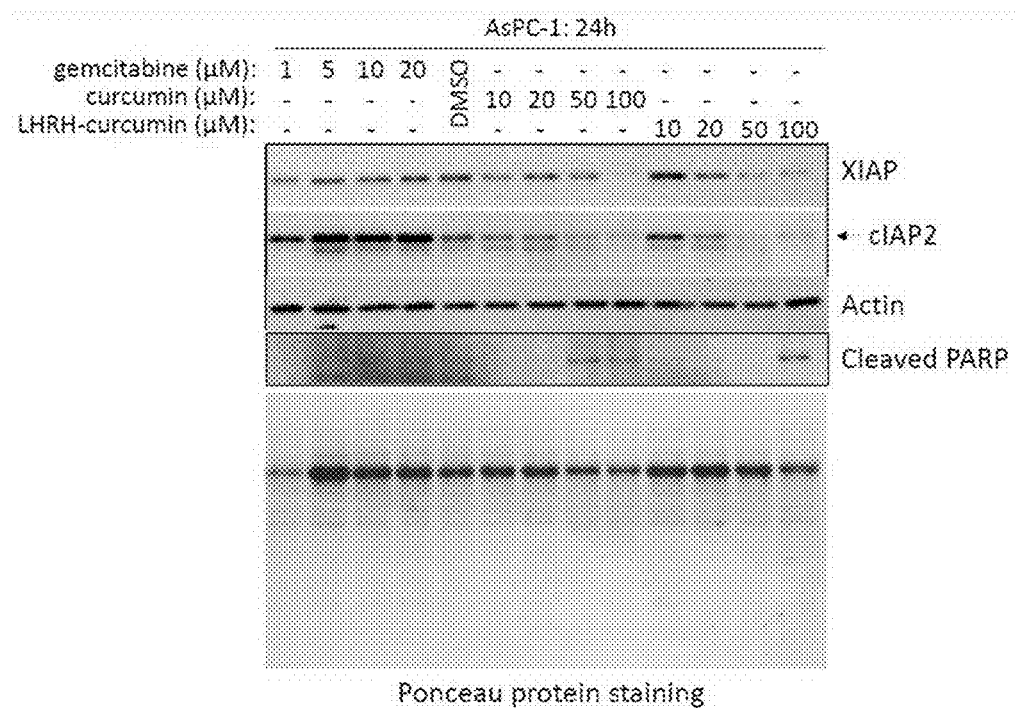
FIG. 10C shows apoptosis markers in AsPC-1 cells treated with gemcitabine and LHRH-curcumin (24 h).
Figure 10D:
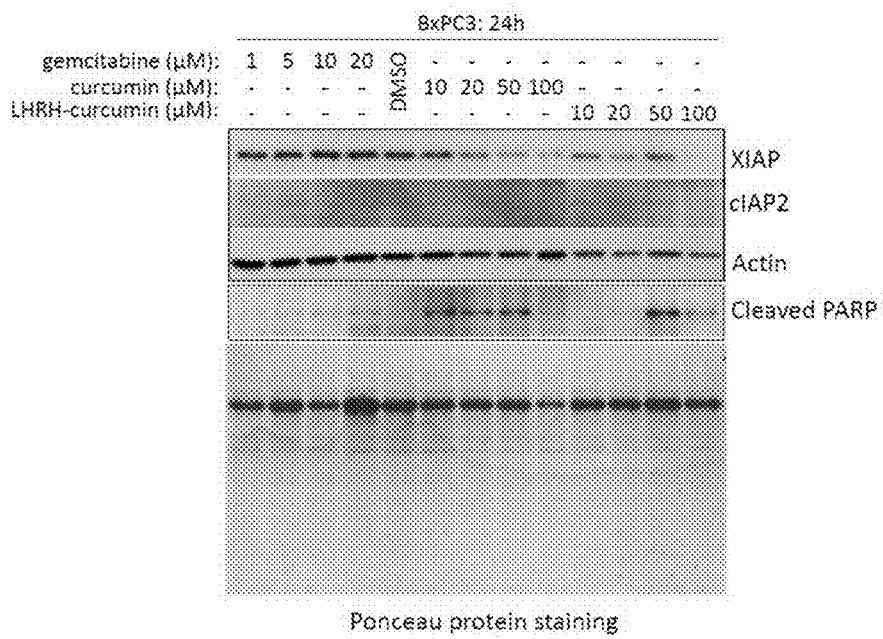
FIG. 10D shows apoptosis markers in BxPC-3 cells treated with gemcitabine and LHRH-curcumin (24 h).

Western blot analysis. Actin, GAPDH and Ponceau staining were used as loading controls. Gemcitabine was diluted in water. Curcumin and LHRH-curcumin were diluted in DMSO. Cells were treated as follows:
1. Gemcitabine 1 uM
2. Gemcitabine 5 uM
3. Gemcitabine 10 uM
4. Gemcitabine 20 uM
5. DMSO
6. Curcumin 10 uM
7. Curcumin 20 uM
8. Curcumin 50 uM
9. Curcumin 100 uM
10. LHRH-curcumin 10 uM
11. LHRH-curcumin 20 uM
12. LHRH-curcumin 50 uM
13. LHRH-curcumin 100 uM Results presented in FIG. 10A (MiaPaca-2 cells), FIG. 10B (Panc-1 cells), FIG. 10C (AsPC-1 cells) and FIG. 10D (BxPC-3 cells). All pancreatic cell lines including MiaPaca-2, Panc-1, AsPC-1 and BxPC-3 are sensitive to curcumin and LHRH-curcumin treatment and initiate apoptosis as illustrated by the presence of cleaved PARP 24 h post-treatment. Higher doses of curcumin and LHRH-curcumin, 50 uM and 100 uM respectively are more efficient in initiating cell death 24 h post-treatment.

Panc-1 and MiaPaca-2 pancreatic cell lines are more resistant to gemcitabine treatment as even the highest dose of gemcitabine (20 uM) failed to induce apoptosis 24 h post-treatment. As illustrated by Western blot analysis no cleaved PARP was detected in Panc-1 and MiaPaca-2 cells 24 h post-treatment with gemcitabine. Low levels of cleaved PARP was detected in AsPC-1 and BxPC-3 treated with gemcitabine at higher doses. XIAP and c-IAP2 inhibitors of apoptosis proteins are down-regulated by high doses of curcumin and LHRH-curcumin (50 uM and 100 uM) alone in all pancreatic cell lines 24 h post-treatment further confirming that all pancreatic cancer cell lines used are sensitive to both curcumin and LHRH-curcumin. Gemcitabine alone doesn't affect XIAP and c-IAP2 levels 24 h post-treatment.

Example 11

This example includes analysis of apoptosis markers (cleaved PARP) and inhibitors of apoptosis (XIAP and cIAP2) 24 h post-treatment.

Figure 11A:
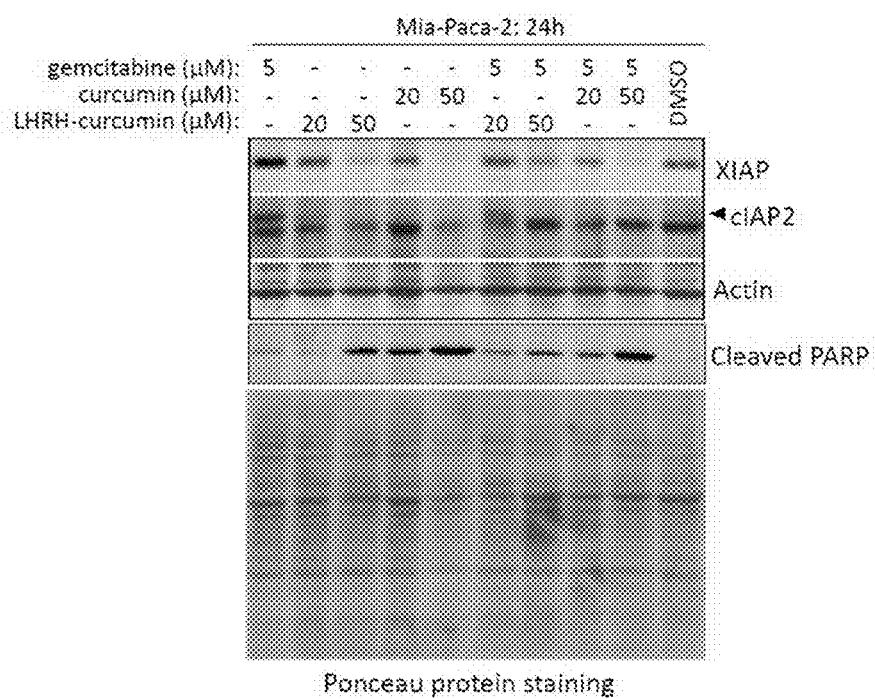
FIG. 11A shows apoptosis markers in MiaPaca-2 cells treated with combination treatment (24 h).
Figure 11B:
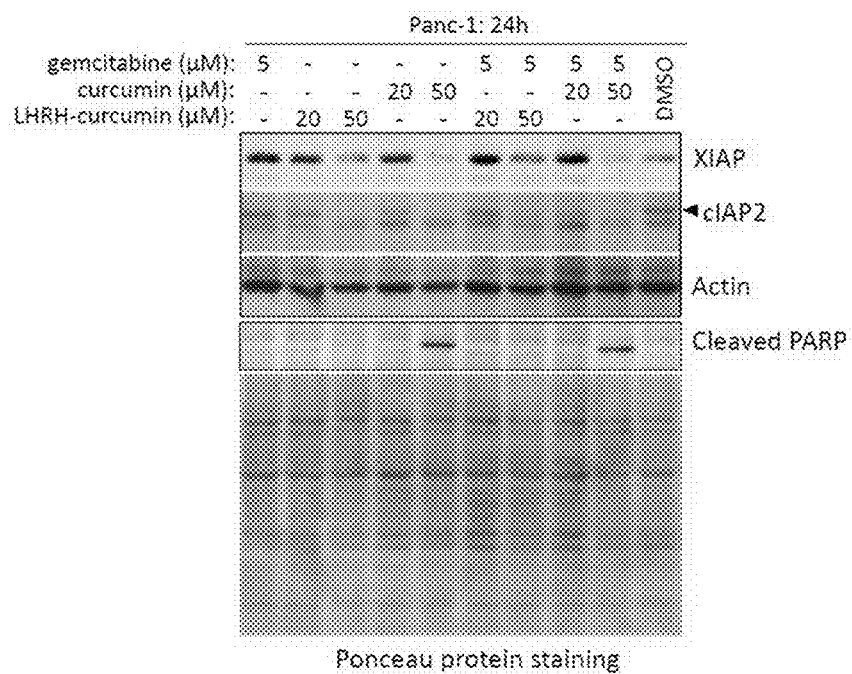
FIG. 11B shows apoptosis markers in Panc-1 cells treated with combination treatment (24 h).
Figure 11C:
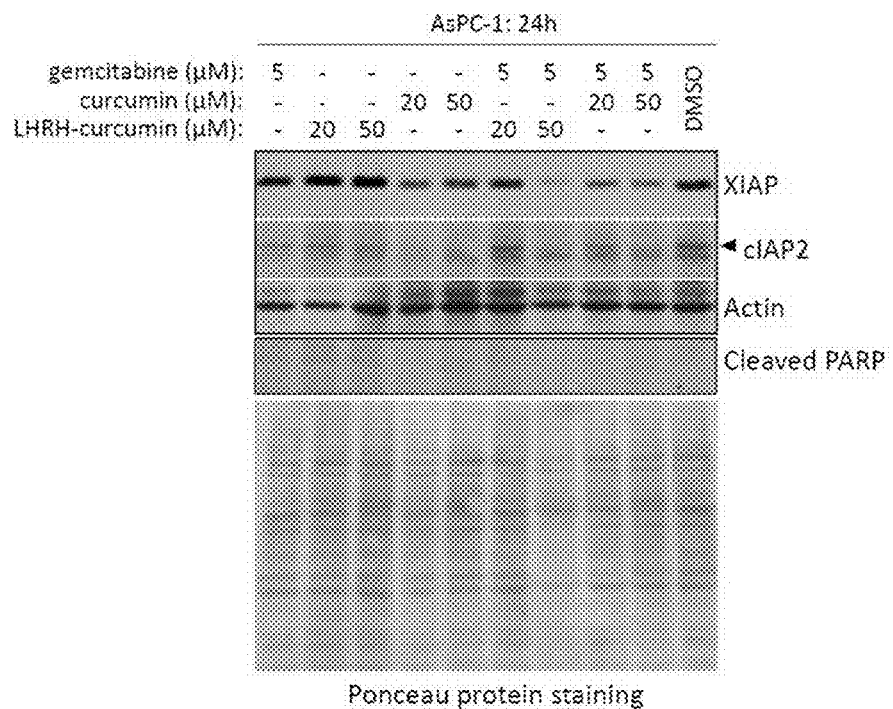
FIG. 11C shows apoptosis markers in AsPC-1 cells treated with combination treatment (24 h).
Figure 11D:
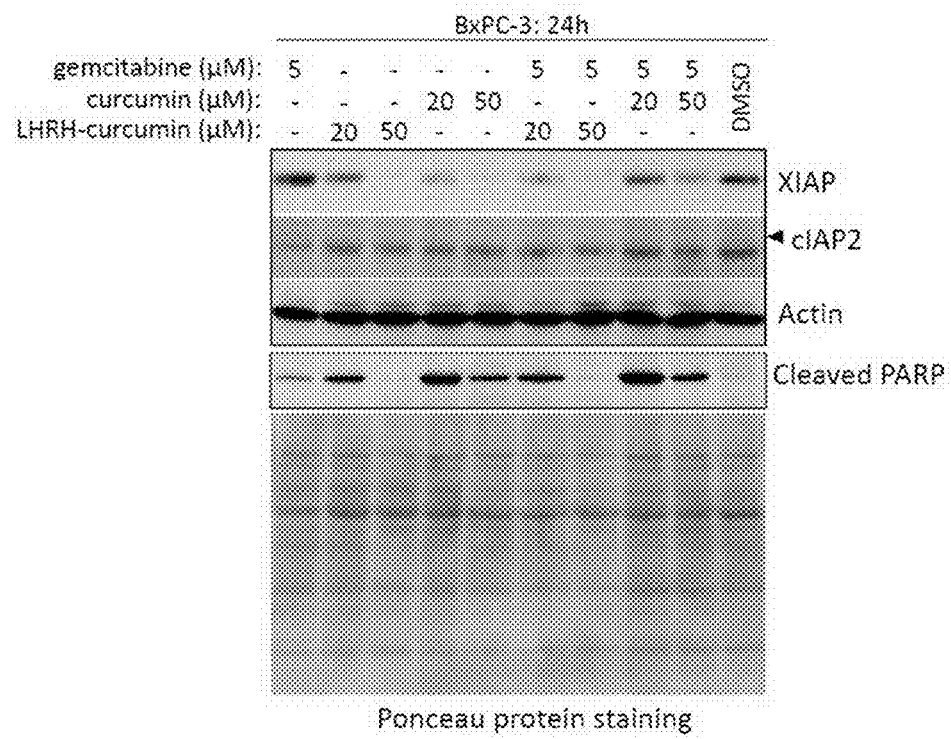
FIG. 11D shows apoptosis markers in BxPC-3 cells treated with combination treatment (24 h).

Western blot analysis. Actin, GAPDH and Ponceau staining were used as loading controls. Gemcitabine was diluted in water. Curcumin and LHRH-curcumin were diluted in DMSO. The cells were treated as follows:
1. Gemcitabine 5 uM
2. LHRH-curcumin 20 uM
3. LHRH-curcumin 50 uM
4. Curcumin 20 uM
5. Curcumin 50 uM
6. Gemcitabine (5)+curcumin (20)
7. Gemcitabine (5)+curcumin (50)
8. Gemcitabine (5)+LHRH-curcumin (20)
9. Gemcitabine (5)+LHRH-curcumin (50)
10. DMSO Results presented in FIG. 11A (MiaPaca-2 cells), FIG. 11B (Panc-1 cells), FIG. 11C (AsPC-1 cells) and FIG. 11D (BxPC-3 cells). XIAP and c-IAP2 inhibitors of apoptosis proteins are down-regulated by high doses of curcumin and LHRH-curcumin (50 uM) even in the presence of gemcitabine (5 uM) in all pancreatic cell lines 24 h post-treatment. While all cell lines down-regulate XIAP and c-IAP2 in the presence of curcumin and LHRH curcumin, initiation of apoptosis at 24 h as revealed by cleaved PARP is distinct among the 4 pancreatic cell lines suggesting that different drug doses might be required to induce apoptosis.

Example 12

This example includes analysis of apoptosis markers (cleaved PARP, cleaved caspase-3) and inhibitors of apoptosis (XIAP and cIAP2) 72 h post-treatment.

Western blot analysis. Actin was used as loading control. Both gemcitabine and LHRH-curcumin were diluted in water. The cells were treated as follows:
1. Mock
2. Gemcitabine 1 uM
3. Gemcitabine 5 uM
4. Gemcitabine 10 uM
5. LHRH-curcumin 10.0 uM
6. LHRH-curcumin 20.0 uM
7. Gemcitabine (1)+LHRH-c (10)
8. Gemcitabine (5)+LHRH-c (10)
9. Gemcitabine (10)+LHRH-c (10)
10. Gemcitabine (1)+LHRH-c (20)
11. Gemcitabine (5)+LHRH-c (20)
12. Gemcitabine (10)+LHRH-c (20)

Figure 12A:
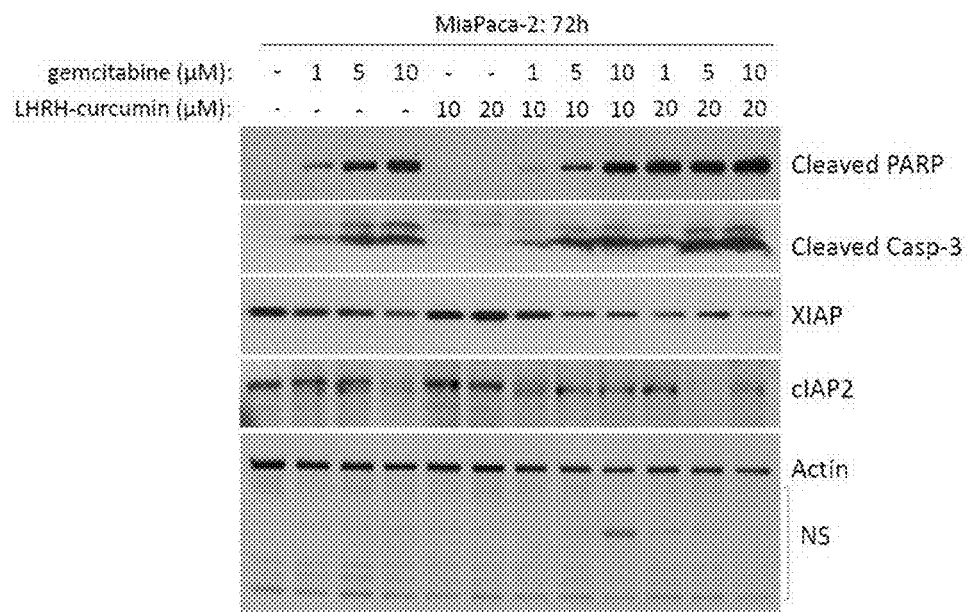
FIG. 12A shows apoptosis markers in MiaPaca-2 cells treated with combination treatment (72 h).
Figure 12B:
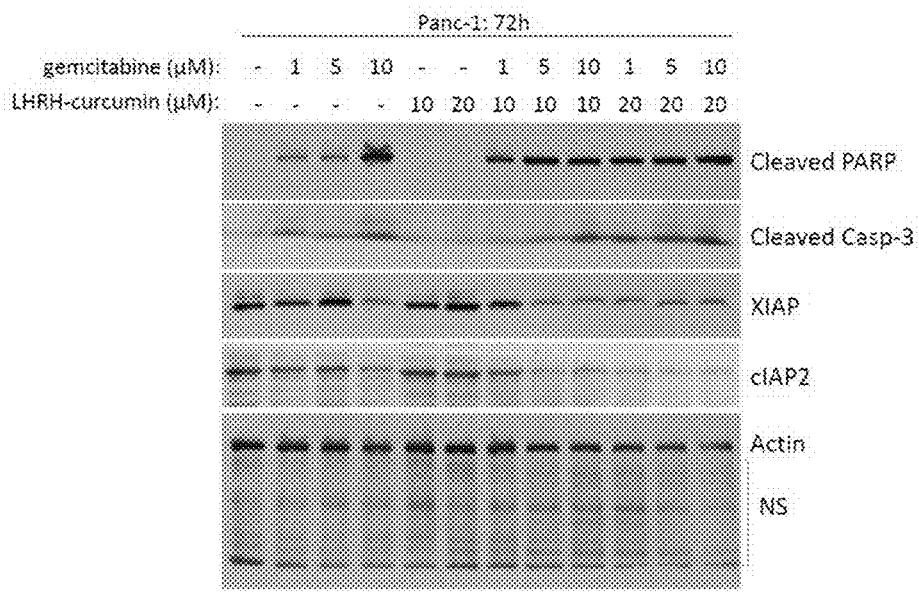
FIG. 12B shows apoptosis markers in Panc-1 cells treated with combination treatment (72 h).
Figure 13A:
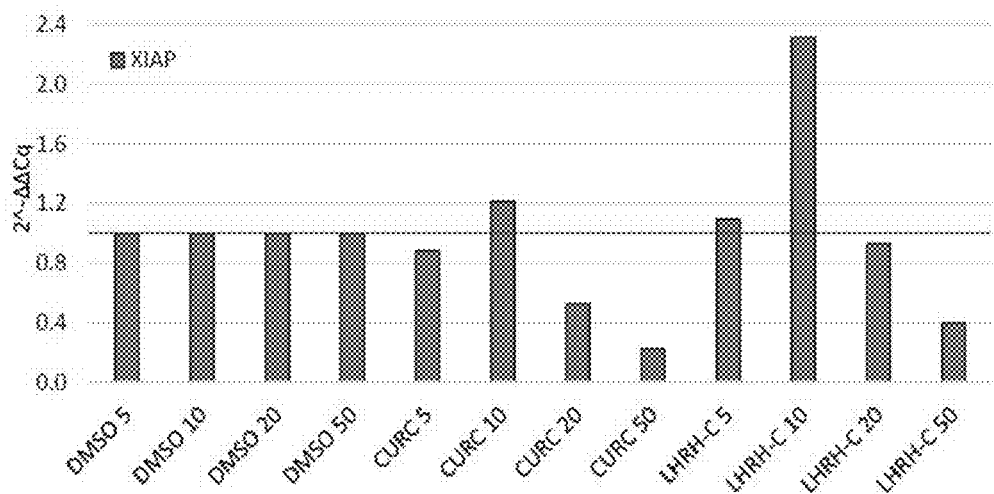
FIG. 13A shows relative mRNA levels of apoptosis inhibitor XIAP in Panc-1 cells treated with curcumin and LHRH-curcumin (24 h).
Figure 13B:
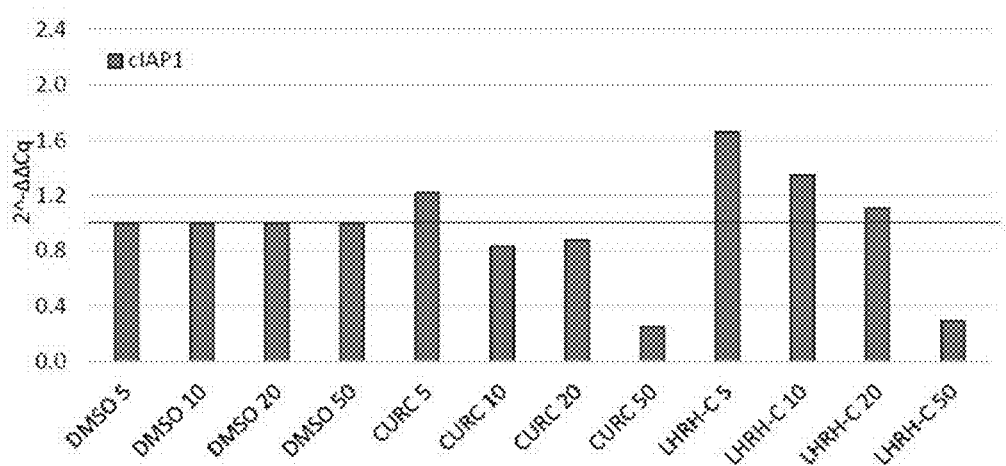
FIG. 13B shows relative mRNA levels of apoptosis inhibitor cIAP1 in Panc-1 cells treated with curcumin and LHRH-curcumin (24 h).
Figure 13C:
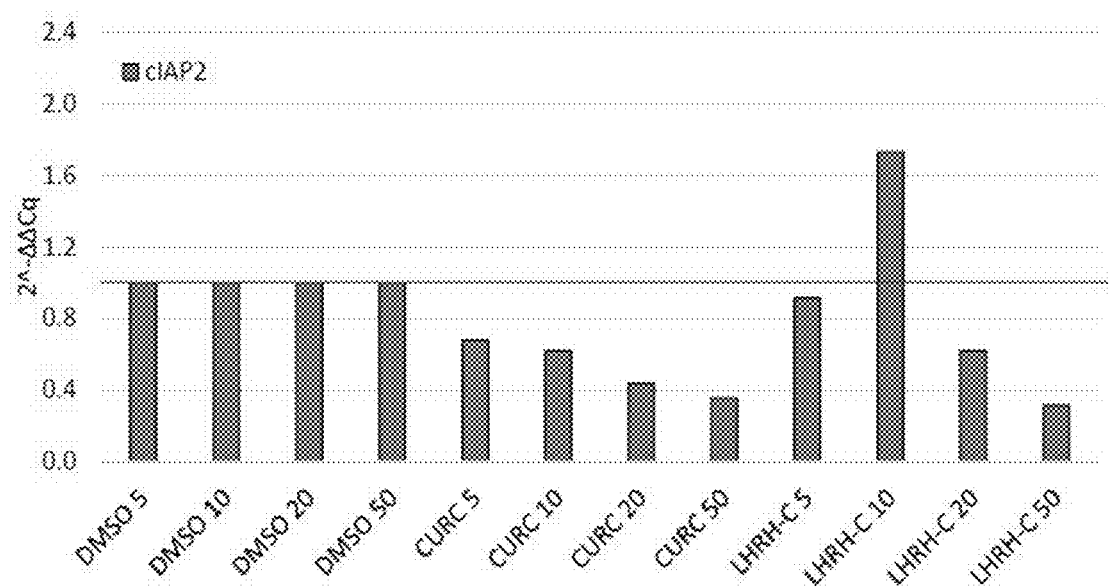
FIG. 13C shows relative mRNA levels of apoptosis inhibitor cIAP2 in Panc-1 cells treated with curcumin and LHRH-curcumin (24 h).

Results presented in FIG. 12A (MiaPaca-2 cells) and FIG. 12B (Panc-1 cells). XIAP and c-IAP2 inhibitors of apoptosis proteins are down-regulated by low dose of LHRH-curcumin (10 uM and 20 uM) in the presence of gemcitabine (5 uM and 10 uM) 72 h post-treatment in MiaPaca-2 and Panc-1 cells. Increased apoptosis at 72 h illustrated by higher levels of cleaved PARP and cleaved caspase 3 is detected when cells are treated with low doses of gemcitabine in combination with low doses of LHRH-curcumin. This data indicates that the combination treatment with lower doses can be as effective in inducing a long-term result with potentially reduced side-effects.

Example 13

This example shows quantitative PCR analysis of mRNA levels of inhibitors of apoptosis XIAP, cIAP1 and cIAP2 in Panc-1 cells treated with curcumin, LHRH-curcumin and DMSO controls.

Cells were treated for 24 h as displayed. GAPDH was used as a reference. Results presented in FIG. 12A (XIAP relative mRNA levels), FIG. 12B (cIAP1 relative mRNA levels), FIG. 12C (cIAP2 relative mRNA levels).

Quantitative-PCR analysis reveal that mRNA levels of XIAP, cIAP1 and c-IAP2 inhibitors of apoptosis are down-regulated by a high dose of curcumin and LHRH-curcumin (50 uM) in Panc-1 pancreatic cell line 24 h post-treatment. QPCR analysis supports the Western blot analysis (FIG. 10 and FIG. 11) and suggest that curcumin and LHRH-curcumin down-regulate XIAP, cIAP1 and c-IAP2 inhibitors of apoptosis at both RNA and protein levels.

Example 14

This example includes data showing LHRHR protein expression in HPNE normal pancreatic cell line and cancer pancreatic cell lines (MiaPaca-2, Pnac-1, AsPC-1 and BxPC-3).

Figure 14:
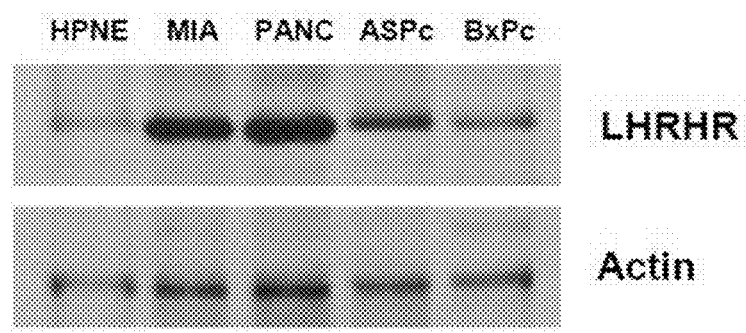
FIG. 14 shows LHRH receptor expression in pancreatic cancer cells and normal cells.
Figure 15:
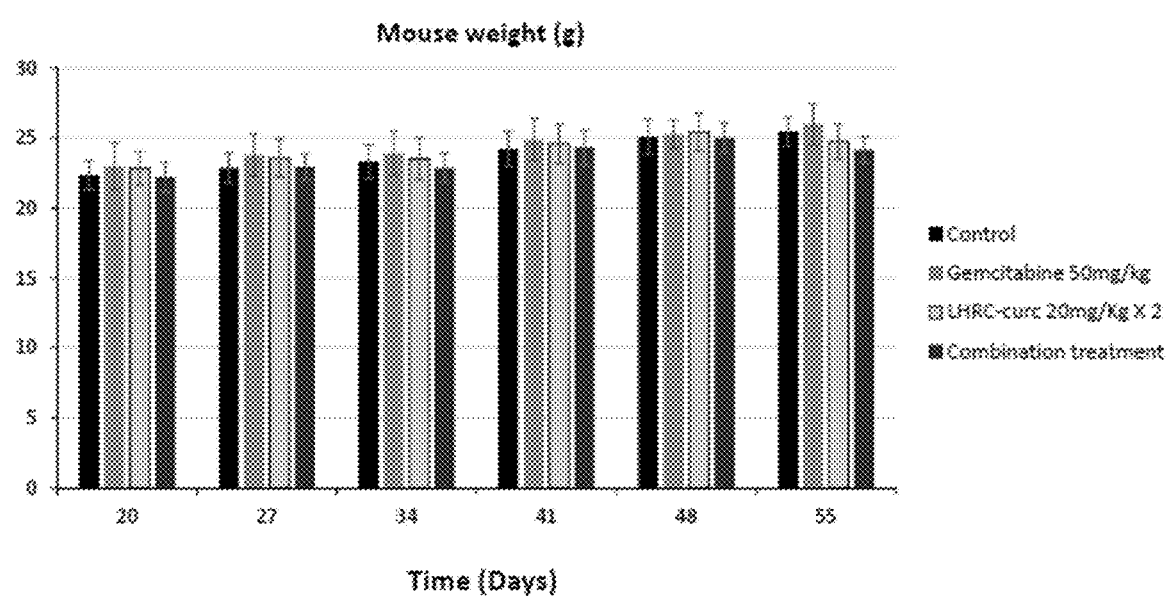
FIG. 15 shows changes in mice weight during treatment with low doses of gemcitabine and LHRH-curcumin: SCID/bg mice were treated weekly with intraperitoneal injections (IP) with vehicle alone (Control), gemcitabine (50 mg/kg, once a week), LHRH-curcumin (20 mg/kg, twice a week) or a combination of gemcitabine and LHRH-curcumin. Mice were monitored for 6 weeks starting on day 20 after tumor implantation. Therapeutic treatment of mice with either gemcitabine or LHRH-curcumin or a combination of the two compounds does not negatively impact body weight or body condition.
Figure 16:
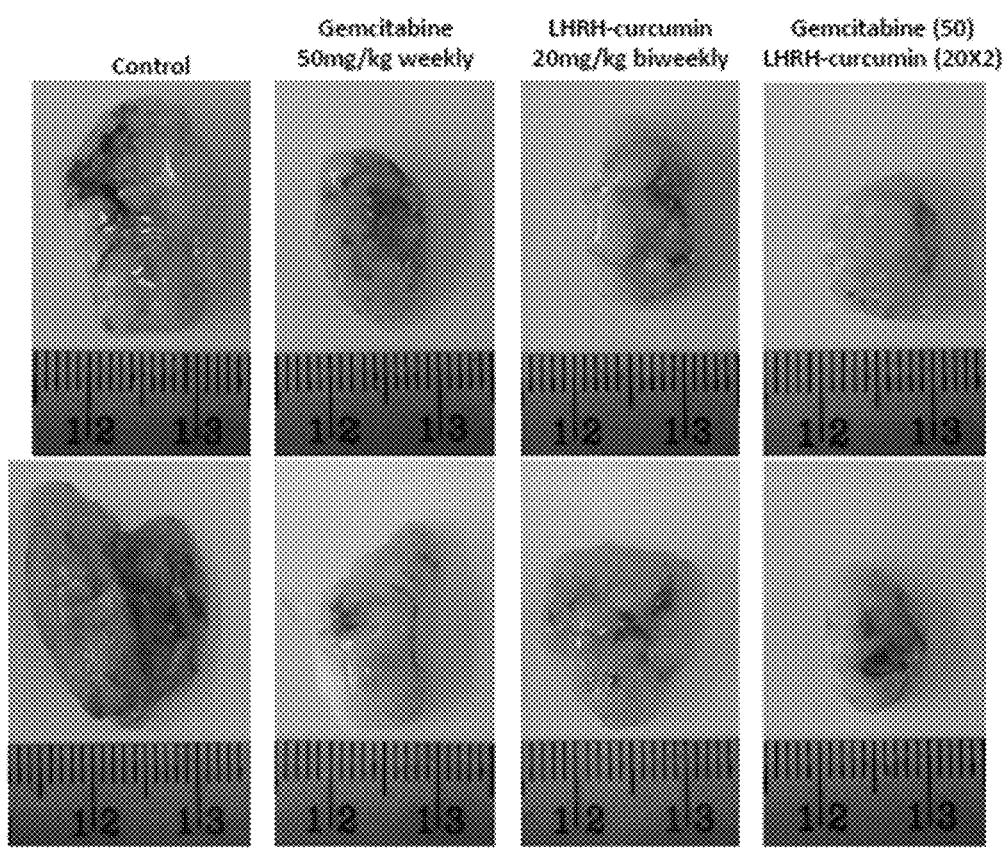
FIG. 16 shows the effect of low doses gemcitabine/LHRH-curcumin treatment on human pancreatic cancer cells Mia-Paca-2 in vivo: Mice were treated weekly with intraperitoneal injections (IP) with vehicle alone (Control), gemcitabine (50 mg/kg, once a week), LHRH curcumin (20 mg/kg, twice a week) or a combination of gemcitabine and LHRH-curcumin. Mice were monitored for 5 weeks starting on day 20 after tumor implantation. On day 55 postimplantation tumors were removed at necropsy. Representative images from vehicle treated, gemcitabine alone, LHRH-curcumin alone and combination treatment shows the evident reduction in tumor size in mice treated with a combination of gemcitabine and LHRH-curcumin.
Figure 17:
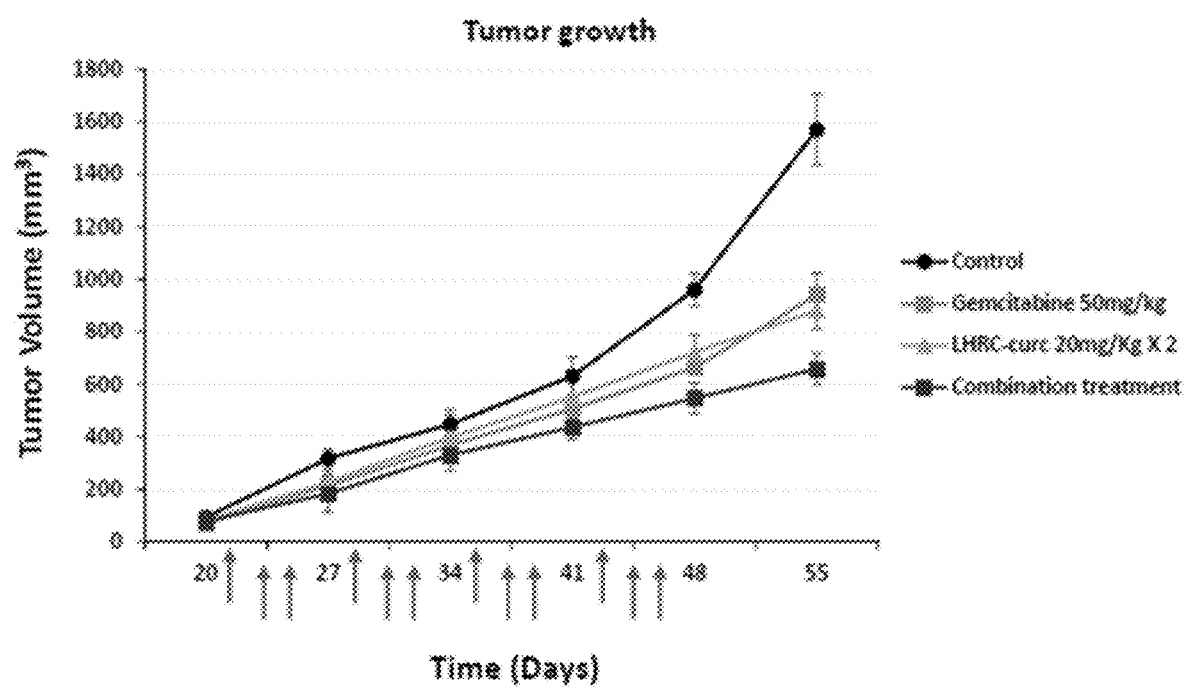
FIG. 17 shows low doses of gemcitabine/LHRH-curcumin combination treatment prevents the growth of pancreatic cancer cells Mia-Paca-2 in vivo: Changes in tumor volumes in SCID/bg mice receiving intraperitoneal injections with vehicle alone (Control), gemcitabine (orange arrows, 50 mg/kg, once a week), LHRH-curcumin (grey arrows, 20 mg/kg, twice weekly) or a combination of gemcitabine and LHRH-curcumin. Data are presented as the mean±SD of tumor volume (n=8).
Figure 18A:
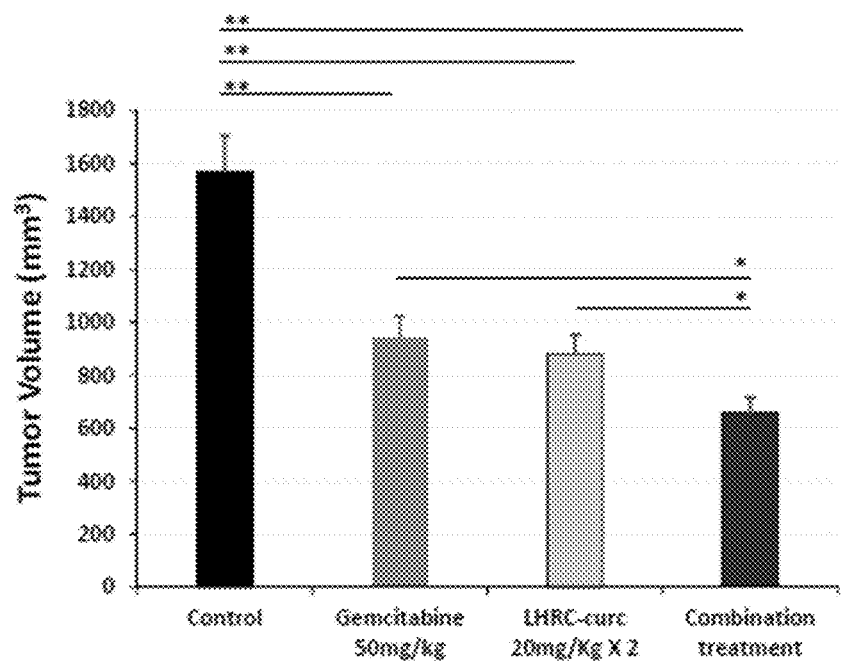
FIG. 18A-18B shows low doses of gemcitabine/LHRH-curcumin combination treatment prevents the growth of pancreatic cancer cells Mia-Paca-2 in vivo.
Figure 18B:
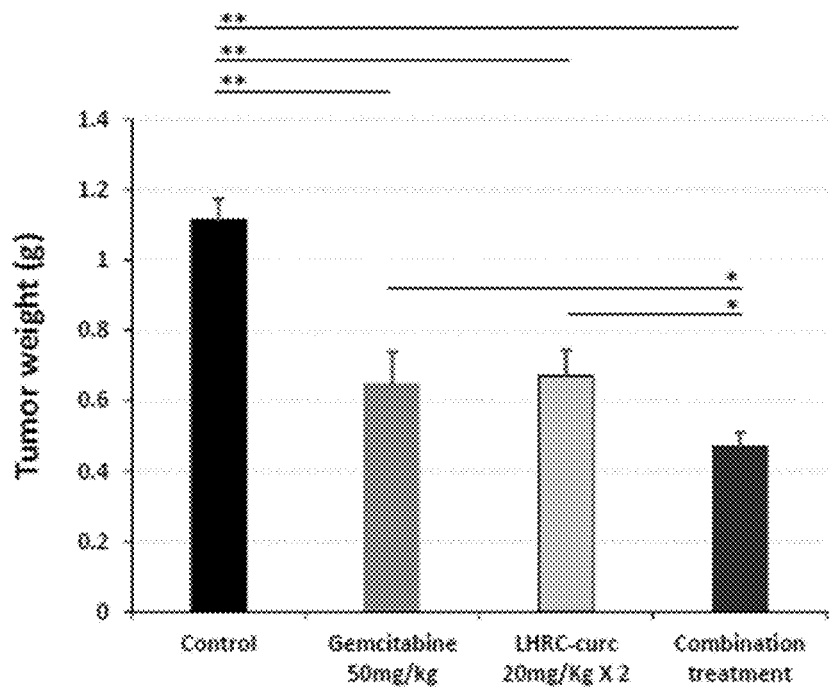
Figure 19:
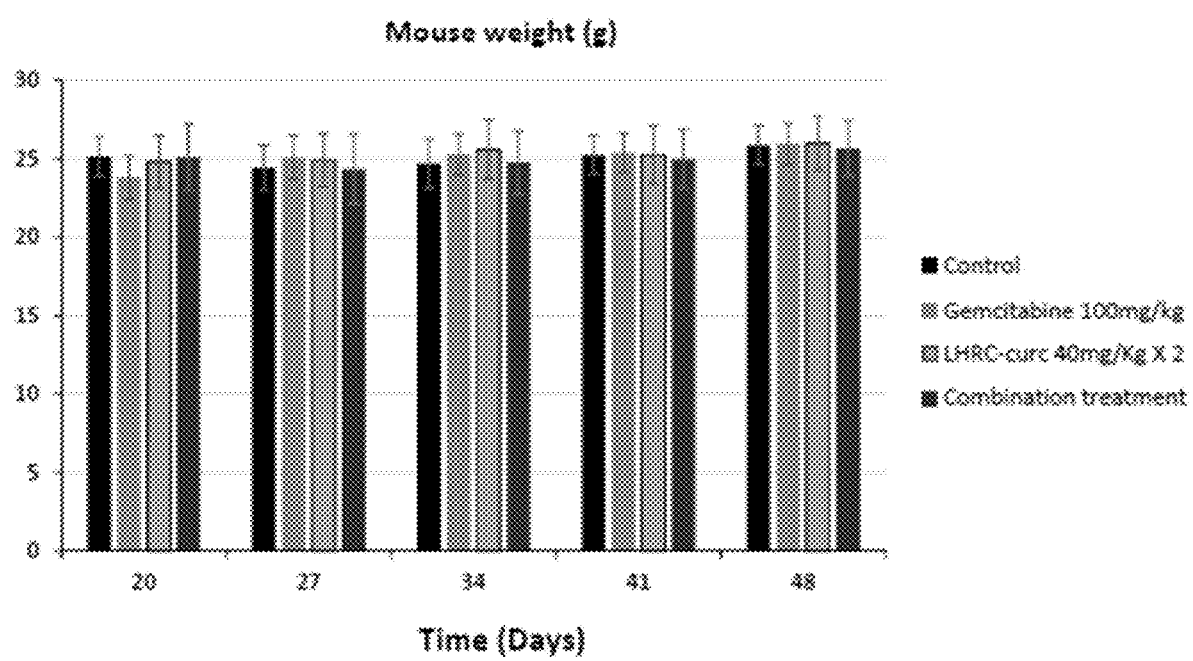
FIG. 19 shows changes in mice weight during treatment with high doses of gemcitabine and LHRH-curcumin: SCID/bg mice were treated weekly with intraperitoneal injections (IP) with vehicle alone (Control), gemcitabine (100 mg/kg, once a week), LHRH-curcumin (40 mg/kg, twice a week) or a combination of gemcitabine and LHRH-curcumin. Mice were monitored for 5 weeks starting on day 20 after tumor implantation. Therapeutic treatment of mice with higher doses of gemcitabine or LHRH-curcumin or a combination of the two compounds does not negatively impact body weight or body condition.
Figure 20:
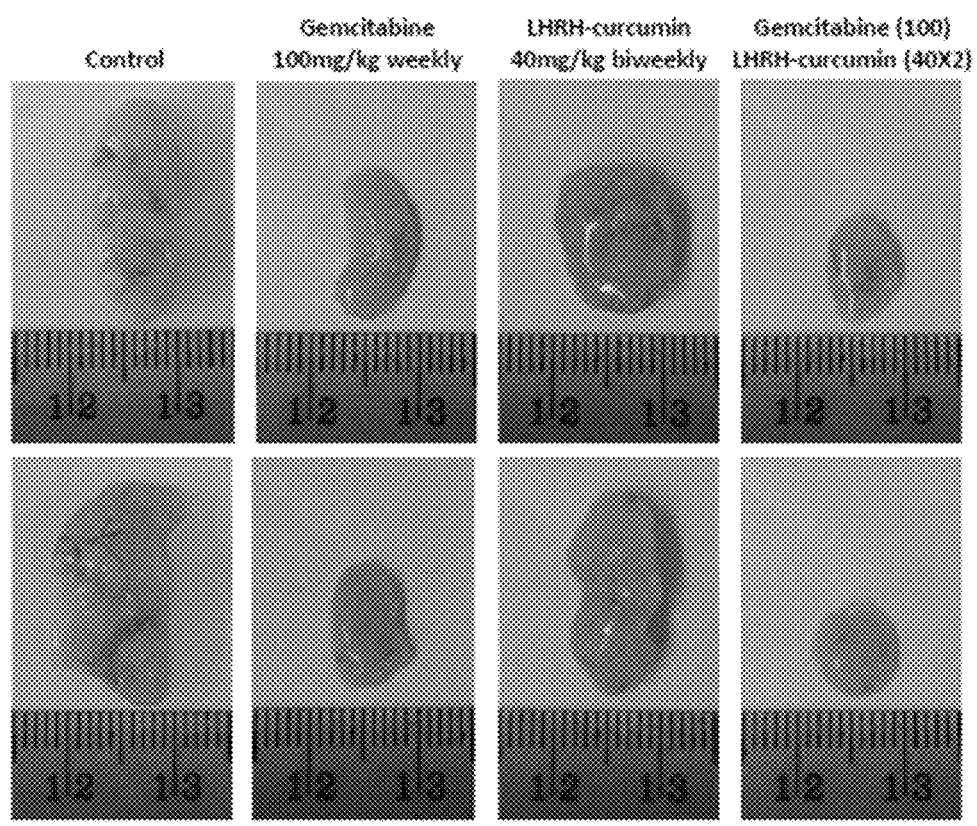
FIG. 20 shows the effect of high doses gemcitabine/LHRH-curcumin treatment on human pancreatic cancer cells Mia-Paca-2 in vivo: Mice were treated weekly with intraperitoneal injections (IP) with vehicle alone (Control), gemcitabine (100 mg/kg, once a week), LHRH curcumin (40 mg/kg, twice a week) or a combination of gemcitabine and LHRH-curcumin. Mice were monitored for 4 weeks starting on day 20 after tumor implantation. On day 48 postimplantation tumors were removed at necropsy. Representative images from vehicle treated, gemcitabine alone, LHRH-curcumin alone and combination treatment shows the evident reduction in tumor size in mice treated with combination of higher doses of gemcitabine and LHRH-curcumin.
Figure 21:
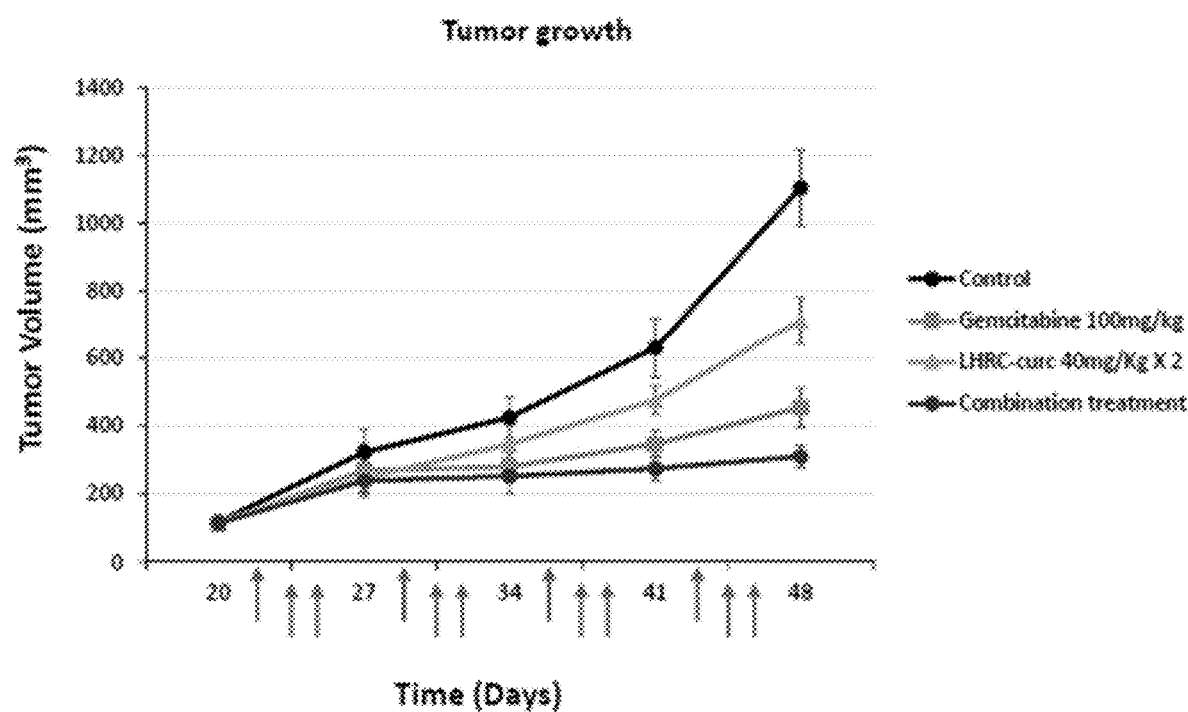
FIG. 21 shows high doses of gemcitabine/LHRH-curcumin combination treatment prevents the growth of pancreatic cancer cells Mia-Paca-2 in vivo: Changes in tumor volumes in SCID/bg mice receiving intraperitoneal injections with vehicle alone (Control), gemcitabine (orange arrows, 100 mg/kg, once a week), LHRH-curcumin (grey arrows, 40 mg/kg, twice a week) or a combination of gemcitabine and LHRH-curcumin. Data are presented as the mean±SD of tumor volume (n=8).
Figure 22A:
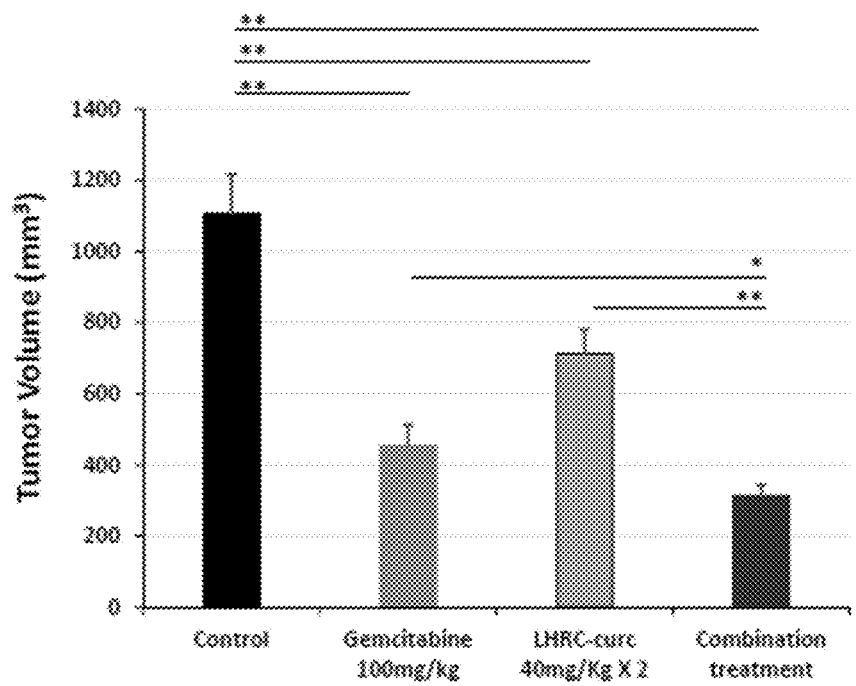
FIG. 22A-22B shows gemcitabine/LHRH-curcumin combination treatment prevents the growth of pancreatic cancer cells Mia-Paca-2 in vivo.
Figure 22B:
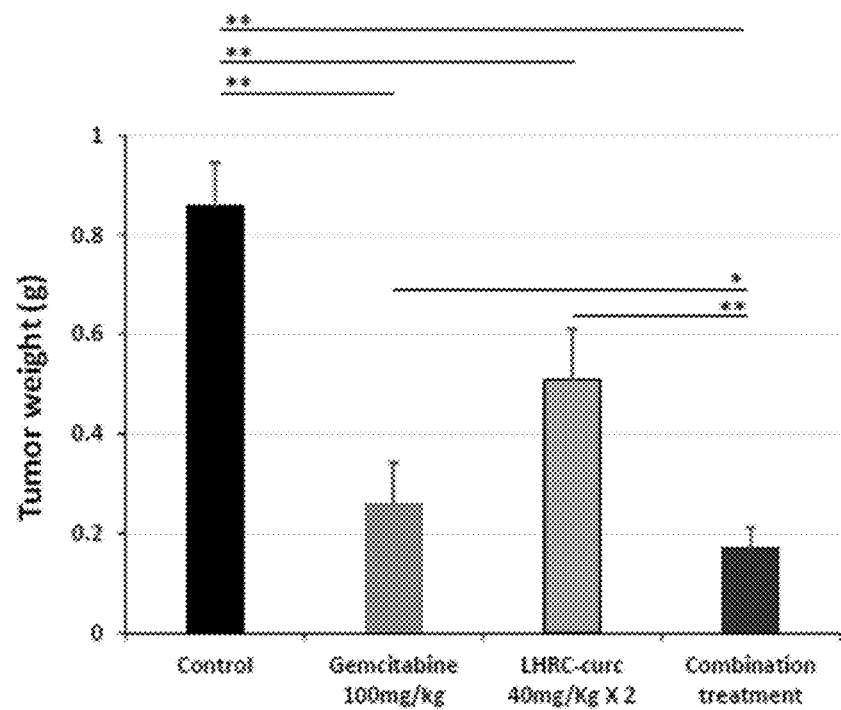
Figure 23A:
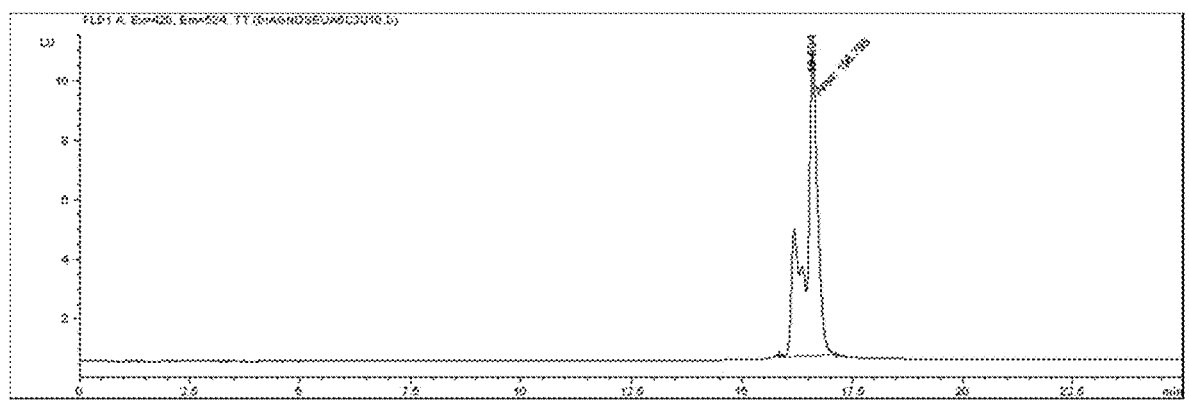
FIG. 23A-23B shows chromatographic characteristics of LHRH-curcumin vs free curcumin: Highperformance liquid chromatography (HPLC) analysis shows distinctive peaks for free curcumin FIG. 23A and LHRH-tagged curcumin FIG. 23B.
Figure 23B:
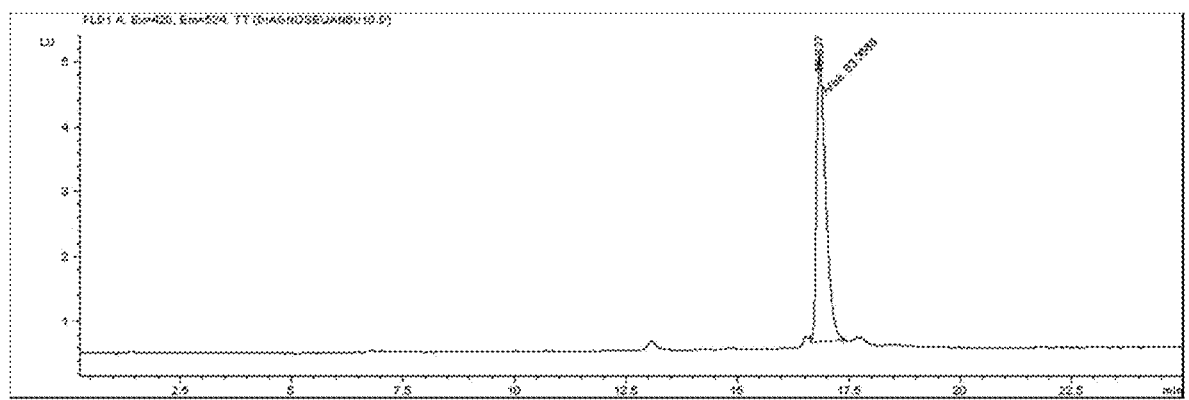
Figure 24:
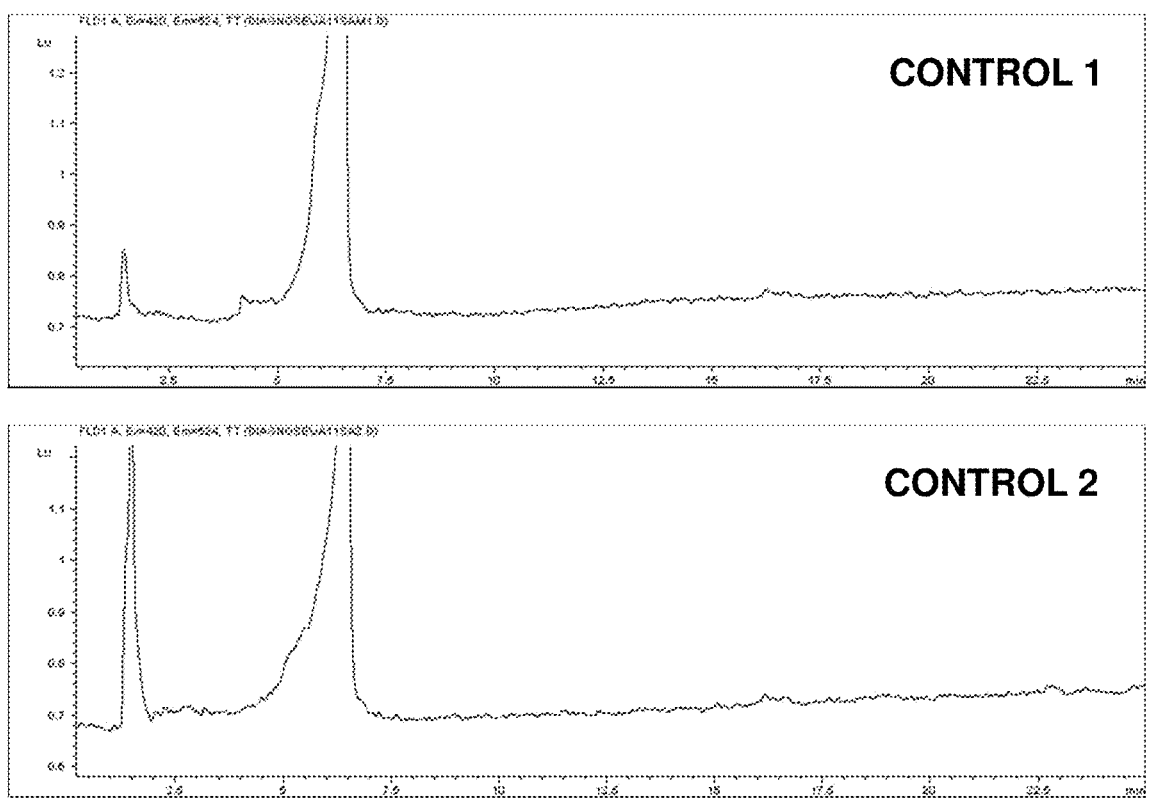
FIG. 24 shows HPLC analysis of tumor tissue from control-treated mice: No distinctive peaks were detected at 16.5-17 min in tissues extracted from tumors in control-treated mice.
Figure 25:
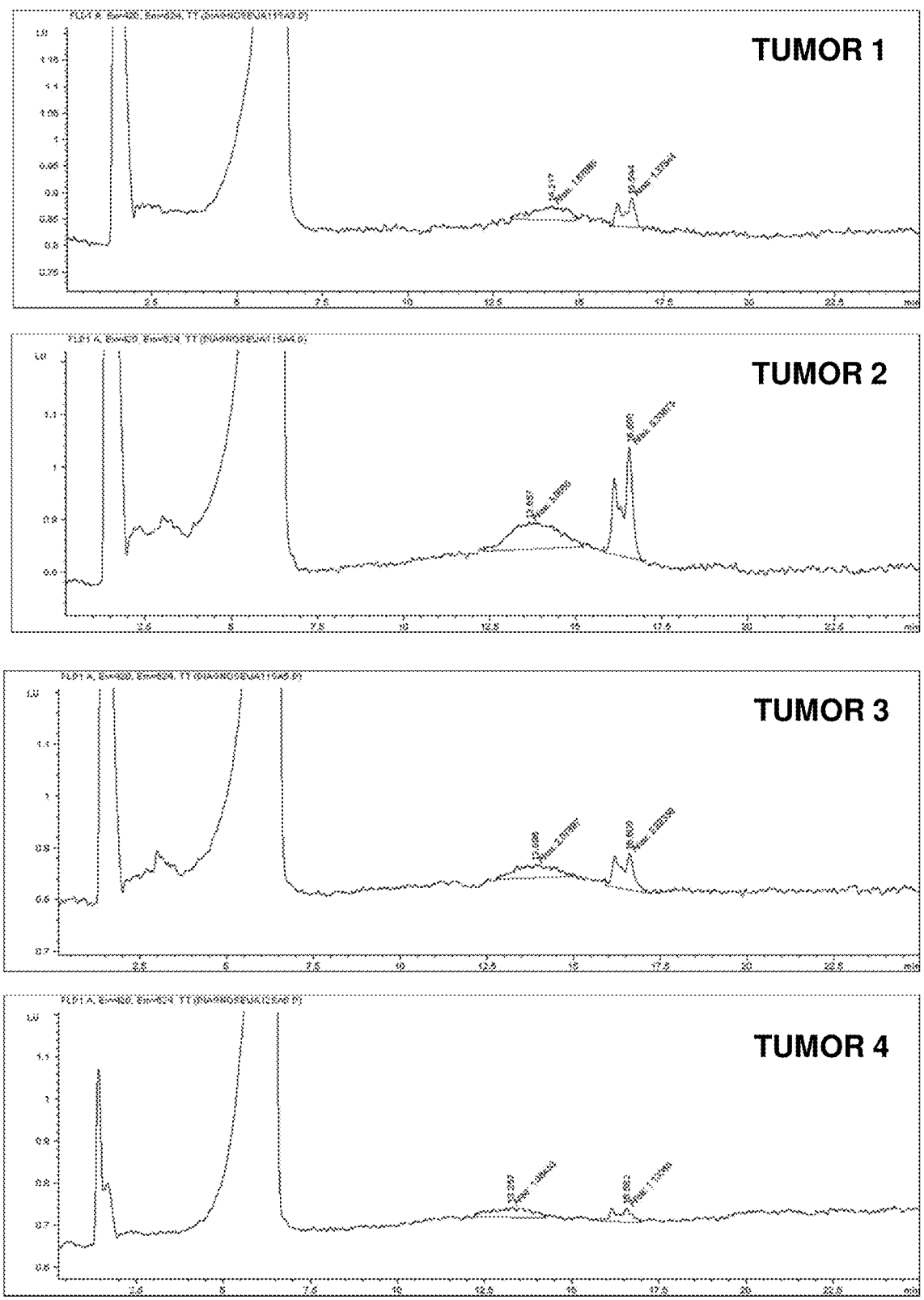
FIG. 25 shows HPLC analysis of tumor tissue from LHRH-curcumin-treated mice: Tumor tissue from four different mice treated with LHRH-curcumin twice a week (20 mg/kg) were subjected to HPLC analysis. All samples show a peak at approximately 16.5 min, indicative of free curcumin present in the extract. Broad peak prior to target is suggestive of a possible metabolite which was not present in control-treated samples.
Figure 26:
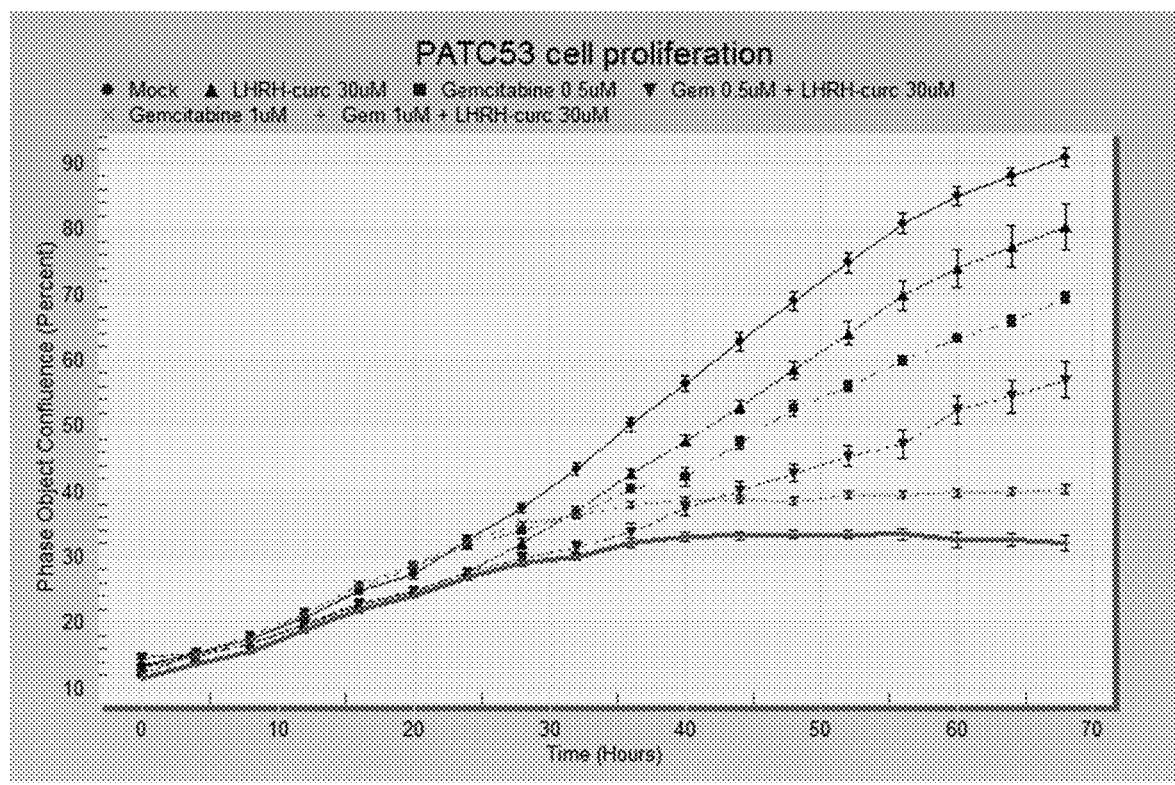
FIG. 26 shows quantification of cell proliferation/growth using IncucyteZoom software: percent (%) confluence was generated using images acquired during a 68 h time-course. Eight replicates per treatment were used for quantification. PATC53 are patient-derived pancreatic cancer cells obtained from MD Anderson. Previous analysis of LHRHR receptor expression suggests that PATC53 have low levels of the LHRHR receptor and require higher doses of LHRH-curcumin in order to detect an effect on cell death and/or cell proliferation. Combination of gemcitabine and LHRH-curcumin has a greater effect on cell proliferation inhibition than any of the drugs used alone.
Figure 27:
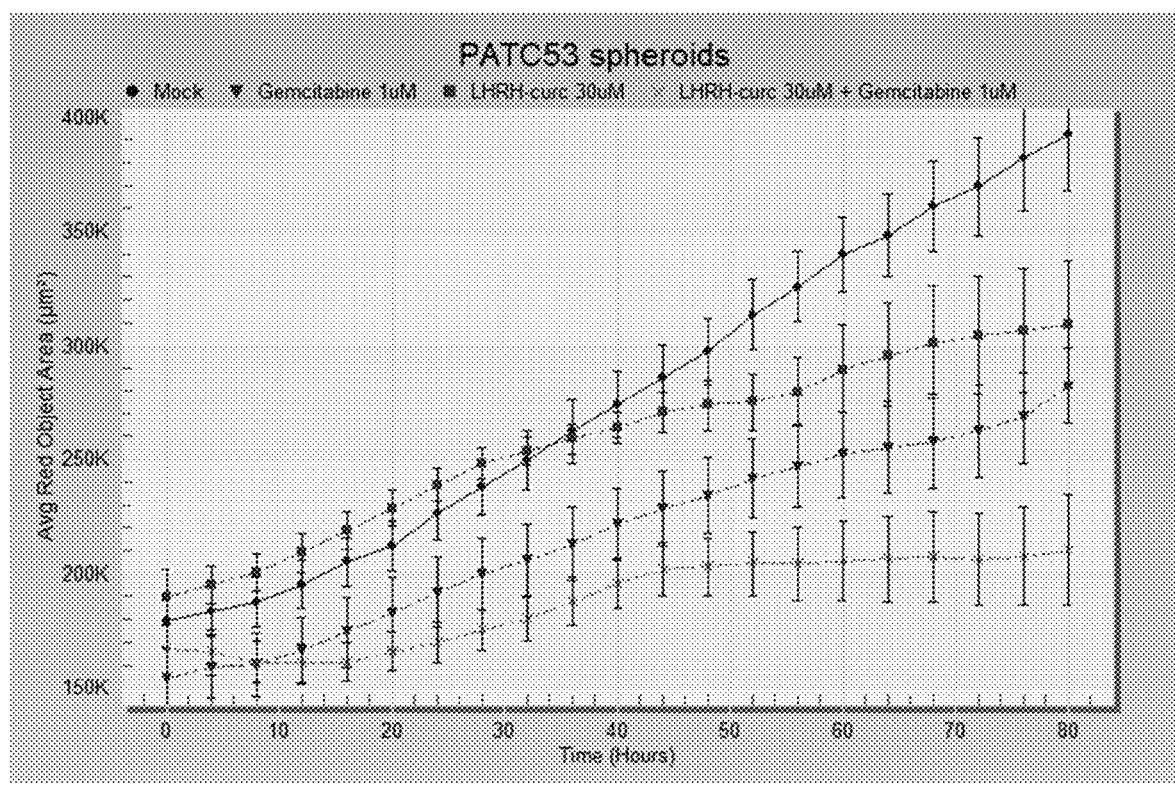
FIG. 27 shows PATC53 pancreatic cancer cells spheroids growth. Gemcitabine alone (1 μM), LHRH-curcumin alone (30 μM) and in combination were used to treat spheroid formed by PATC53 cells. Media alone was used as control. The spheroids were grown for 80 hours before quantification. Higher dose of LHRH-curcumin is used in order to detect an effect on spheroids growth. Combination of gemcitabine and LHRH-curcumin has a greater effect on spheroid growth inhibition than any of the drugs used alone.
Figure 28A:
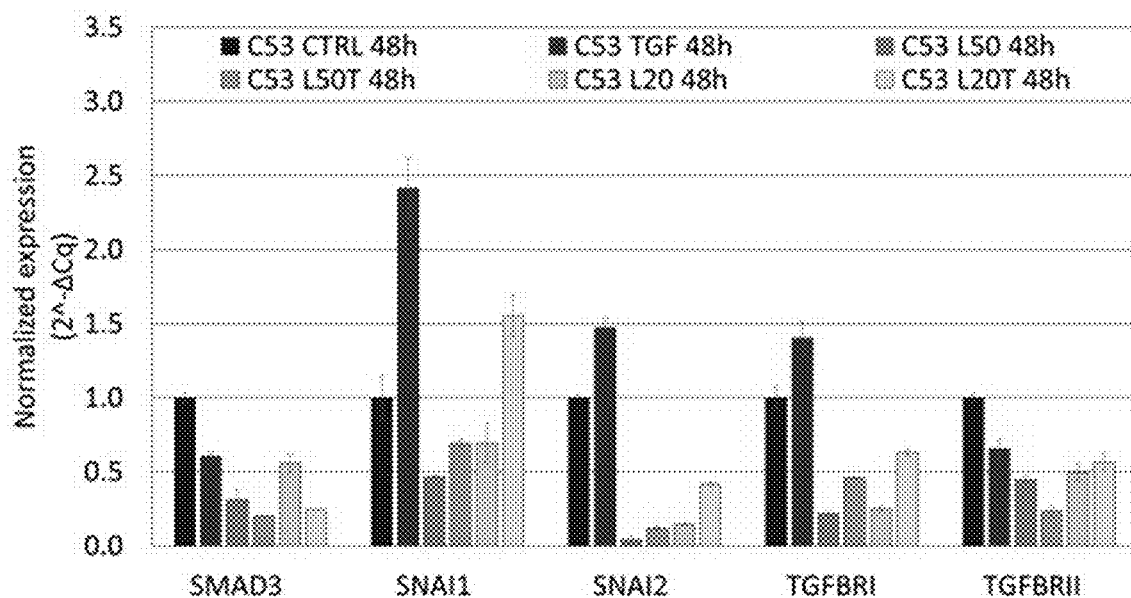
FIG. 28A-28B shows quantitative PCR analysis in PATC53 pancreatic cancer cells treated with TGFβ and LHRH-curcumin for 48 h.
Figure 28B:
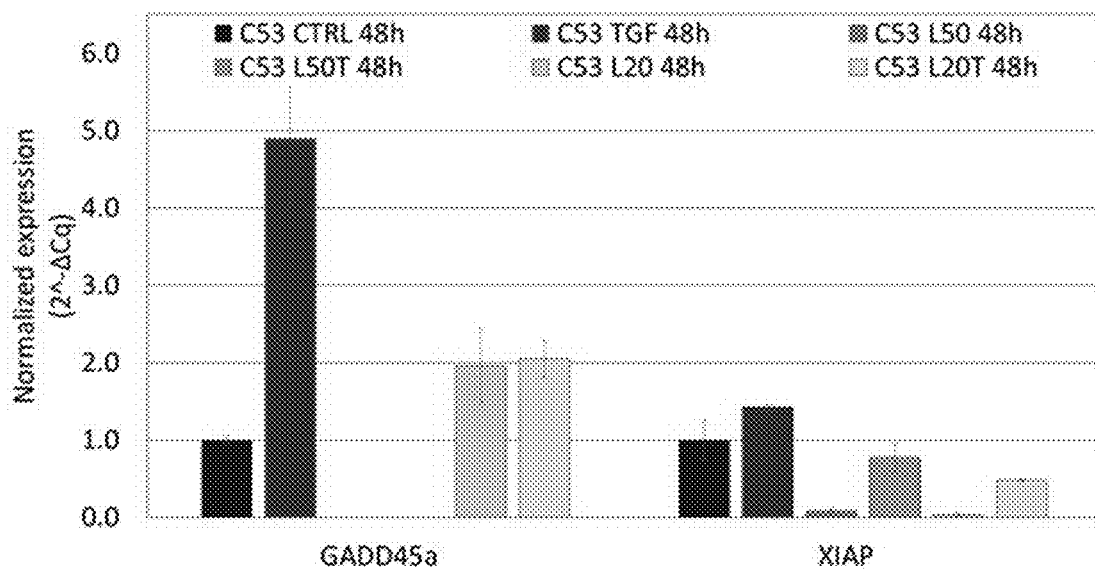
Figure 29:
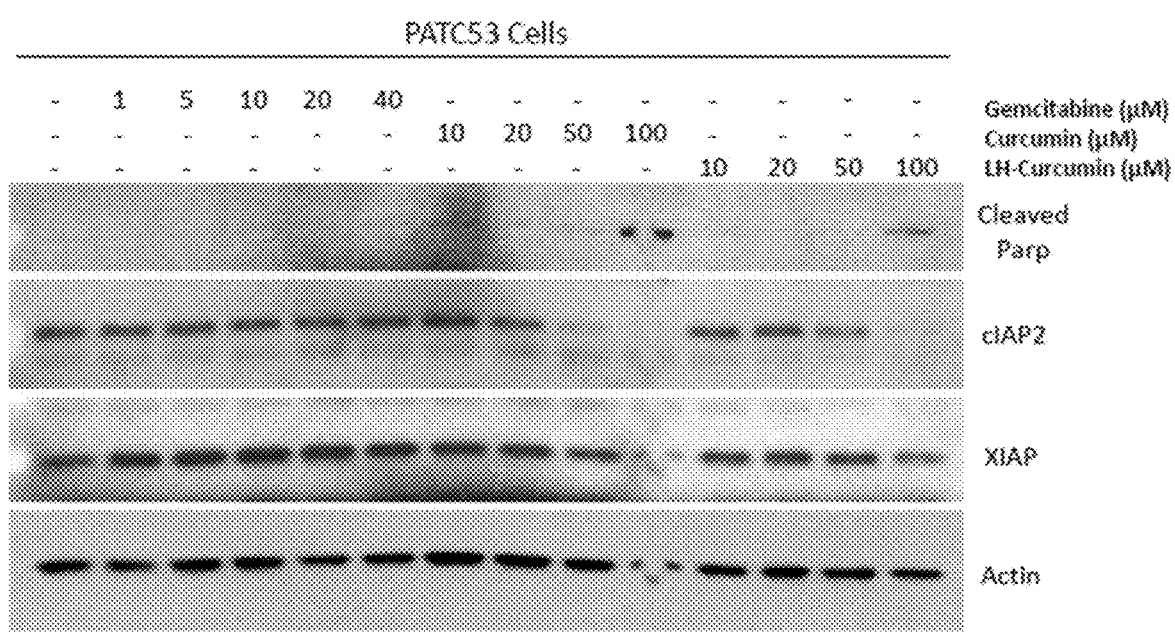
FIG. 29 shows western blot analysis of PATC53 cells. PATC53 cells were treated as described and Western blot was perform in order to detect apoptosis markers (cleaved PARP) and inhibitors of apoptosis (XIAP and cIAP2) 24 h post-treatment. Actin was used as loading controls. PATC53 cells show resistance to gemcitabine and lower doses of both curcumin and LHRH curcumin early during treatment. Markers of apoptosis were detected starting at 50 μM with both curcumin and LHRH-curcumin.
Figure 30:
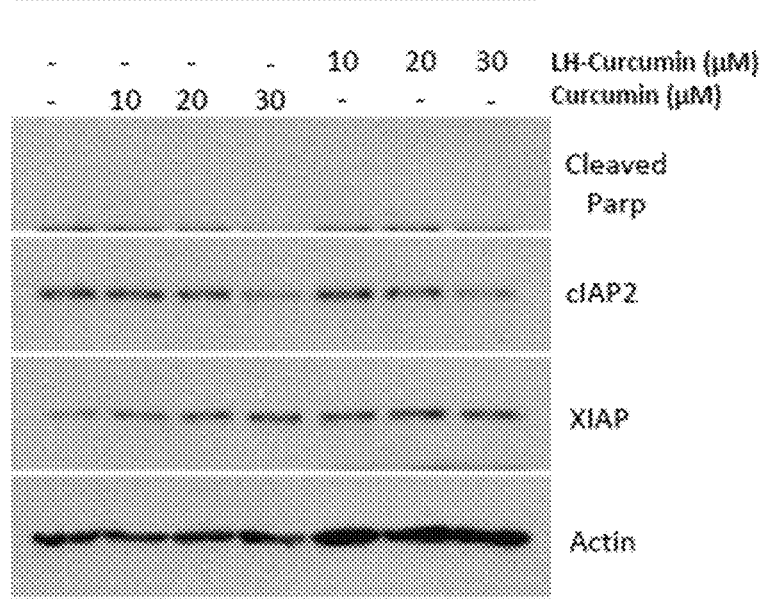
FIG. 30 shows western blot analysis of PATC53 cells. PATC53 cells were treated as presented and Western blot was perform in order to detect apoptosis markers (cleaved PARP) and inhibitors of apoptosis (XIAP and cIAP2) 48 h post-treatment. Actin was used as loading controls. Modest reduction of apoptosis inhibitors was detected at 30 μM LHRH-curcumin. The results suggest that PATC53 is resistant to LHRH-curcumin treatment at lower doses due to low expression of LHRHR.
Figure 30:
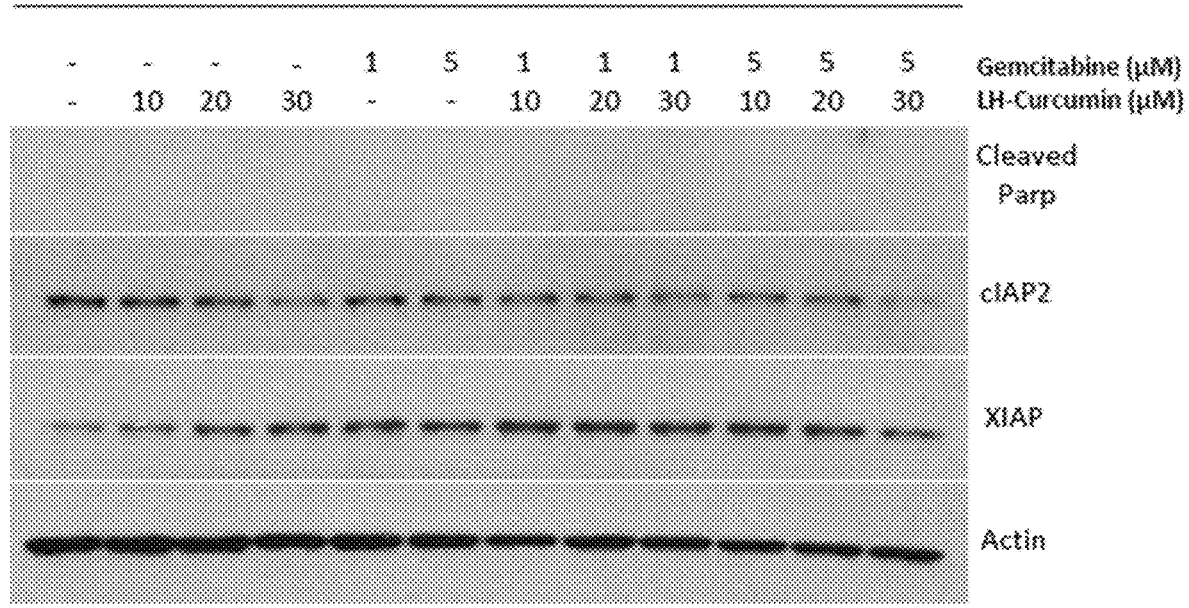
Figure 31:
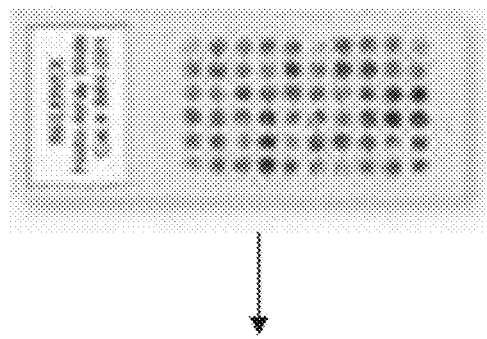
FIG. 31 is a schematic of ex vivo studies of LHRH-curcumin alone or in combination with other agents.
Figure 31:
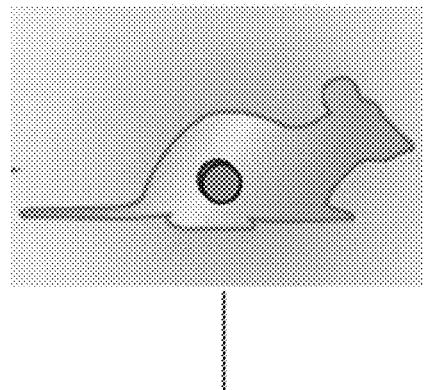
Figure 31:
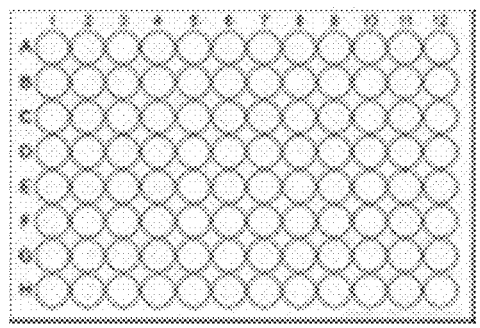

Results presented in FIG. 14. LHRH-receptor (LHRHR) is expressed at different levels in normal pancreatic cell line and cancer cell lines. MiaPaca-2 and Panc-1 cancer cell lines expressed LHRHR at highest levels.

Example 15

This example lists certain materials and methods used for the data developed in Example 16 and FIGS. 15-30.
Animals
Male SCID/bg mice (5 weeks old; Taconic Biosciences, NY) were housed in the standard mouse Plexiglas cages in a room maintained at constant temperature and humidity under a 12 h light and darkness cycle. The experimental protocol was reviewed and approved by the Institutional Animal Care and Use Committee at the LSUHSC Shreveport.
Subcutaneous Implantation of Mia-PaCa-2 Cells
Mia-PaCa-2 cells were harvested from cell cultures after trypsinization. The cells were washed once in serum-free medium and re-suspended in HBSS. Only suspensions consisting of single cells with >90% viability were used for the injections. Mice were injected s.c. on the right hind flank with $5 \times 10^6$ MIA-PaCa cells (ATCC, VA) in 50% Matrigel/HBSS with 26 Ga syringes.
Experimental Protocol
On day 21, after tumor cell implantation, mice bearing tumors between 100-200 mm3, were randomized into the following treatment groups (n=8): vehicle controls; gemcitabine treated (50 mg/kg or 100 mg/kg); LHRH-curcumin treated (20 mg/kg or 40 mg/kg); gemcitabine/LHRH curcumin treated. Treatments were made in 100 µL PBS and were given intraperitoneally by injections one weekly for gemcitabine and twice weekly for LHRH-curcumin for four weeks. The vehicle treated group received an equivalent amount of PBS. Tumor volumes were measured with calipers once a week and body weights of mice were measured once a week. Tumor volumes were calculated by the formula: V(mm3)=(length×width*2)/2, in which width was the shortest measurement in millimeters. Mice were necropsied 10 days after the last treatment for the low dose treatment (day 35 after the randomization and day 55 from the tumor cell implantation) or 2 days after the last treatment for high dose treatment (day 28 after the randomization and 48 from the tumor cell implantation). Tumors were dissected, weighed and photographed.
HPLC Tumor Extraction Method
Samples of tumor tissue were weighed, then pulverized using a Bessman Tissue Pulverizer cooled 3-5 minutes in liquid nitrogen. Resultant powder was then placed in glass homogenizing chamber, mixed in PBS to 20% solution, and crushed to produce final homogenate. 200 Ml aliquot of homogenate was dispensed in Axygen 2 mL clear microtube (Part #: MCT-200-C-S). Each sample was extracted with 1 mL 10% methanol/90% ethyl acetate, vortexed, and spun 30 minutes at 14,000 rpm in a cold room centrifuge. The upper organic phase layer was then removed and placed in separate microcentrifuge tubes. The procedure was repeated, and pooled tumor extracts were concentrated using a Savant SpeedVac. Samples were reconstituted in 100 µL of 1 mM ascorbic acidic MeOH (pH 4.6), mixed in a sonication bath for 2 minutes, and 75 µL were injected on-column. Reverse-phase HPLC (Agilent 1100 series) with a Thermo ODS Hypersil 5 µm 250 mm×4.6 mm analytical column (Part #: 30105-252130) operated at ambient temperature was used to quantify curcumin in tumor. The mobile phase was 0.1% TFA (Mobile A) and acetonitrile with 0.08% TFA (Mobile B). Extracted tumor samples were eluted using a gradient starting at 90% Mobile A/10% Mobile B increasing to 35% Mobile A/65% Mobile B from 0-15 minutes, and finally to 31.4% A/68.6% B by 25 minutes. The column was cleaned of residual curcumin using an injection of 100 µL of isopropanol in 100% of Mobile B for 20 minutes. With all analyses performed at 0.5 mL/min flow rate and fluorescence detection at Ex 420 nm and Em 524 nm, curcumin eluted at about 16.5 minutes.
Cell Proliferation Analysis
Pancreatic cancer cells were collected after trypsinization and seeded in 96-well plates for 24 h before treatments. Treatments were performed as described in Figure legends. Following treatment cell proliferation was analyzed using the "Phase Object Confluence" module of the IncucyteZOOM software.
Western Blot Analysis
Pancreatic cancer cells were collected after trypsinization and seeded in 12-well plates for 24 h before treatments. Treatments were performed as described in the Figure legends. Following treatment whole-cell lysates were collected in Laemmli buffer and analyzed by Western blot. The following primary antibodies were used: cleaved PARP, c-IAP2, XIAP, cleaved Parp-1 (all from Cell Signaling), actin (Santa Cruz).
Quantitative PCR Analysis
mRNA levels of Smad3, SNAI1, SNAI2, TGFBRI, TGF-BRII, GADD45 and XIAP were determined by quantitative real-time PCR using the Roche Universal Library Probe protocol. Thermal cycling was carried out using the LightCycler96 system from Roche under the following conditions: 95° C. for 10 min and 40 cycles at 95° C. for 15 s and 55° C. for 60 s. mRNA expression for any given gene is represented as comparative to the control-treated cells. GAPDH was used as the housekeeping gene of reference.

Example 16

This example is description of the results of an in vivo study of low and high doses of gemcitabine and LHRH-curcumin administered in combination, which strongly inhibited tumor growth.

In brief, intraperitoneal injections of low and high doses of gemcitabine and LHRH-curcumin in combination strongly inhibited the growth of Mia-PaCa-2 cancer cell xenografts in SCID mice. The mean volume and mean weight of the tumors of gemcitabine alone, LHRH-curcumin alone and drug combination treated mice were significantly (p=0.025) reduced comparing to the tumor volume and tumor weight of vehicle treated control mice. Importantly, the mean volume and mean weight of the tumors treated with a combination of drugs was significantly smaller than those of mice treated with single drugs.

While the low doses of gemcitabine and LHRH-curcumin did not completely prevent tumor growth, the combination of both drugs had a significantly stronger effect on tumor size than any of the individual treatments. Higher doses of drugs show a more profound effect on tumor growth. Mice treated with a combination of high dose of gemcitabine and LHRH-curcumin show a 4-5 fold reduction in tumor size when compared to control mice.

Drug treatments alone or in combination did not affect the health of the mice and significant changes in the mice body weight or appearance were not detected. This means that either lower or higher doses of gemcitabine and LHRH-curcumin can be used effectively to reduce tumor growth without significantly inducing side effects in this mouse model.

In order to specifically detect the presence of curcumin in the tumor HPLC analysis was performed on tumor tissue from control-treated and LHRH-curcumin treated mice. An ester bond is introduced between the two components of the conjugate during the synthesis of [DLys6]-LHRH-Curcumin. The bond is hydrolyzed by cellular esterases within the cell, allowing the free curcumin to act at the cellular level.

The HPLC analysis herein clearly shows curcumin accumulated in tumor tissue and also the presence of a possible metabolite. Free curcumin and its metabolite are absent from tumor tissue from control-treated mice. Detection of free curcumin in tumor tissue means that the drug is efficiently delivered to the tumor site and acts to inhibit tumor cells proliferation and induce tumor cells death.

Altogether, the in vivo results herein show superior effectiveness and bioavailability of LHRH-curcumin making this compound an excellent candidate for single and drug combination cancer treatments.

The effect of LHRH-curcumin on PATC53, a patient-derived pancreatic cancer cell line, was also examined. Previous analysis of PATC53 cells shows that this particular cell line displays low levels of LHRHR. The data herein are consistent with the previous data and show that PATC53 cells require higher levels of LHRH-curcumin in order to detect an effect on cell proliferation and/or cell death. Treatment with high doses of LHRH-curcumin also inhibited expression of genes involved in TGFβ pathway induction.

This data means that even when LHRHR is expressed at lower levels that treatment with LHRH-curcumin at higher doses still inhibits cell growth and metastasis induced by TGFβ pathway.

Example 17

This example is a description of further studies validating the antitumor activity of LHRH-curcumin alone or as a combination agent in pancreatic cancer patient-derived xenograft (PDX) models.

Growing PDXs Tumors:

Animal experiment protocol was reviewed and approved by The University of Texas MD Anderson Cancer Center (Houston, Tex.) institutional review board and in accordance with the Guidelines for the Care and Use of Laboratory Animals published by the National Institutes of Health. PDXs were grown from cryopreserved early passages of PDXs in nude mice as described in previous publications (Kim M P, et al, Nat Protoc 2009; 4(11): 1670-80). Briefly, tumor samples stored in CryoStor™ CS10 storage medium were recovered and cut into about 2 mm3 fragments, soaked in Matrigel, and implanted into the subcutaneous space of Balb/c nude mice (5 mice/PDX). Tumors were harvested when they reach 1.5 cm in diameter for generating tissue slices for drug testing with quadruplicates.

Live Tissue Sensitivity Assay (LTSA):

About 100 tissue slices were produced from 1 tumorgraft with tissue slicer and arrayed in 96-well plates with previously established method (Roife D, et al, Clin Cancer Res 2016). After 2 hours incubation, tissue slices will be treated with LHRH-curcumin (0, 3, 10, and 30 μM), 10 μM gemcitabine, or combinations. Same volume of medium with 0.1% DMSO was added into control wells. After 72 hours, tissue viabilities were measured with PrestoBlue method. Viability inhibition will be calculated through normalization of viabilities of tissue slices treated with inhibitor against the viability of control (DMSO treated) slices. Inhibition of viability was further analyzed with t-test. The tissue was defined as sensitive to the treatment if both $p<0.05$ and at least 30% of tissue slice viability on average was inhibited.

Statistical Analysis:

Significant difference between the treatments and control were analyzed with t-test. All statistical analysis were performed with GraphPad 8.0.

Figure 32:
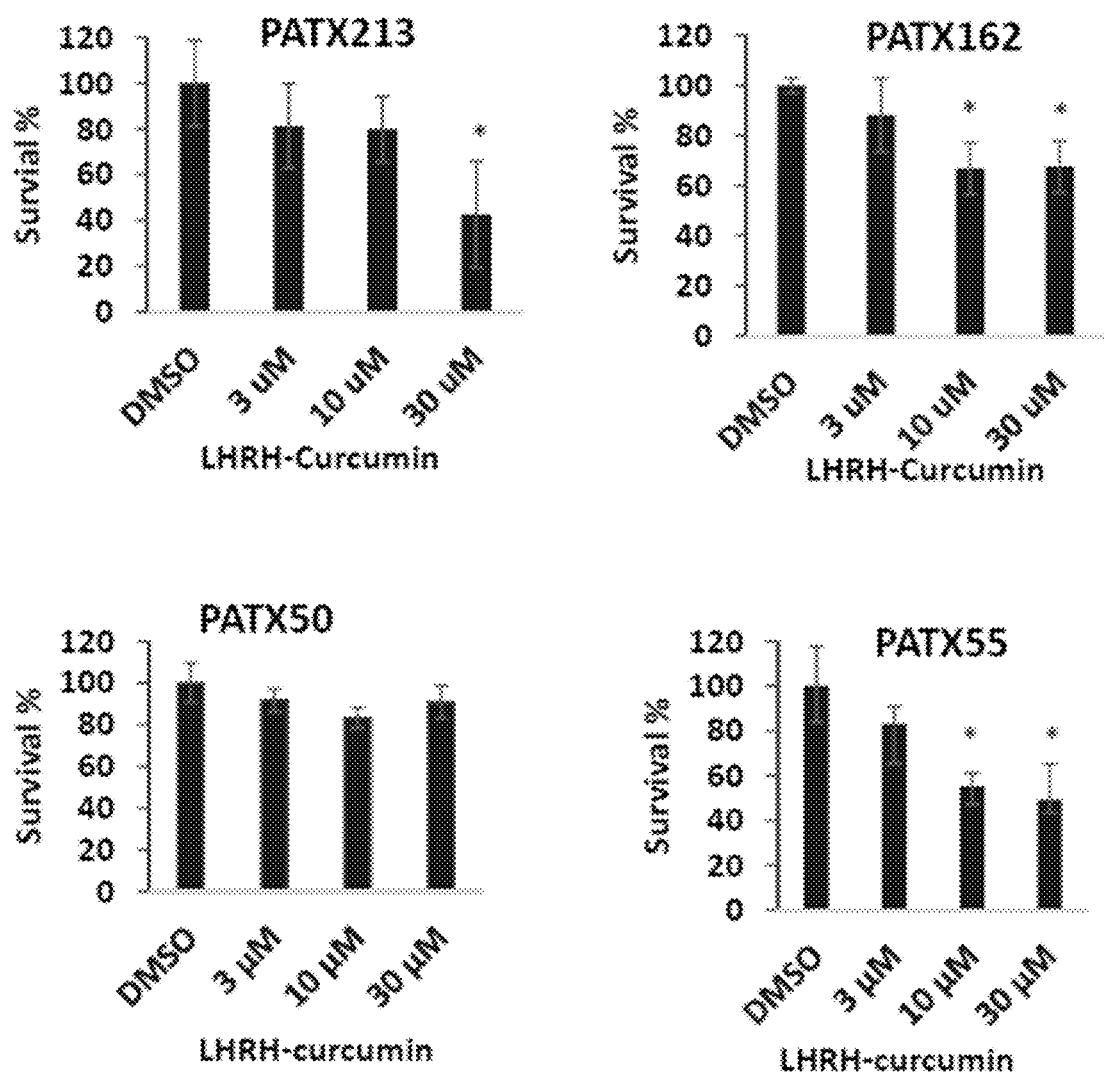
FIG. 32 shows ex vivo testing of LHRH-curcumin. Tissue slices from the indicated xenografts were treated with LHRH-curcumin for 72 hours, and tissue slice viabilities were measured with PrestoBlue (2 hours incubation). Significance of differences in tissue slice viabilities between treatment and control groups were analyzed with student's t-test. The tissue slice is defined as sensitive if both $p<0.05$ and viability was inhibited by at least 30 percent. *$p<0.05$.
Figure 33:
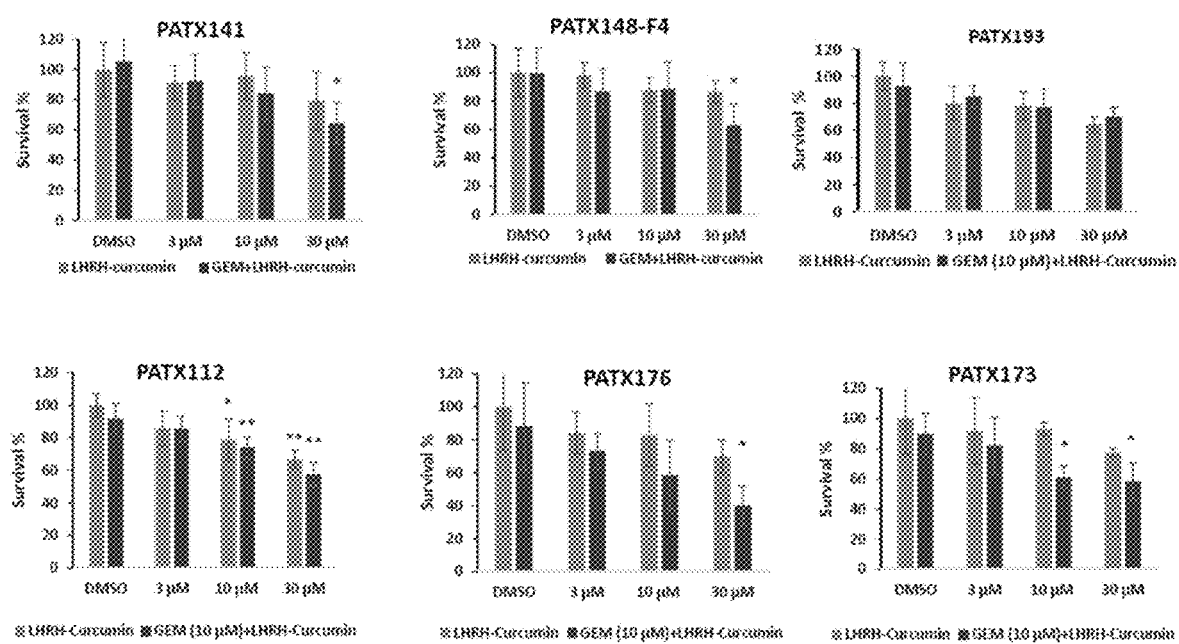
FIG. 33 shows combination of LHRH-curcumin and Gemcitabine. Tissue slices from the indicated xenografts were treated with LHRH-curcumin (0, 3, 10, and 30 μM), or 10 μM gemcitabine (GEM), or the combination for 72 hours, and tissue slice viabilities were measured with PrestoBlue (2 hours incubation). Significance of differences in tissue slice viabilities between treatment and control groups were analyzed with student's t-test. The tissue slice is defined as sensitive if both $p<0.05$ and viability was inhibited by at least 30 percent. *$p<0.05$; $p<0.01$; *$p<0.005$.
Figure 34:
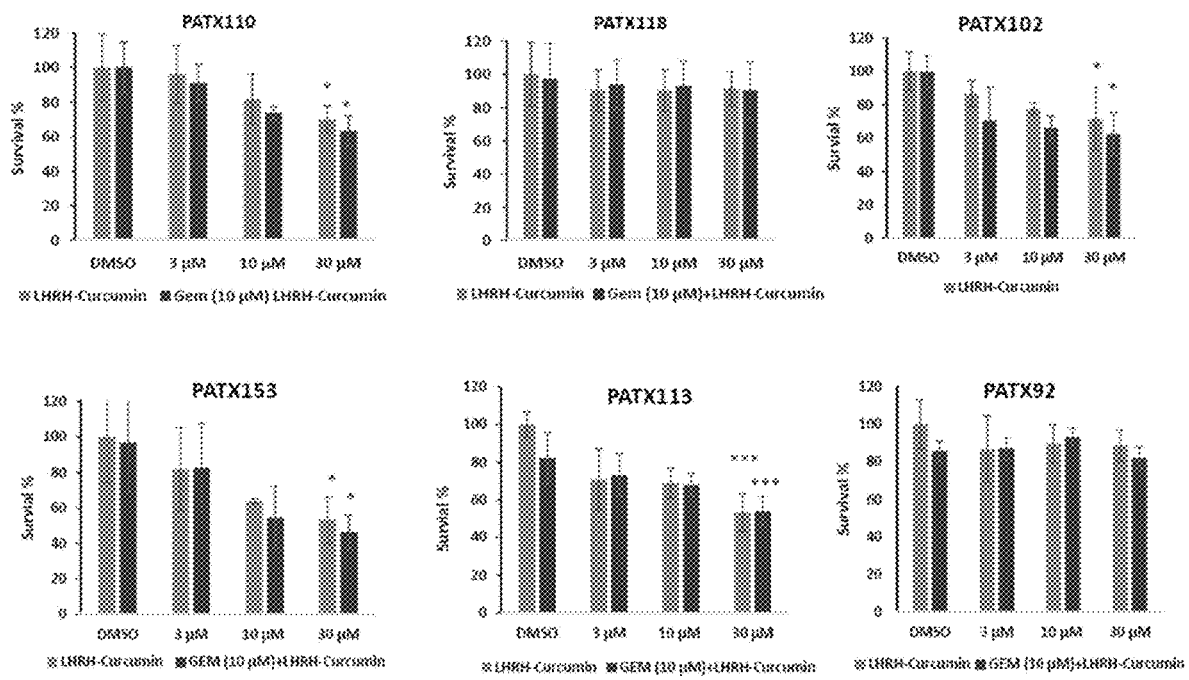
FIG. 34 shows combination of LHRH-curcumin and Gemcitabine. Tissue slices from the indicated xenografts were treated with LHRH-curcumin (0, 3, 10, and 30 µM), or 10 µM gemcitabine (GEM), or the combination for 72 hours, and tissue slice viabilities were measured with PrestoBlue (2 hours incubation). Significance of differences in tissue slice viabilities between treatment and control groups were analyzed with student's t-test. The tissue slice is defined as sensitive if both p<0.05 and viability was inhibited by at least 30 percent. *p<0.05; p<0.01; *p<0.005.

A subset of PDAC PDXs were sensitive to LHRH-curcumin and the combination treatments. A panel of 25 PDXs were implanted for the study. With LTSA assay (the method), a total 16 PDAC PDXs were tested for their responses to LHRH-curcumin, alone and in combination with gemcitabine. Based on the sensitivity criteria (30% viability inhibition and P value less than 0.05), 8 out 16 (50%) PDXs were sensitive to the LHRH-curcumin single agent treatment (FIGS. 32-34, and Table 1). In addition, the combination of gemcitabine (10 μM) further enhanced the antitumor activity of LHRH-curcumin in PTAX141, 148, 112, 176, 173, 102, and 153. In 14 PDXs tested 10 PDXs were sensitive to the combination treatment (FIGS. 33 and 34, and Table 2). The result suggest single LHRH-curcumin is active in a subset of PDAC PDXs, and that combination of gemcitabine and LHRH-curcumin further enhanced the antitumor activities of LHRH-curcumin.

The data show that about 50% PDXs were sensitive to the LHRH-curcumin single agent treatment. Thus, the combination of gemcitabine and LHRH-curcumin enhanced the antitumor activities of LHRH-curcumin in a subset of PDXs.

TABLE 1

Summary of the response of PDXs to LHRH-curcumin single agent treatment.

| PDX | DMSO | LHRH-C 3 μM | LHRH-C 10 μM | LHRH-C 30 μM | # P value | Sensitivity |
|---|---|---|---|---|---|---|
| PATX213 | 100 | 81.3 | 79.9 | 42.52 | 0.0228 | Sensitive |
| PATX55 | 100 | 83.06 | 55.1 | 49.14 | 0.001 | |
| PATX153 | 100 | 81.83 | 64.03 | 53.09 | 0.0479 | |
| PATX113 | 100 | 70.84 | 68.95 | 53.294 | 0.0003 | |
| PATX193 | 100 | 79.78 | 78.22 | 64.48 | 0.0045 | |
| PATX112 | 100 | 85.58 | 78.7 | 66.67 | 0.0003 | |
| PATX162 | 100 | 88.24 | 66.8 | 67.51 | 0.0269 | |
| PATX110 | 100 | 96.09 | 81.74 | 69.87 | 0.0264 | |
| PATX176 | 100 | 84.04 | 82.87 | 69.99 | 0.0767 | Resistant |
| PATX102 | 100 | 86.67 | 77.78 | 71.68 | 0.0423 | |
| PATX173 | 100 | 91.74 | 92.75 | 77.32 | 0.1071 | |
| PATX141 | 100 | 91.09 | 95.55 | 79.23 | 0.1631 | |
| PATX148 | 100 | 98.07 | 87.7 | 86.49 | 0.2034 | |
| PATX92 | 100 | 86.79 | 89.61 | 88.56 | 0.1852 | |

TABLE 1-continued

Summary of the response of PDXs to LHRH-curcumin single agent treatment.

| PDX | DMSO | LHRH-C 3 μM | LHRH-C 10 μM | LHRH-C 30 μM | # P value | Sensitivity |
|---|---|---|---|---|---|---|
| PATX50 | 100 | 91.67 | 83.35 | 90.7 | 0.5105 | |
| PATX118 | 100 | 90.51 | 90.28 | 91.46 | 0.4630 | |

P: Treatment (30 μM LHRH-curcumin) vs non-treatment control

TABLE 2

Summary of the response of PDXs to the combination of LHRH-curcumin and gemcitabine.

| PDX | Gem 10 μM | Gem + LHRH-C 3 μM | Gem + LHRH-C 10 μM | Gem + LHRH-C 30 μM | * p value | Sensitivity |
|---|---|---|---|---|---|---|
| PATX55 | 95.45 | 52.01 | 42.30 | 31.75 | 0.0006 | Sensitive |
| PATX176 | 88.23 | 73.35 | 58.53 | 40.34 | 0.0023 | |
| PATX153 | 96.86 | 82.80 | 54.65 | 46.30 | 0.0029 | |
| PATX113 | 82.19 | 73.34 | 68.08 | 54.19 | 0.0023 | |
| PATX112 | 91.71 | 85.54 | 74.00 | 57.70 | 0.0207 | |
| PATX173 | 89.87 | 82.13 | 61.05 | 58.37 | 0.0194 | |
| PATX102 | 99.65 | 70.47 | 66.26 | 62.56 | 0.0160 | |
| PATX148 | 99.55 | 86.70 | 88.46 | 62.85 | 0.0011 | |
| PATX110 | 100.20 | 91.08 | 73.77 | 63.20 | 0.0010 | |
| PATX141 | 105.35 | 92.36 | 84.12 | 64.48 | 0.0231 | |
| PATX193 | 92.70 | 85.12 | 77.09 | 70.16 | 0.0014 | Resistant |
| PATX92 | 85.63 | 86.98 | 93.25 | 82.08 | 0.0277 | |
| PATX118 | 97.56 | 94.16 | 92.98 | 90.42 | 0.0160 | |
| PATX50 | 104.96 | 88.71 | 98.53 | 96.62 | 0.0174 | |

* P: combination treatment (10 μM GEM and 30 μM LHRH-curcumin) vs non-treatment control.

Example 18

This is a description of studies to ascertain LHRH Receptor expression. The data show that expression of LHRH receptor (LHRH-R) is associated with the response to LHRH-curcumin.

LHRH Receptor Assay in Tissue Microarray (TMA):

LHRH-Receptor expressions were measured with established method in a clinical histopathology core laboratory. The staining of LHRH-R was quantified under the microscope using the scores of 0 for non-expression, 1 for low expression, 2 for moderate expression, and 3 for high expression.

Statistical Analysis

Pearson correlation was used to analyze the correlation between the expression of LHRH-R and the sensitivities of PDXs to LHRH-curcumin or combinations. All statistical analysis were performed with GraphPad 8.0.

Figure 35:
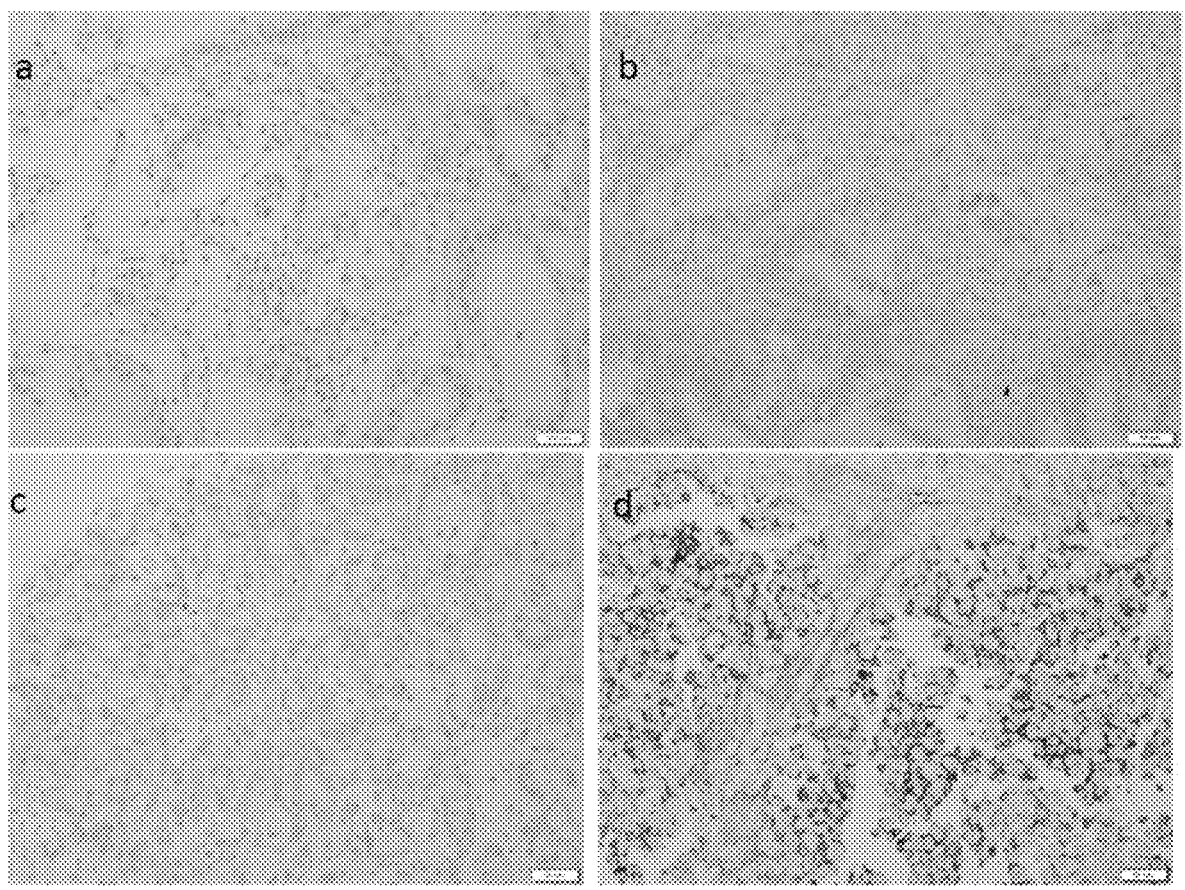
FIG. 35 is an illustration of LHRH-R expression levels. PDX TMAs were stained for LHRH-R expression using immunohistochemistry staining. Staining was analyzed under microscope and scored with intensity score method, 0: non-staining; 1: weak staining; 2: moderate staining; 3: strong staining.

Expression of LHRH-R were analyzed in a panel of 88 PDX tumors arrayed in two tissue microarrays. Staining of LHRH-R was examined under the microscope and scored (FIG. 35). The expression of LHRH-R in 12 tested PDXs were scored. Another 4 PDXs tumors were not in the TMA sets. The expression levels of LHRH-R and the PDX sensitivities are summarized in Table 3. Correlation analysis found that LHRH-R expression is strongly associated the sensitivity of PDX tumors to LHRH-curcumin single agent treatment.

Using an ex vivo live tumor drug sensitivity assay combined with PDX models, 16 PDAC PDX tumors derived from 16 different patients were analyzed. The results show that about 50% of the PDXs tested were sensitive to the single agent LHRH-curcumin treatment (30 μM), and when combined with gemcitabine, the antitumor activity was further enhanced in a subset of PDX tumors, showing that about 70% of the PDXs were sensitive to the combination treatment.

Because the PDX models have been proved to be the most reliable models to assess the efficacy of therapeutic agents, these results indicate that LHRH-curcumin alone or in combination with other agents is/are a promising strategy for pancreatic cancer treatment. The results also show that expression of LHRH receptor was associated with the responses to LHRH-curcumin, indicating that LHRH receptor level could be a predictive marker for patient selection in future clinic trials with these regimens.

TABLE 3

Summary of the response of PDXs and LHRH-R expression, and the correlation between the response and LHRH-R expression level.

| PDX | Sensitivity To LHRH-C | LHRH-R values | PDX | Sensitivity to Combo | LHRH-R values |
|---|---|---|---|---|---|
| PATX213 | Sensitive | UN | PATX55 | Sensitive | 3 |
| PATX55 | Sensitive | 3 | PATX176 | Sensitive | 1 |
| PATX153 | Sensitive | UN | PATX153 | Sensitive | UN |
| PATX113 | Sensitive | 3 | PATX113 | Sensitive | 3 |
| PATX193 | Sensitive | 1 | PATX112 | Sensitive | 3 |
| PATX112 | Sensitive | 3 | PATX173 | Sensitive | 1.5 |
| PATX162 | Sensitive | UN | PATX102 | Sensitive | 2.5 |
| PATX110 | Sensitive | 3 | PATX148 | Sensitive | 0.5 |
| PATX176 | Resistant | 1 | PATX110 | Sensitive | 3 |
| PATX102 | Resistant | 2.5 | PATX141 | Sensitive | 1 |
| PATX173 | Resistant | 1.5 | PATX193 | Resistant | 1 |
| PATX141 | Resistant | 1 | PATX92 | Resistant | 1 |
| PATX148 | Resistant | 0.5 | PATX118 | Resistant | 2 |
| PATX92 | Resistant | 1 | PATX50 | Resistant | UN |
| PATX50 | Resistant | UN | | | |
| PATX118 | Resistant | 2 | | | |
| | R = 0.6531 | N = 12 | | R = 0.333 | N = 12 |

UN, unknown.

What is claimed is:

1. A method for reducing or inhibiting proliferation of a cell comprising:
   a) contacting a cell that expresses a receptor that binds to a LHRH or a LHRH analog with a LHRH or a LHRH analog fused or conjugated to curcumin or a curcumin analog; and
   b) contacting the cell with an anti-cell proliferative drug.

2. The method of claim 1, wherein the LHRH or a LHRH analog fused or conjugated to curcumin or a curcumin analog is administered prior to, substantially contemporaneously with or following administration of the anti-cell proliferative drug.

3. The method of claim 1, wherein the receptor that binds to said LHRH or LHRH analog is a LHRH-receptor.

4. The method of claim 1, wherein the receptor that binds to said LHRH or LHRH analog is present on the cell surface.

5. The method of claim 1, wherein the receptor that binds to said LHRH or LHRH analog is intracellular.

6. The method of claim 1, wherein the cell or hyperproliferative disorder is present in lung, thyroid, head or neck, nasopharynx, throat, nose or sinuses, brain, spine, breast, adrenal gland, pituitary gland, thyroid, lymph, gastrointestinal, mouth, esophagus, stomach, duodenum, ileum, jejunum, small intestine, colon, rectum, genito-urinary tract, uterus, ovary, cervix, endometrial, bladder, testicle, prostate, kidney, pancreas, liver, bone, bone marrow, lymph, blood, skin or muscle.

7. The method of claim 1, wherein the cell, hyperproliferative disorder or neoplasia, tumor, cancer or malignancy is metastatic.

8. The method of claim 1, wherein the cell, hyperproliferative disorder or neoplasia, tumor, cancer or malignancy comprises a solid cellular neoplasia, tumor, cancer or malignancy.

9. The method of claim 1, wherein the cell, hyperproliferative disorder or neoplasia, tumor, cancer or malignancy comprises a lymphatic or hematopoietic cell neoplasia, tumor, cancer or malignancy.

10. The method of claim 9, wherein the hematopoietic neoplasia, tumor, cancer or malignancy comprises a myeloma, lymphoma or leukemia.

11. The method of claim 1, wherein the cell, hyperproliferative disorder or neoplasia, tumor, cancer or malignancy comprises a carcinoma, sarcoma, lymphoma, leukemia, adenoma, adenocarcinoma, melanoma, glioma, glioblastoma, meningioma, neuroblastoma, retinoblastoma, astrocytoma, oligodendrocytoma, mesothelioma, reticuloendothelial neoplasia, tumor, cancer or malignancy.

12. The method of claim 11, wherein the sarcoma comprises a lymphosarcoma, liposarcoma, osteosarcoma, chondrosarcoma, leiomyosarcoma, rhabdomyosarcoma or fibrosarcoma.

13. The method of claim 1, wherein the anti-cell proliferative drug comprises gemcitabine, 5-fluorouracil, cyclophosphamide, azathioprine, cyclosporin A, prednisolone, melphalan, chlorambucil, mechlorethamine, busulphan, methotrexate, 6-mercaptopurine, thioguanine, cytosine arabinoside, AZT, 5-azacytidine (5-AZC), bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol (paclitaxel), vinblastine, vincristine, doxorubicin, dibromomannitol, irinotecan, topotecan, etoposide, teniposide, or pemetrexed.

14. The method of claim 1, wherein the anti-cell proliferative drug is administered at a dose from about 25-250, 250-500, 500-1000, 1000-2500 or 2500-5000, 5000-25,000, 5000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 5000-50,000 µg/kg, to the subject.

15. The method of claim 1, wherein the LHRH or a LHRH analog fused or conjugated to curcumin or a curcumin analog is administered at a dose from about 25-250, 250-500, 500-1000, 1000-2500 or 2500-5000, 5000-25,000, 5000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 5000-50,000 µg/kg, to the subject.

16. The method of claim 1, wherein the method or use inhibits or reduces relapse or progression of the neoplasia, tumor, cancer or malignancy.

17. The method of claim 1, wherein the method or use results in partial or complete destruction of the neoplastic, tumor, cancer or malignant cell mass, volume, size or numbers of cells, stimulating, inducing or increasing neoplastic, tumor, cancer or malignant cell necrosis, lysis or apoptosis, reducing neoplasia, tumor, cancer or malignancy volume size, cell mass, inhibiting or preventing progression or an increase in neoplasia, tumor, cancer or malignancy volume, mass, size or cell numbers, or prolonging lifespan.

18. The method of claim 1, wherein the method or use reduces or decreases severity, duration or frequency of an adverse symptom or complication associated with or caused by the neoplasia, tumor, cancer or malignancy, or pain, discomfort, nausea, weakness or lethargy.

19. The method of claim 1, wherein the method increases energy, appetite, improved mobility or psychological well-being of a subject.

20. The method of claim 1, wherein the cell, hyperproliferative disorder or neoplasia, tumor, cancer or malignancy is present in a mammal.

21. The method of claim 1, wherein the LHRH or a LHRH analog fused or conjugated to curcumin or a curcumin analog or the anti-cell proliferative drug is administered to the subject or mammal locally, regionally, or systemically, or into the cell, hyperproliferative disorder or neoplasia, tumor, cancer, or metastasis.

22. The method of claim 1, wherein the cell is in a subject.

23. The method of claim 22, wherein the subject or mammal is a human.

24. The method of claim 22, wherein the subject or mammal is a domestic or farm (livestock) animal.

25. The method of claim 24, wherein the domestic animal is a dog or a cat.

26. A method for reducing or inhibiting proliferation of a cell comprising contacting a cell that express a receptor that binds to a LHRH or a LHRH analog with
   a) a luteinizing hormone-releasing hormone (LHRH) or a LHRH analog; and
   b) curcumin or a curcumin analog,
   wherein said LHRH or LHRH analog is fused or conjugated to said curcumin or curcumin analog; and
   c) an anti-cell proliferative drug.

27. A method for treating a hyperproliferative disorder comprising:
   a) contacting cells of the hyperproliferative disorder that express a receptor that binds to a LHRH or a LHRH analog with a hormone (LHRH) or a LHRH analog fused or conjugated to curcumin or a curcumin analog; and
   b) contacting said cells of the hyperproliferative disorder with an anti-cell proliferative drug.

28. A method for treating a hyperproliferative disorder comprising contacting cells of the hyperproliferative disorder that express a receptor that binds to LHRH or a LHRH analog with
   a) a luteinizing hormone-releasing hormone (LHRH) or a LHRH analog; and
   b) curcumin or a curcumin analog,
   wherein said LHRH or LHRH analog is fused or conjugated to said curcumin or curcumin analog; and
   c) an anti-cell proliferative drug.

29. A method for treating a neoplasia, tumor, cancer or malignancy that expresses a receptor that binds to LHRH or a LHRH analog, comprising:
   a) administering to a subject a LHRH or a LHRH analog fused or conjugated to curcumin or a curcumin analog; and
   b) administering to the subject an anti-cell proliferative drug.

30. The method of claim 29, wherein the neoplasia, tumor, cancer or malignancy comprises a lung, thyroid, head or neck, nasopharynx, throat, nose or sinuses, brain, spine, breast, adrenal gland, pituitary gland, thyroid, lymph, gastrointestinal, mouth, esophagus, stomach, duodenum, ileum, jejunum, small intestine, colon, rectum, genito-urinary tract, uterus, ovary, cervix, endometrial, bladder, testicle, prostate, kidney, pancreas, liver, bone, bone marrow, lymph, blood, skin or muscle neoplasia, tumor, cancer or malignancy.

31. The method of claim 29, wherein the neoplasia, tumor, cancer, or metastasis comprises a stage I, II, III, IV or V neoplasia, tumor, cancer, or metastasis.

32. The method of claim 29, wherein the neoplasia, tumor, cancer, or metastasis is progressively worsening, or is in remission.

33. A method for treating a neoplasia, tumor, cancer or malignancy that expresses a receptor that binds to LHRH or an LHRH analog, comprising administering
   a) a luteinizing hormone-releasing hormone (LHRH) or a LHRH analog; and
   b) curcumin or a curcumin analog,
   wherein said LHRH or LHRH analog is fused or conjugated to said curcumin or curcumin analog; and
   c) an anti-cell proliferative drug to said neoplasia, tumor, cancer or malignancy.

* * * * *

SEQUENCE LISTING

<160> NUMBER OF SEQ ID NOS: 5

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: LHRH analog

<400> SEQUENCE: 1

```
Glu His Trp Ser Tyr Gly Leu Arg Pro Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: LHRH analog

<400> SEQUENCE: 2

Ala Phe Ala Ser Lys Lys Leu Lys Pro Ala
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Linker
      Peptide

<400> SEQUENCE: 3

Gly Ser Gly Gly Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Linker
      Peptide

<400> SEQUENCE: 4

Ala Ser Ala Ala Ser
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Linker
      Peptide

<400> SEQUENCE: 5

Cys Cys Cys Cys Cys Cys
1               5
```